(12) United States Patent
Fujise et al.

(10) Patent No.: US 7,691,567 B2
(45) Date of Patent: Apr. 6, 2010

(54) METHODS AND COMPOSITIONS RELATING TO FORTILIN, AN ANTI-APOPTOTIC MOLECULE, AND MODULATORS OF FORTILIN

(75) Inventors: Ken Fujise, Houston, TX (US); Edward T. H. Yeh, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 260 days.

(21) Appl. No.: 10/021,753

(22) Filed: Oct. 30, 2001

(65) Prior Publication Data

US 2003/0172388 A1 Sep. 11, 2003

Related U.S. Application Data

(60) Provisional application No. 60/244,416, filed on Oct. 30, 2000.

(51) Int. Cl.
C12Q 1/68 (2006.01)
(52) U.S. Cl. .......................................................... 435/6
(58) Field of Classification Search ..................... 435/6, 435/4; 530/350
See application file for complete search history.

(56) References Cited

U.S. PATENT DOCUMENTS

| 5,270,163 | A | * | 12/1993 | Gold et al. ....................... 435/6 |
| 5,948,639 | A | * | 9/1999 | Gimeno et al. .............. 435/69.1 |
| 6,228,586 | B1 | * | 5/2001 | Messier et al. .................. 435/6 |
| 2002/0102532 | A1 | * | 8/2002 | Augustus ........................ 435/4 |

FOREIGN PATENT DOCUMENTS

| WO | WO 94/12881 | | 6/1994 |
| WO | WO 9719749 A1 | * | 6/1997 |
| WO | WO 98/04291 | | 2/1998 |
| WO | WO 01/18046 | | 3/2001 |

OTHER PUBLICATIONS

Henikoff et al. (Science 1997; vol. 278(5338), pp. 609-614).*
Witkowski et al. (Biochemistry 1999; vol. 38, pp. 11643-11650).*
Seffernick et al. (J. Bacteriol. 2001; vol. 183(8), pp. 2405-2410).*
Mullins et al. (1996) J. Clin. Invest. vol. 98, pp. 1557-1560.*
Mullins et al. (1993) Hypertension vol. 22, pp. 630-633.*
Cameron (1997) Molec. Biotech. vol. 7, pp. 253-265.*
Kappel et al. (1992) Current Opinion in Biotechnology, vol. 3, pp. 548-553.*
Baudet et al., "Differentially expressed genes in C6.9 glioma cells during vitamin D-induced cell death program," *Cell Death Differ*, 5(1):116-125, 1998.
Chitpatima et al., "Nucleotide sequence of a major messenger RNA for a 21 kilodalton polypeptide that is under translational control in mouse tumor cells," *Nucleic Acids Res.*, 16:2350, 1988.
Chung et al., "Expression of translationally controlled tumor protein mRNA in human colon cancer," *Cancer Lett.*, 156:185-190, 2000.

Fujise et al., "Regulation of apoptosis and cell cycle progression by MCL1," *J Biol Chem*, 275:39458-39465, 2000.
GenBank Accession No. X16064.
Gross et al., "cDNA sequence coding for a translationally controlled human tumor protein," *Nucleic Acids Res.*, 17:8367, 1989.
Haghighat and Ruben, "Purification of novel calcium binding proteins form *Trypanosoma brucei*: properties of 22-, 24- and 38-kilodalton proteins," *Mol and Biochem Parasitology*, 51:99-110, 1992.
Li et al., "Characterization of fortilin, a novel antiapoptotic protein," *J. Biol. Chem.*, 276:47542-47549, 2001.
MacDonald et al., "Chromosomal localization[1] of tumor protein, translationally-controlled 1 (TPT1) encoding the human histamine releasing factor (HRF) to 13q12—q14," *Cytogenet Cell Genet*, 84:128-129, 1999.
MacDonald et al., "Molecular identification of an IgE-dependent histamine-releasing factor," *Science*, 269:688-690, 1955.
Moulding et al., "Mcl-1 expression in human neutrophils: regulation by cytokines and correlation with cell survival," *Blood* 92(7), 2495-2502, 1998.
Sturzenbaum et al., "Identification of heavy metal induced changes in the expression patterns of the translationally controlled tumour protein (TCTP) in the earthworm *Lumbricus rubellus*," *Biochimica et Biophysica Acta*, 1398:294-304, 1998.
Teshima et al., "Macrophage colony-stimulating factor stimulates synthesis and secretion of a mouse homolog of a human IgE-dependent histamine-releasing factor by macrophages in Vitro and In Vivo," *J. Immunology*, 161:6356-6366, 1998.
Thiele et al., "Expression of the gene and processed pseudogenes encoding the human and rabbit translationally controlled tumour protein (TCTP)," *Eur. J. Biochem.*, 267:5473-5481, 2000.
Thiele et al., "Structure of the promoter and complete sequence of the gene coding for the rabbit translationally controlled tumor protein (TCTP) P23," *Eur. J. Biochem.*, 257:62-68, 1998.
Bhisutthibhan et al., "The *Plasmodium falciparum* translationally controlled tumor protein homolog and its reaction with the antimalarial drug artemisinin," *J. Biol. Chem.*, 273(26):16192-16198, 1998.

(Continued)

Primary Examiner—Jon E Angell
(74) Attorney, Agent, or Firm—Fulbright & Jaworski L.L.P.

(57) ABSTRACT

The polypeptide Fortilin (also known as Translationally Controlled Tumor Protein, TCTP) specifically interacts with p53, a tumor suppressor involved in the induction of apoptosis and the normal growth regulation of a cell. Fortilin also specifically binds MCL1 (Myeloid Cell Leukemia 1). Fortilin has the ability to prevent apoptosis, which may be unregulated in hyperproliferative cells. The present invention is directed at compositions and methods involving a Fortilin modulator, which can induce apoptosis, for the prevention, treatment, or diagnosis of hyperproliferative diseases and conditions, including cancer and atherosclerosis. It is directed also at compositions and methods involving Fortilin, which can inhibit apoptosis, for the treatment of diseases and condition characterized by apoptosis, including certain vascular conditions.

8 Claims, 17 Drawing Sheets

OTHER PUBLICATIONS

Garrigos et al., "Detection of $Ca^{2+}$-binding proteins by electrophoretic migration in the presence of $Ca^{2+}$ combined with $^{45}Ca^{2+}$ overlay of protein blots," *Analytical Biochemistry*, 194:82-88, 1991.

Yoon et al., "Identification of the self-interaction of rat TCTP/IgE-dependent histamine-releasing factor using yeast two-hybrid system," *Archives of Biochem. And Biophys.*, 384(2):379-382, 2000.

Gachet et al., "The growth-related translationally controlled protein p23 has properties of a tubulin binding protein and associates transiently with microtubules during the cell cycle," *Journal of Cell Science*, 112:1257-1271, 1999.

Sinha et al., "Identification of novel proteins associated with the development of chemoresistance in malignant melanoma using two-dimensional electrophoresis," *Electrophoresis*, 21: 3048-3057, 2000.

* cited by examiner

FIG. 1A

METHODS AND COMPOSITIONS RELATING TO FORTILIN, AN ANTI-APOPTOTIC MOLECULE, AND MODULATORS OF FORTILIN

The present application claims priority to U.S. Provisional Patent Application Ser. No. 60/244,416 filed on Oct. 30, 2000. The entire text of the above-referenced disclosure is specifically incorporated herein by reference without disclaimer.

This invention was made with government support under grant number 1KO8HL04015 awarded by the National Institutes of Health. The government has certain rights in the invention.

BACKGROUND OF THE INVENTION

1. Field of the Invention

The present invention relates generally to the fields of biochemistry, molecular biology, and diagnosis and therapy for hyperproliferative cell diseases and conditions, such as cancer and atherosclerosis. More particularly, it concerns a Fortilin polypeptide, the gene or transcript encoding it, modulators of Fortilin and their relevance to cancer and vascular diseases.

2. Description of Related Art

Heart disease and cancer are the leading causes of death, respectively, in the United States. In 1997, 41.2 percent of deaths in the United States (953,110 lives) were caused by a cardiovascular disease, and cancer caused 539,377 deaths (americanheart.org). More than a million Americans are expected to have a heart attack a year, while cancer strikes one in two men and one in three women (Landis, 1998).

The growth of normal cells is a controlled process. A cell whose growth is not controlled may proliferate more frequently, becoming hyperproliferative. Cancer is an example of a disease characterized by hyperproliferative cells. The development of cancer is understood as the culmination of complex, multistep biological processes, occurring through the accumulation of genetic alterations. Many if not all of these alterations involve specific cellular growth-controlling genes that are mutated. These genes typically fall into two categories: proto-oncogenes and tumor suppressor genes. Mutations in genes of both classes generally confer a growth advantage on the cell containing the altered genetic material.

The function of tumor suppressor genes, as opposed to proto-oncogenes, is to antagonize cellular proliferation. When a tumor suppressor gene is inactivated, for example by point mutation or deletion, the cell's regulatory machinery for controlling growth is upset. Tumor suppressor genes include Rb, p53, APC, WT-1, p16, NF-1, NF-2, and VHL.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors. The loss of proper p53 functioning is associated with the loss of cell growth control. The lack of proper p53 function can be either due to mutated (or altered) p53 or due to the presence of p53 inhibitors. In recent years, several p53 inhibitors have been identified. These include Mdm-2, Bcl-2, BRCA2, and others. These inhibitors negatively regulate p53 through various mechanisms: Mdm-2 and BRCA2 directly bind to p53, thereby interfering with its function. Bcl-2, on the other hand, blocks the entry of p53 to the nucleus.

p53 has been shown by several laboratories to promote apoptosis, which is programmed cell death. Other proteins, however, have been shown to prevent apoptosis; for example, overexpression of Bcl-xL and MCL1 (Myeloid Cell Leukemia 1), a Bcl-2 homologue, prevented HeLa cells from undergoing apoptosis, consistent with previous reports (Schmitt et al., 1998; Zhou et al., 1997). Cancer alters the regulation of apoptosis, so polypeptides involved in the process of apoptosis have also been implicated in cancer.

The gene products of proto-oncogenes, as alluded to above, typically are involved in pathways of normal cell growth or differentiation. Many of the participants of these pathways, when genetically mutated, contribute to the promotion of tumor development and the genes encoding them are consequently termed "oncogenes." The polypeptides encoded by proto-oncogenes include transcriptions factors (e.g. c-fos, c-jun, c-myc), growth factor receptors (eg., c-fms, c-erbB, c-kit), growth factors (e.g., c-sis, int-2) and cell cycle proteins (e.g., PRAD1). Mutations in one or more proto-oncogenes—that is, the presence of one or more oncogenes—has been shown to be associated with specific cancers. Unlike tumor suppressors genes involved in cancer, oncogenes express a protein product that possesses activity. Thus, the treatment of cancer may involve inactivating, inhibiting, or reducing the activity of one or more oncogene products.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. These therapies each are accompanied with varying side effects and they have varying degrees of efficacy. Furthermore, gene therapy is an emerging field in biomedical research with a focus on the treatment of disease by the introduction of therapeutic recombinant nucleic acids into somatic cells of patients. Various clinical trials using gene therapies have been initiated and include the treatment of various cancers, AIDS, cystic fibrosis, adenosine deaminase deficiency, cardiovascular disease, Gaucher's disease, rheumatoid arthritis, and others. However, there is a continued need for effective cancer therapies. Moreover, there is a persistent need for diagnostic assays that identify individuals who are predisposed to cancer, as well as to identify the prognosis of a particular cancer patient.

Similarly, there is a need for effective therapies in the treatment of other hyperproliferative cell diseases and conditions, particularly atherosclerosis. Numerous treatments exist for atherosclerosis. However, given the number of patients afflicted with these diseases and conditions involving atherosclerosis, as well as the number who die from diseases involving it, continued efforts to improve therapy are necessary.

As additional therapies and diagnostic methods for hyperproliferative diseases and conditions, such as cancer and atherosclerosis, are needed, the present invention focuses on the interactions discovered between the tumor suppressor p53 and Fortilin and between myeloid cell leukemia (MCLI) and Fortilin, as well as on the anti-apoptotic properties of Fortilin. The present invention concerns compositions and methods involving the Fortilin polypeptide and modulators of Fortilin to address the need for additional therapies and diagnostic methods.

SUMMARY OF THE INVENTION

The present invention takes advantage of the observations that Fortilin binds p53 and prevents apoptosis and that Fortilin binds MCL1 and prevents apoptosis. Therefore, the present invention is directed at therapeutic and diagnostic methods and compositions involving fortilin nucleic acids and Fortilin polypeptide compositions, as well as modulators that affect Fortilin polypeptides and nucleic acid molecules to either induce apoptosis or inhibit apoptosis. Any of the nucleic acid- and proteinaceous compound-containing compositions disclosed herein may be practiced with respect to other compositions and methods of the invention.

In some embodiments of the present invention, methods of inhibiting a hyperproliferative cell by providing to the cell an effective amount of a Fortilin inhibitor, wherein the inhibitor reduces Fortilin activity in the cell. As discussed below, a Fortilin inhibitor is a compound that directly or indirectly inhibits or reduces Fortilin activity in a particular environment (ie., cell, or a cell-free system that may be used for assaying activity). In further embodiments of the invention, a Fortilin inhibitor reduces Fortilin activity by reducing Fortilin binding to p53 or by reducing Fortilin binding to MCL1. In still further embodiments a Fortilin inhibitor decreases the amount of Fortilin in the cell. The amount of Fortilin can be reduced or decreased by decreasing the expression of Fortilin, which can be effected by decreasing transcription of Fortilin, decreasing translation of Fortilin, increasing the turnover rate of Fortilin, rendering the Fortilin polypeptide or Fortilin-encoding mRNA less stable, or decreasing the half lives of Fortilin or Fortilin-encoding mRNA.

In some embodiments, a Fortilin inhibitor specifically binds a Fortilin polypeptide. The Fortilin inhibitor may be a polypeptide or small molecule. In some cases, the inhibitor is an antibody, including a monoclonal antibody. Alternatively, a Fortilin inhibitor may be a nucleic acid molecule, such as a Fortilin antisense molecule or a ribozyme that binds a Fortilin-encoding nucleic acid molecule. In some embodiments the Fortilin inhibitor is provided to a hyperproliferative cell by an expression cassette that includes a nucleic acid segment encoding the inhibitor. As mentioned above, the inhibitor may be a nucleic acid molecule, and thus, it may be a nucleic acid containing a promoter operably linked to a nucleic acid segment encoding at least 30 contiguous nucleotides of the human Fortilin cDNA sequence (SEQ ID NO:1). This sequence may be positioned in reverse orientation under the control of a promoter that directs expression of an antisense product.

Hyperproliferative cells include cancer or precancer cells, which may be a bladder, blood, bone, bone marrow, brain, breast, colon, esophagus, gastrointestine, gum, head, kidney, liver, lung, nasopharynx, neck, ovary, prostate, skin, stomach, testis, tongue, or uterus cell. In some embodiments of the invention, the hyperproliferative cell being treated is a vascular cell, such as an endothelial cell which include but is not limited to vascular smooth muscle cells, and atherosclerosis and post-angioplasty restenosis. Also contemplated as part of the invention is treatment of a hyperproliferative cell in an animal. The treatment of a human is specifically considered an embodiment of the invention.

Methods of treating patients with a Fortilin modulator are also part of the present invention. These include methods of treating a patient with a hyperproliferative disease or condition involving administering to the patient an amount of a Fortilin inhibitor effective to reduce Fortilin activity, thereby conferring a therapeutic benefit on the subject. The term "therapeutic benefit" used throughout this application refers to anything that promotes or enhances the well-being of the subject with respect to the medical treatment of his condition, which includes treatment of pre-cancer, cancer, hyperproliferative diseases, vascular diseases such as atherosclerosis and restenosis, and diseases and conditions where the prevention of apoptosis is desired. A list of nonexhaustive examples of this includes extension of the subject's life by any period of time, a decrease in pain to the subject that can be attributed to the subject's condition, a decrease in the severity of the disease, an increase in the therapeutic effect of a therapeutic agent, an improvement in the prognosis of the condition or disease, a decrease in the amount or frequency of administration of a therapeutic agent, an alteration in the treatment regimen of the subject that reduces invasiveness of treatment, a decrease in the number of normal (non-cancerous) cells undergoing apoptosis so as to reduce injury to a tissue, an increase in the number of cells undergoing apoptosis when hyperproliferation is at least partially responsible for a condition or disease, and a decrease in the severity or frequency of side effects from a therapeutic agent. With respect to the treatment of cancer or precancer, therapeutic benefits also include a decrease or delay in the neoplastic development of the disease, decrease in hyperproliferation, reduction in tumor growth, delay of metastases, and reduction in cancer cell or tumor cell proliferation rate.

Cancer is a disease characterized by hyperproliferative cells, and thus, the methods and compositions of the invention apply to the treatment of patients with cancer or precancer. Cancers that may be treated include, but are not limited to, cancers of the bladder, blood, bone, bone marrow, brain, breast, colon, esophagus, gastrointestine, gums, head, kidney, liver, lung, nasopharynx, neck, ovary, prostate, skin, stomach, testis, tongue, or uterus. In some embodiments of the present invention, the hyperproliferative disease or condition being treated is atherosclerosis.

In some embodiments a Fortilin inhibitor is provided to the patient by an expression vector that includes a promoter operably linked to a nucleic acid sequence encoding the inhibitor. The expression vector may a viral vector and include viral sequences. Viral vectors may be derived from, but are not limited to, vaccinia virus, adenovirus, herpesvirus, retrovirus, cytomegalovirus, and adeno-associated virus. These embodiments may also be applied to Fortilin enhancers as well. Any method or composition described for the use with a Fortilin modulator may be employed for the use of another Fortilin modulator.

Administration of an expression vector to a patient to effect methods of the present invention may be accomplished by delivering it endoscopically, intravenously, intralesionally, percutaneously, or subcutaneously to the patient. In some embodiments, the treatment also includes administering a second, third, or fourth type of anti-cancer treatment. A variety of types of anti-cancer treatments may be employed, such as surgery, gene therapy, chemotherapy, radiotherapy, or immunotherapy, in addition to the Fortilin modulator. If chemotherapy is employed, a variety of chemotherapeutic agents may be implemented, including etoposide. Moreover, multiple administrations may be given to a patient. The second anti-cancer treatment may be administered before, after, or at the same time as the Fortilin or Fortilin modulator is administered to the patient.

In some cases, methods of inhibiting apoptosis in a cell are desirable. These may be accomplished by administering a Fortilin polypeptide in an amount effective to inhibit apoptosis in the cell. Such methods may include the administration of a Fortilin enhancer in an amount effective to increase Fortilin activity. Any composition or method discussed with respect to one method may be implemented with respect to other methods described in this disclosure. Thus, treatment methods described above may also include a Fortilin enhancer, particularly if the inhibition of apoptosis is desired in certain cells.

In some cases, inhibition of apoptosis in a cell involves providing to the cell an expression vector comprising a polynucleotide encoding a Fortilin polypeptide under the transcriptional control of a promoter, wherein expression of the Fortilin polypeptide is at a level effective to inhibit apoptosis in the cell. All or part of a Fortilin polypeptide may be supplied to the cell. In some embodiments, the encoded Fortilin polypeptide may include at least 20, 40, 60, 80, or 100 contiguous amino acids from SEQ ID NO:2 (human Fortilin amino acid sequence). Alternatively, the expression vector containing a polynucleotide may include at least 20, 40, 60, 80, or 100 contiguous nucleic acids from SEQ ID NO:1 (human Fortilin cDNA).

Screening methods are also contemplated to be part of the present invention. These include methods of identifying a modulator of a Fortilin polypeptide. In one embodiment, this method includes contacting the Fortilin polypeptide with a candidate substance and assaying whether the candidate substance modulates the Fortilin polypeptide. As described elsewhere, a modulator is a compound or substance that alters Fortilin activity, and it may enhance or inhibit Fortilin activity. A person of ordinary skill in the art would be familiar with a variety of ways to determine whether the candidate substance modulates the Fortilin polypeptide. In some embodiments of the present invention, assaying may be done by comparing the activity of the Fortilin polypeptide in the presence and absence of the candidate substance, by comparing the amount of the Fortilin polypeptide or mRNA in the presence or absence of the candidate substance, by determining whether the candidate substance specifically interacts with the Fortilin polypeptide, by determining whether a p53-Fortilin interaction is disrupted, or by determining whether an MCL1-Fortilin interaction is disrupted. A modulator that inhibits Fortilin may act, for example, by preventing it from binding to a compound it can bind to in the absence of the modulator. A modulator that enhances Fortilin activity may act, for example, by increasing Fortilin expression.

Diagnostic methods are also part of the present invention. Such diagnostic methods may be employed with any of the diseases or conditions discussed herein. Diagnosis of hyperproliferative conditions or diseases such as cancer are specifically contemplated. Methods of diagnosing cancer in a subject suspected of having cancer or of evaluating the prognosis of a cancer patient can be done by obtaining a sample from the subject and evaluating Fortilin in the sample. Evaluating Fortilin may involve assaying the amount of Fortilin polypeptide. An antibody that specifically binds Fortilin may be used to assay for Fortilin amounts. In other embodiments, Fortilin may be evaluated by evaluating the genomic DNA sequence encoding Fortilin or by evaluating the amount of mRNA encoding Fortilin.

In some cases, the prevention of apoptosis is desirable as a way of treating a condition or disease. This is particularly desirable when cells undergo apoptosis, which contributes to the negative effect of a disease or condition. Thus, other methods of the invention include a method of preventing apoptosis in a cell with steps that include administering to the cell an effective amount of an expression vector comprising a promoter operably linked to a nucleic acid sequence encoding Fortilin. In some embodiments, the cell does not undergo apoptosis mediated by p53. The cell may be any cell type, specifically including a muscle cell, such as a myocyte, or a neuronal cell. Methods of preventing apoptosis may be utilized for treating a patient with a spinal cord injury or a patient with myocarditis or acute myocardial infarction comprising administering to the subject an effective amount Fortilin, wherein a therapeutic benefit is conferred to the subject. In some embodiments, muscle atrophy is treated or prevented in a subject by administering to the subject an effective amount of Fortilin to inhibit apoptosis in a muscle cell. It is specifically contemplated that all or part of a Fortilin polypeptide can be provided to a cell in an effective amount to inhibit apoptosis of the cell. For example, a portion of a Fortilin polypeptide that includes the MCL1 binding region may be implemented, such as amino acids 5-22 in SEQ ID NO:2. In some embodiments, a Fortilin polypeptide is provided to the cell by expression of an effective amount of Fortilin from an expression construct that expresses Fortilin.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1A:
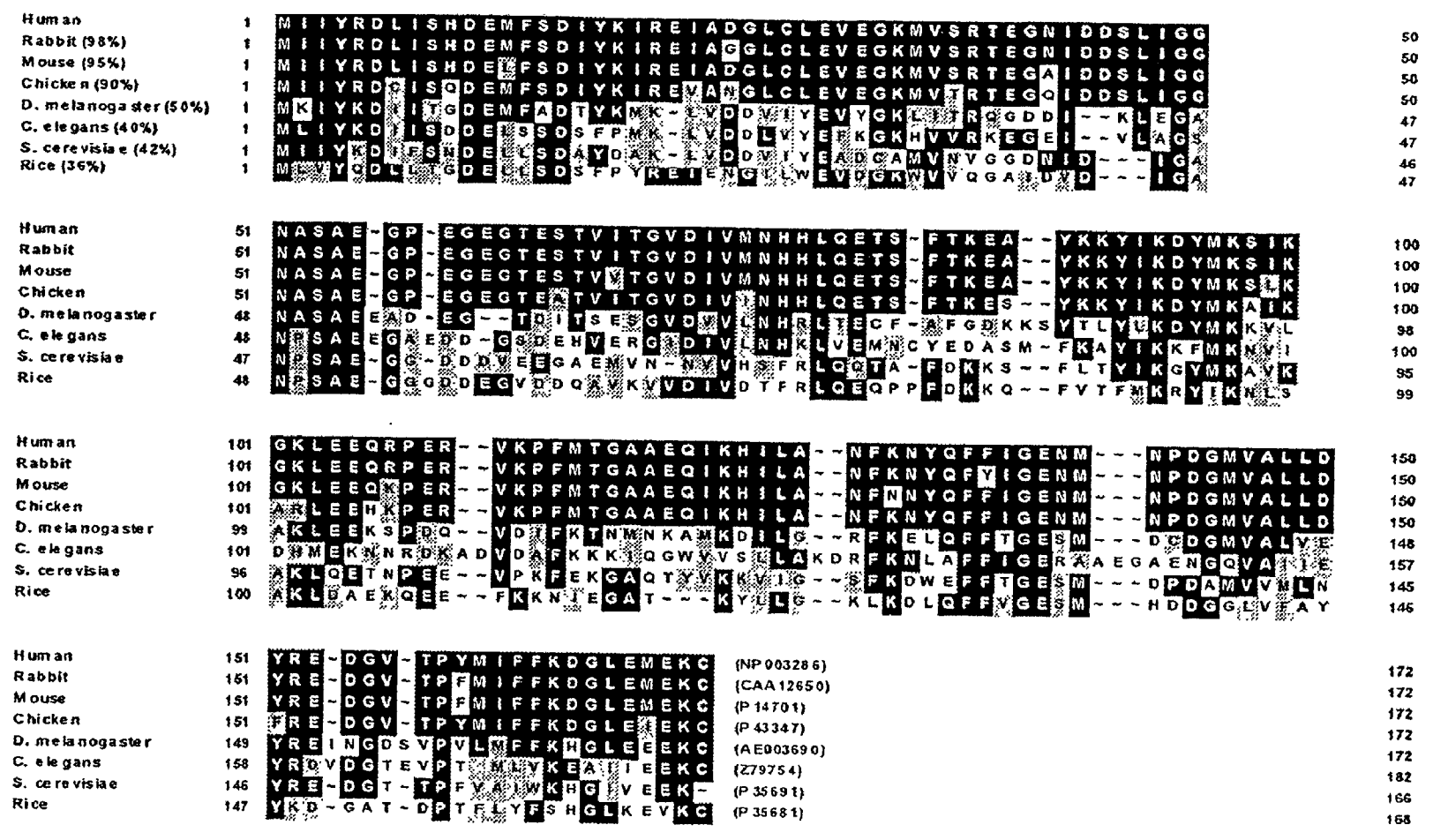

FIG. 1A, 1B, 1C. The Sequence and the Message of Fortilin. FIG. 1A. The amino acid sequence of human Fortilin (SEQ ID NO:2) was aligned to those of rabbit (SEQ ID NO:3), mouse (SEQ ID NO:4), chicken (SEQ ID NO:5), *Drosophila melanogaster* (*D. melanogaster*) (SEQ ID NO:6), *Caenorhabditis elegans* (*C. elegans*) (SEQ ID NO:7), *Saccharomyces cerevisiae* (*S. cerevisiae*) (SEQ ID NO:8) and rice (SEQ ID NO:9), using a sequence analysis program. Black and gray boxes represent amino acids that are identical and homologous to those of human Fortilin, respectively. The numbers within parentheses indicate GenBank accession numbers. FIG. 1B. The amino acid sequence of Fortilin was evaluated for its hydrophilicity. A peptide representing the $90^{th}$-$111^{th}$ amino acids of Fortilin was used to raise antibody against Fortilin in rabbits. FIG. 1C. Northern hybridization was carried out on multiple tissue blots of adult human mRNA using a Fortilin cDNA probe. The β-actin cDNA probe was used to evaluate the amount of mRNA loaded in each lane. The Fortilin message was present ubiquitously in various human tissues, especially in the liver, kidney, small intestine, skeletal muscle, and testis.

FIG. 1A. HeLa cells were transfected in duplicate with either pFLAG-Bcl-xL, pFLAG-MCL1, pFLAG-Fortilin, or pFLAG-LacZ, challenged with Etoposide, and then stained for the FLAG epitope using anti-FLAG antibody and anti-mouse IgG conjugated to Rhodamine Red X. The nuclei were stained with DAPI. The ectopic overexpression of Bcl-xL, MCL1, and Fortilin prevented HeLa cells from undergoing Etoposide-induced apoptosis in a statistically significant fashion. FIG. 2B. HeLa cells were transfected with a various amount of pFLAG-Fortilin and pFLAG-LacZ and subjected to the same procedures as in FIG. 2A. A larger amount of pFLAG-Fortilin introduced into cells was associated with statistically significantly lower apoptotic indices (p<0.05; ANOVA).

FIG. 6A. Non-small cell lung cancer cell line H1299 cells were transfected with p53-pcDNA3, LacZ-pFLAG, p-Bax-RE-Luc (a plasmid encoding the Luciferase gene under the control of the Bax responsive element) and pFLAG vector encoding Bcl-2, MCL1, Fortilin or Fortilin mutant as indicated in the figure. MCL1, Fortilin, and truncated Fortilin (23-172) inhibited p53 transactivation of the Bax gene. FIG. 6B. H1299 cells were transfected with p53-pcDNA3, LacZ-pFLAG, p-Bax-RE-Luc, and various amount of Fortilin-pFLAG. Transfection with larger amounts of Fortilin was associated with stronger inhibitory effects on p53 transactivation of the Bax gene, indicating the response is dosage-dependent.

FIG. 10A. Approximately $2 \times 10^6$ U2OS stable transfectants, either expressing fortilin ("F") or harboring empty expression vectors ("C"), were challenged either with DMSO (vehicle; "−") or with etoposide ("+") at a final concentration of 10 μg/mL for 48 hours. Caspase 3-like activity was then determined by the amount of 7-amido-4-(trifluoromethyl)coumarin (AFC) released, after two-hour incubation at 37° C., by Fluoroskan system (Thermo-Labsystems, Helsinki, Finland) set at an excitation value of 355 nm and emission value of 525 nm. The results ("AFC") were expressed as relative fluorescence unit (R.F.U.) per microgram of protein (R.F.U./μg protein). Baseline caspase-3-like activities were not different between control and fortilin-expressing cells ("NS", not statistically different). Upon etoposide challenge, fortilin significantly inhibited the caspase-3-like activity in U2OS cells (asterisk, P<0.05). FIG. 10B. Kinetics of caspase-3 like activities in control and fortilin-overexpressing cells. Approximately $2 \times 10^6$ U2OS, either expressing fortilin ("F") or harboring empty expression vectors ("C"), were challenged with 10 μg/mL of etoposide and subjected to the assay of caspase-3 like activity as described above. The fluorescence signals were measured every 10 minutes for 2 hours. Fortilin significantly inhibited the caspase-3-like activity in U2OS cells at all time points (P<0.05).

DESCRIPTION OF ILLUSTRATIVE EMBODIMENTS

Figures 1B, 1C:
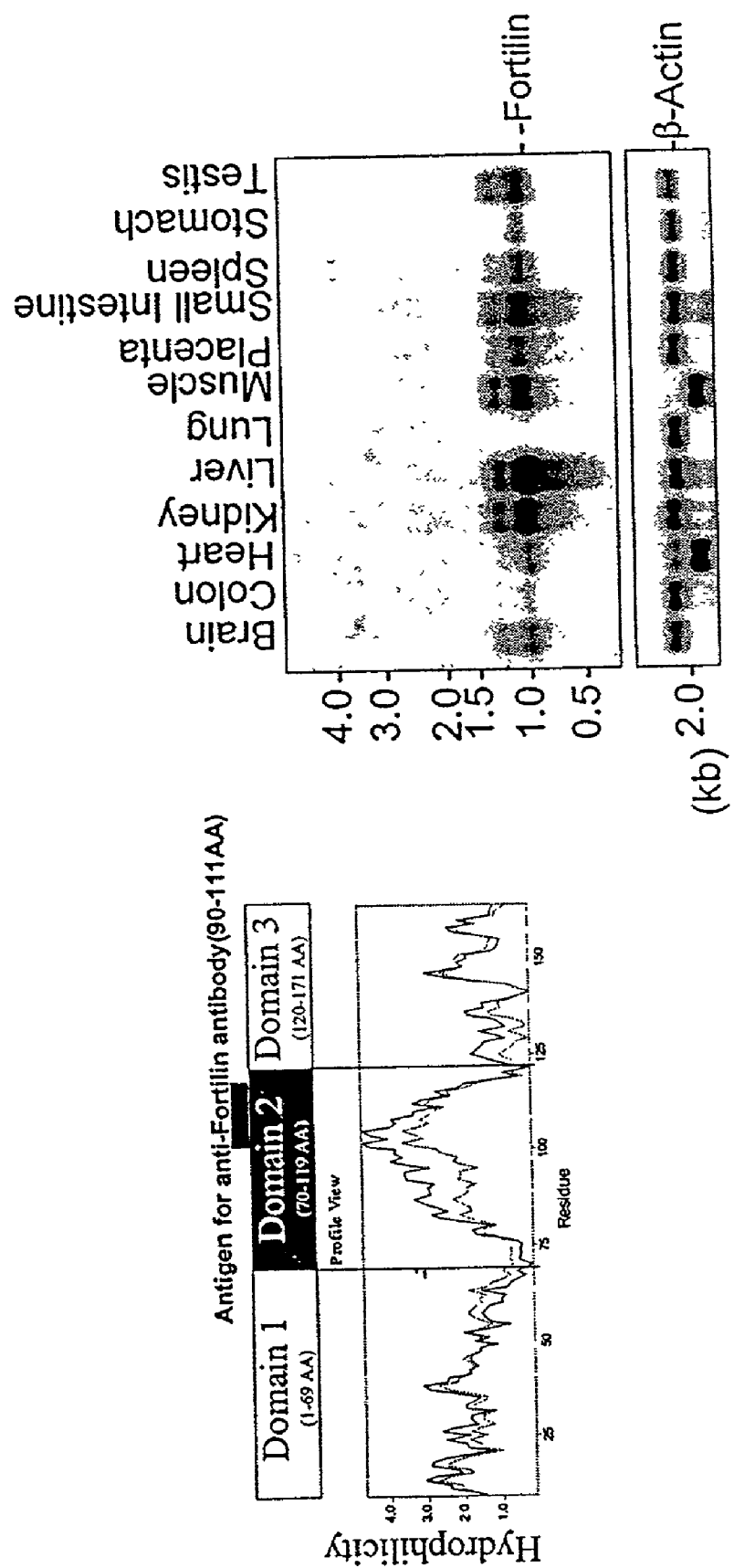

The present invention is based on the characterization of a role for the Fortilin (also known as Translationally Controlled Tumor Protein (TCTP), encoded by the TPT1 gene) polypeptide in apoptosis, which carries ramifications particularly with respect to the diagnosis and treatment of hyperproliferative diseases and conditions, such as cancer and atherosclerosis. A hyperproliferative disease or condition is characterized by hyperproliferative cells, i.e., cells associated with any sort of abnormal growth regulation. Hyperproliferative diseases and conditions include all forms of cancer, restenosis, multi-drug resistant cancer, primary psoriasis and metastatic tumors, angiogenesis, rheumatoid arthritis, inflammatory bowel disease, psoriasis, eczema, and secondary cataracts, as well as oral hairy leukoplasia, bronchial dysplasia, carcinomas in situ, and intraepithelial hyperplasia.

I. Fortilin

The present invention concerns compositions and methods involving Fortilin and Fortilin modulators. Fortilin is a polypeptide also known as Translationally Controlled Tumor Protein (TCTP). TCTP was identified as a human homologue to the mouse p21 protein, which was originally identified from a mouse L cell library (Chitpatima et al., 1988; Gross et al., 1989). The mouse L cell line was established from normal mouse subcutaneous connective tissue (Sanford, 1948). Since then, there has been little evidence that the expression of this protein is translationally controlled. The function of this protein had not been previously elucidated. Herein, based on observations that TCTP functions as an anti-apoptotic protein, it is now designated Fortilin (Fortis=strong, robust, in Latin). The terms "TCTP" and "Fortilin" are used interchangeably herein, both referring to the amino acid sequence corresponding to GenBank accession number X16064 (cognate nucleic acid sequence also disclosed).

The fortilin cDNA encodes for a 172 amino acid polypeptide with no significant homology to any known proteins described previously, in part or as a whole. The degree of conservation is unusually high in Fortilin: human and mouse Bcl-2 are 72% identical while human and mouse Fortilin are 95% identical. Fortilin does not contain typical nuclear localization signals (NLS), (Nigg, 1997) a hydrophobic transmembrane anchor, or signal sequence. Overall, Fortilin is a hydrophilic protein with the central portion (designated Domain 2) being most hydrophilic.

Fortilin is ubiquitously expressed in normal human tissue. Two transcripts have been identified, whose 3' untranslated regions differ in length. (Thiele et al., 2000). The wide tissue distribution of Fortilin indicates that it may be important in the maintenance of basic cellular functions. It has been postulated to be a housekeeping gene. (Chung et al., 2000). The presence of weaker band at 1.2 kilobase pairs, just above the Fortilin 1.0 kilobase pair band, may represent the message of a Fortilin-like molecule that remains unidentified. As described herein, Fortilin specifically binds the p53 protein and the MCL1 protein. It also prevents a cell from undergoing apoptosis and can contribute to the development of atherosclerosis. Thus, Fortilin can be provided to a cell to inhibit the involution of apoptosis. Alternatively, modulators of Fortilin that disrupt its ability to bind p53 or MCL1 may effect an anti-hyperproliferative cell therapy. Furthermore, in some embodiments of the invention, disruption of a Fortilin interaction increases the efficacy of chemotherapy on a cancerous cell. Diagnostic methods to evaluate Fortilin status are also contemplated to evaluate predisposition, development, and prognosis relating to hyperproliferative disorders such as cancer and atherosclerosis.

Hyperproliferative disorders such as cancers may further involve angiogenesis. Angiogenesis, the process by which new blood vessels are formed, is essential for normal body activities including reproduction, development and wound repair. Although the process has not been completely elucidated, it is believed to involve a complex interaction of molecules which regulate the growth of endothelial cells (the primary cells of capillary blood vessels). Under normal conditions, these molecules appear to maintain the microvasculature in a quiescent state (i.e. one of no capillary growth) for prolonged periods. Under certain conditions such as during wound repair, endothelial cells can undergo rapid proliferation and turnover within a week (Folkman and Shing, 1987; Folkman and Klagsbrun, 1987). Angiogenesis is important in two stages of tumor metastasis. In the first stage, angiogenesis stimulation is important in the vascularization of the tumor which allows tumor cells to enter the bloodstream and to circulate throughout the body. After the tumor cells have left the primary site, and have settled into the secondary metastasis site, angiogenesis must occur before the new tumor can grow and expand. Therefore, prevention of angiogenesis could lead to the prevention of metastasis of tumors and possibly contain the neoplastic growth at the primary site. Fortilin, which is highly expressed in cancerous cells and tissues with a greater propensity to malignancy, may contribute to angiogenesis and hence tumorigenesis by abrogating apoptosis. This modulator of Fortilin may be implemented in methods described herein to effect therapeutic, preventative or prognostic benefits.

On the other hand, inactivation of apoptosis also has benefits. Cells that die by apoptosis include neurons (e.g., during the course of neurodegenerative diseases such as stroke, Parkinson's disease, and Alzheimer's disease), cardiomyocytes (e.g., after myocardial infarction or over the course of congestive heart failure), and normal cells (e.g., after exposure to radiation or chemotherapeutic agents). Additionally, environmental stress (e.g., hypoxic stress) that is not alleviated may cause a cell to enter the early phase of the apoptotic pathway, which is reversible (i.e., cells at the early stage of the apoptotic pathway can be rescued). Fortilin may therefore be used in the treatment of diseases that are thought to be mediated by promotion of apoptosis, such as viral diseases, neurodegenerative diseases, myelodysplasia, ischemic diseases and hepatic diseases.

Particular conditions in which Fortilin may be utilized include heart attacks or strokes. Heart attack is typically characterized by apoptotic cardiac cell death therefore, Fortilin can be used to mitigate or prevent this type of cell death and protect against the consequences of this condition. In addition, Fortilin could also be used to inhibit tissue damage evident in chemotherapy-induced cardiac tissue damage, or in stroke-induced tissue damage or even in kidney failure. The use of Fortilin would be particularly advantageous where an individual has a history of heart attacks or strokes or even belongs to a family having such a history.

Additionally, chemotherapy and radiotherapy also induce other forms of tissue damage and therefore it follows that co-administration or sequential administration of chemotherapy or radiotherapy with an anti-apoptotic factor such as Fortilin may be used in order to prevent widespread damage.

In addition, premature and widespread apoptosis has been implicated in much of the damage associated with acquired immune deficiency syndrome (AIDS). It is thought that apoptosis may be a principal cause of death in uninfected T cells in AIDS patients, leading ultimately to the suppression of the patient's immune system. Thus, factors such as Fortilin can inhibit this form of cell death thereby preventing the damage that the AIDS virus causes in uninfected cells. Therefore, it is advantageous to block apoptosis and the ensuing depletion of T cells using Fortilin and maintain T cell function and viability in HIV infected individuals thus maintaining the cellular immune response.

Apoptosis is an ongoing process in both the developing and the mature nervous system. In the developing nervous system, neurons undergo apoptosis unless they receive an adequate supply of neurotrophic substances from the target (for example, the muscle) that they innervate. In the mature nervous system, apoptosis occurs in the course of neurodegenerative diseases, such as Alzheimer's and Parkinson's Diseases, which progress slowly over long periods of time, and in acute neurological insults, such as a stroke. Factors such as Fortilin may further be utilized, as an effective treatment for neurodegenerative diseases and stroke by preventing neuronal apoptosis; and may further be used in conjunction with neurotrophic substances to enhance inhibition of neuronal cell death.

Other applications of Fortilin may include basal layer epidermal melanocytes and keratinocytes which undergo characteristic programmed cell death in response to injury. Types of injury includes injury due to exposure to ultraviolet light, especially UVB, for example, in habitually sun-exposed skin, and injury due to the normal aging process. Fortilin may therefore control, or inhibit, melanocyte and keratinocyte cell death by altering the effects of apoptosis.

Fortilin may also proved beneficial in increasing the efficiency of transfection of cells by inhibiting cell death. Transfection of cells is routinely used as a genetic engineering tool and involves the introduction of a foreign gene(s) into a target cell. Transfection methods can be useful in the areas of medicine, agriculture, pharmaceuticals, and biomedical research. Gene therapy, involves the application of transfection wherein a foreign gene can be stably incorporated into a patient's genome thereby conferring upon the transfected cell, the ability to produce the product of the transfected gene. Fortilin therefore may enhance the stability and production of the transfected gene(s) by inhibiting apoptosis.

A. Proteinaceous Compositions

In certain embodiments, the present invention concerns novel compositions comprising at least one proteinaceous molecule, such as Fortilin or a modulator of Fortilin, such as an antibody against the polypeptide or a peptide that comprises the region of a binding partner that binds Fortilin. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

| Modified and Unusual Amino Acids | |
|---|---|
| Abbr. | Amino Acid |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |

TABLE 1-continued

| Modified and Unusual Amino Acids | |
|---|---|
| Abbr. | Amino Acid |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases available on the World Wide Web at ncbi.nlm.nih.gov). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody, for example, an antibody against Fortilin. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow et al., 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

1. Functional Aspects

When the present application refers to the function or activity of Fortilin, it is meant that the molecule in question has the ability to bind p53 or MCL1. Other phenotypes that may be considered to be associated with the normal Fortilin gene product are the ability to prevent etoposide-induced apoptosis, to prevent p53-mediated apoptosis, to prevent transactivation by p53, or to prevent Bax-mediated apoptosis, or the ability to promote transformation of a cell from a normally regulated state of proliferation to a malignant state, i.e., one associated with any sort of abnormal growth regulation, or to promote the transformation of a cell from an abnormal state to a highly malignant state, e.g., to promote metastasis or invasive tumor growth, or to have an effect on angiogenesis, adhesion, migration, cell-to-cell signaling, cell growth, cell proliferation, density-dependent growth, anchorage-dependent growth and others, or to be involved in the development of hyperproliferative diseases or conditions. Determination of which molecules possess this activity may be achieved using assays familiar to those of skill in the art. For example, transfer of genes encoding products that inhibit or modulate Fortilin, or variants thereof, into cells that have a functional Fortilin product—and hence exhibit the lower rates of apoptosis—will identify, by virtue of an increased level of apoptosis, those molecules having a Fortilin modulator or inhibitor function. An endogenous Fortilin polypeptide refers to the polypeptide encoded by the cell's genomic DNA.

On the other hand, when the present invention refers to the function or activity of a "Fortilin modulator," one of ordinary skill in the art would further understand that this includes, for example, the ability to specifically or competitively bind Fortilin or an ability to reduce or inhibit its activity, such as reduce its ability to bind p53 or MCL1. Thus, it is specifically contemplated that a Fortilin modulator may be a molecule that affects Fortilin expression, such as by binding a Fortilin-encoding transcript. Determination of which molecules are suitable modulators of Fortilin may be achieved using assays familiar to those of skill in the art—some of which are disclosed herein—and may include, for example, the use of native and/or recombinant Fortilin.

2. Variants of Fortilin and Fortilin Modulators

Amino acid sequence variants of the polypeptides of the present invention can be substitutional, insertional or deletion variants. Deletion variants lack one or more residues of the native protein that are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a Fortilin polypeptide or a modulator of a Fortilin provided the biological activity of the protein is maintained.

The term "functionally equivalent codon" is used herein to refer to codons that encode the same amino acid, such as the six codons for arginine or serine, and also refers to codons that encode biologically equivalent amino acids (see Table 2, below).

TABLE 2

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 2 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of Fortilin or a Fortilin modulator, but with altered and even improved characteristics.

3. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

4. Protein Purification

It may be desirable to purify Fortilin, a Fortilin modulator, or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g, alter pH, ionic strength, and temperature).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

5. Antibodies

Another embodiment of the present invention are antibodies, in some cases, a human monoclonal antibody immunoreactive with the polypeptide sequence of Fortilin (SEQ ID NO:2). It is understood that antibodies can be used for inhibiting or modulating Fortilin. It is also understood that this antibody is useful for screening samples from human patients for the purpose of detecting Fortilin present in the samples. The antibody also may be useful in the screening of expressed DNA segments or peptides and proteins for the discovery of related antigenic sequences. In addition, the antibody may be useful in passive immunotherapy for cancer. All such uses of the said antibody and any antigens or epitopic sequences so discovered fall within the scope of the present invention.

a. Antibody Generation

In certain embodiments, the present invention involves antibodies. For example, all or part of a monoclonal, single chain, or humanized antibody may function as a modulator of Fortilin. Other aspects of the invention involve administering antibodies as a form of treatment or as a diagnostic to identify or quantify a particular polypeptide, such as Fortilin. As detailed above, in addition to antibodies generated against full length proteins, antibodies also may be generated in response to smaller constructs comprising epitopic core regions, including wild-type and mutant epitopes.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (mAbs) are recognized to have certain advantages, e.g., reproducibility and large-scale production, and their use is generally preferred. The invention thus provides monoclonal antibodies of the human, murine, monkey, rat, hamster, rabbit and even chicken origin.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow and Lane, "Antibodies: A Laboratory Manual," Cold Spring Harbor Laboratory, 1988; incorporated herein by reference).

The methods for generating monoclonal antibodies (mAbs) generally begin along the same lines as those for preparing polyclonal antibodies. Briefly, a polyclonal antibody may be prepared by immunizing an animal with an immunogenic polypeptide composition in accordance with the present invention and collecting antisera from that immunized animal. Alternatively, in some embodiments of the present invention, serum is collected from persons who may have been exposed to a particular antigen. Exposure to a particular antigen may occur a work environment, such that those persons have been occupationally exposed to a particular antigen and have developed polyclonal antibodies to a peptide, polypeptide, or protein. In some embodiments of the invention polyclonal serum from occupationally exposed persons is used to identify antigenic regions in the gelonin toxin through the use of immunodetection methods.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As also well known in the art, the immunogenicity of a particular immunogen composition can be enhanced by the use of non-specific stimulators of the immune response, known as adjuvants. Suitable molecule adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection also may be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide, peptide or domain, be it a wild-type or mutant composition. The immunizing composition is administered in a manner effective to stimulate antibody producing cells.

mAbs may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate mAbs. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 10$^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. Such antibodies are generally useful for in vivo therapeutic applications. This strategy reduces the host response to the foreign antibody and allows selection of the human effector functions.

"Humanized" antibodies are also contemplated, as are chimeric antibodies from mouse, rat, or other species, bearing human constant and/or variable region domains, bispecific antibodies, recombinant and engineered antibodies and fragments thereof. The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope. Examples of other teachings in this area include U.S. Pat. Nos. 6,054,297; 5,861,155; and 6,020,192, all specifically incorporated by reference. Methods for the development of antibodies that are "custom-tailored" to the patient's disease are likewise known and such custom-tailored antibodies are also contemplated.

b. Fortilin Antigenic Sequences

As another way of effecting modulation of Fortilin in a subject, peptides corresponding to one or more antigenic determinants of the Fortilin polypeptides of the present invention also can be prepared so that an immune response against Fortilin is raised. Thus, it is contemplated that vaccination with a Fortilin peptide or polypeptide may generate an autoimmune response in an immunized animal such that autoantibodies that specifically recognize the animal's endogenous Fortilin protein. This vaccination technology is shown in U.S. Pat. Nos. 6,027,727; 5,785,970, and 5,609,870, which are hereby incorporated by reference.

Such peptides should generally be at least five or six amino acid residues in length and will preferably be about 10, 11, 12, 13, 14, 15, 16, 17, 18, 19, 20, 25 or about 30 amino acid residues in length, and may contain up to about 35-50 residues. For example, these peptides may comprise a Fortilin amino acid sequence, such as 5, 6, 7, 8, 9, 10, 11, 12, 13, 14, 15, 16, 17, 18, 19, 20, 21, 22, 23, 24, 25, 30, 35, 40, 45, and 50 or more contiguous amino acids from SEQ ID NO:2. Synthetic peptides will generally be about 35 residues long, which is the approximate upper length limit of automated peptide synthesis machines, such as those available from Applied Biosystems (Foster City, Calif.). Longer peptides also may be prepared, e.g., by recombinant means.

U.S. Pat. No. 4,554,101, incorporated herein by reference, teaches the identification and preparation of epitopes from primary amino acid sequences on the basis of hydrophilicity. Through the methods disclosed in Hopp, one of skill in the art would be able to identify epitopes from within an amino acid sequence such as the Fortilin sequence disclosed herein in SEQ ID NO: 2.

Numerous scientific publications have also been devoted to the prediction of secondary structure, and to the identification of epitopes, from analyses of amino acid sequences (Chou & Fasman, 1974a, b; 1978a, b; 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1988; Wolf et al., 1988), the program PepPlot® (Brutlag et al., 1990; Weinberger et al., 1985), and other new programs for protein tertiary structure prediction (Fetrow & Bryant, 1993).

Another commercially available software program capable of carrying out such analyses is MacVector (IBI, New Haven, Conn.).

In further embodiments, major antigenic determinants of a Fortilin polypeptide may be identified by an empirical approach in which portions of the gene encoding the Fortilin polypeptide are expressed in a recombinant host, and the resulting proteins tested for their ability to elicit an immune response. For example, PCR™ can be used to prepare a range of peptides lacking successively longer fragments of the C-terminus of the protein. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Another method for determining the major antigenic determinants of a polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. The antigenic determinants of the peptides which are initially identified can be further localized by performing subsequent syntheses of smaller peptides with larger overlaps, and by eventually replacing individual amino acids at each position along the immunoreactive peptide.

Once one or more such analyses are completed, polypeptides are prepared that contain at least the essential features of one or more antigenic determinants. The peptides are then employed in the generation of antisera against the polypeptide. Minigenes or gene fusions encoding these determinants also can be constructed and inserted into expression vectors by standard methods, for example, using PCR™ cloning methodology.

The use of such small peptides for antibody generation or vaccination typically requires conjugation of the peptide to an immunogenic carrier protein, such as hepatitis B surface antigen, keyhole limpet hemocyanin or bovine serum albumin, or other adjuvants discussed above (adjuvenated peptide). Alum is an adjuvant that has proven sufficiently non-toxic for use in humans. Methods for performing this conjugation are well known in the art. Other immunopotentiating compounds are also contemplated for use with the compositions of the invention such as polysaccharides, including chitosan, which is described in U.S. Pat. No. 5,980,912, hereby incorporated by reference. Multiple (more than one) Fortilin epitopes may be crosslinked to one another (e.g., polymerized). Alternatively, a nucleic acid sequence encoding an Fortilin peptide or polypeptide may be combined with a nucleic acid sequence that heightens the immune response. Such fusion proteins may comprise part or all of a foreign (non-self) protein such as bacterial sequences, for example.

Antibody titers effective to achieve a response against endogenous Fortilin will vary with the species of the vaccinated animal, as well as with the sequence of the administered peptide. However, effective titers may be readily determined, for example, by testing a panel of animals with varying doses of the specific antigen and measuring the induced titers of autoantibodies (or anti-self antibodies) by known techniques, such as ELISA assays, and then correlating the titers with Fortilin-related cancer characteristics, e.g., tumor growth or size.

One of ordinary skill would know various assays to determine whether an immune response against Fortilin was generated. The phrase "immune response" includes both cellular and humoral immune responses. Various B lymphocyte and T lymphocyte assays are well known, such as ELISAs, cytotoxic T lymphocyte (CTL) assays, such as chromium release assays, proliferation assays using peripheral blood lymphocytes (PBL), tetramer assays, and cytokine production assays. See Benjamini et al., 1991, hereby incorporated by reference.

6. Immunodetection Methods

As discussed, in some embodiments, the present invention concerns immunodetection methods for binding, purifying, removing, quantifying and/or otherwise detecting biological components such as antigenic regions on polypeptides and peptides. The immunodetection methods of the present invention can be used to identify antigenic regions of a peptide, polypeptide, or protein that has therapeutic implications, particularly in reducing the immunogenicity or antigenicity of the peptide, polypeptide, or protein in a target subject.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate.

With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with antibodies. After binding and/or washing to remove non-specifically bound immune complexes, the bound anti-antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

b. Immunohistochemistry

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize Fortilin or to evaluate the amount Fortilin in a cell. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 mg of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

7. Lipid Components and Moieties

In certain embodiments, the present invention concerns compositions comprising one or more lipids associated with a nucleic acid, an amino acid molecule, such as a peptide, or another small molecule compound. In any of the embodiments discussed herein, the molecule may be either Fortilin or a Fortilin modulator, for example a nucleic acid encoding all or part of either Fortilin or a Fortilin modulator, or alternatively, an amino acid molecule encoding all or part of Fortilin modulator. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

a. Lipid Types

A neutral fat may comprise a glycerol and/or a fatty acid. A typical glycerol is a three carbon alcohol. A fatty acid generally is a molecule comprising a carbon chain with an acidic moiety (e.g., carboxylic acid) at an end of the chain. The carbon chain may of a fatty acid may be of any length, however, it is preferred that the length of the carbon chain be of from at least 2, 3, 4, 5, 6, 7, 8, 9, 10, 11, 12, 13, 14, 15, 16, 17, 18, 19, 20, 21, 22, 23, 24, 25, 26, 27, 28, 29, to 30 or more carbon atoms, and any range derivable therein. An example of a range is from about 8 to about 16 carbon atoms in the chain portion of the fatty acid. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated. The fatty acid may be branched, though in embodiments of the present invention, it is unbranched.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phoshotidyl serine, a phosphatidyl ethanolamine, a phosphatidyl choline, a phosphatidyl glycerol or a phosphotidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

b. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

c. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

d. Lipid Composition Structures

A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/Fortilin modulator-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-Fortilin modulator or Superfect (Qiagen)-Fortilin modulator complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

i. Emulsions

A lipid may be comprised in an emulsion. A lipid emulsion is a substantially permanent heterogeneous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

ii. Micelles

A lipid may be comprised in a micelle. A micelles is a cluster or aggregate of lipid compounds, generally in the form of a lipid monolayer, may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

e. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In specific aspects, a lipid and/or Fortilin modulator may be, for example, encapsulated in the aqueous interior of a liposome, interspersed within the lipid bilayer of a liposome, attached to a liposome via a linking molecule that is associated with both the liposome and the Fortilin modulator, entrapped in a liposome, complexed with a liposome, etc.

i. Making Liposomes

A liposome used according to the present invention can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the Fortilin modulator, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the Fortilin modulator is about 0.7 to about 1.0 µm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster, 1983; Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of modulatory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/Fortilin modulator or liposomes only of appropriate and uniform size, which are structurally stable and produce maximal activity. Such techniques are well-known to those of skill in the art (see, for example Martin, 1990).

Once manufactured, lipid structures can be used to encapsulate compounds that are toxic (e.g., chemotherapeutics) or labile (e.g., nucleic acids) when in circulation. Liposomal encapsulation has resulted in a lower toxicity and a longer serum half-life for such compounds (Gabizon et al., 1990).

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

ii. Liposome Targeting

Although targetting may be achieved by employing a particular peptide sequence, association of the Fortilin modulator with a liposome may also improve biodistribution and other properties of the Fortilin modulator. For example, liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/Fortilin modulator composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of Fortilin modulator. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

5. Biochemical Cross-Linkers

In some embodiments of the invention, Fortilin or Fortilin modulators are covalently bonded to other compounds, including polypeptides. It can be considered as a general guideline that any biochemical cross-linker that is appropriate for use in an immunotoxin will also be of use in the present context, and additional linkers may also be considered to join proteinaceous compositions that include peptides and polypeptides of the present invention.

Cross-linking reagents are used to form molecular bridges that tie together functional groups of two different molecules, e.g., a stablizing and coagulating agent. To link two different proteins in a step-wise manner, hetero-bifunctional cross-linkers can be used that eliminate unwanted homopolymer formation. Examples of such cross-linkers can be found in Table 3.

TABLE 3

Hetero-Bifunctional Cross-Linkers

| linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It can therefore be seen that a targeted peptide composition will generally have, or be derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking. For a general overview of linking technology, one may wish to refer to Ghose & Blair (1987).

The spacer arm between the two reactive groups of a cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagents for use in immunotoxins is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the bispecific coagulating ligands of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art.

Once conjugated, the peptide generally will be purified to separate the conjugate from unconjugated targeting agents or coagulants and from other contaminants. A large number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

In addition to chemical conjugation, a Fortilin modulator or Fortilin polypeptide, peptide, or antibody may be modified at the protein level. Included within the scope of the invention are IgA protein fragments or other derivatives or analogs that are differentially modified during or after translation, for example by glycosylation, acetylation, phosphorylation, amidation, derivatization by known protecting/blocking groups, and proteolytic cleavage. Any number of chemical modifications may be carried out by known techniques, including but not limited to specific chemical cleavage by cyanogen bromide, trypsin, chymotrypsin, papain, V8 protease, $NaBH_4$; acetylation, formylation, farnesylation, oxidation, reduction; metabolic synthesis in the presence of tunicamycin.

II. Nucleic Acid Molecules

A. Polynucleotides Encoding Native Proteins or Modified Proteins

The present invention concerns polynucleotides, isolatable from cells, that are free from total genomic DNA and that are capable of expressing all or part of a protein or polypeptide. The polynucleotide may encode a peptide or polypeptide containing all or part of the Fortilin amino acid sequence or may encode a peptide or polypeptide having all or part of the amino acid sequence of a Fortilin modulator. Recombinant proteins can be purified from expressing cells to yield active proteins.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "Fortilin polynucleotide" refers to a Fortilin-encoding nucleic acid molecule that has been isolated free of total genomic nucleic acid. Therefore, a "polynucleotide encoding Fortilin" refers to a DNA segment that contains wild-type (SEQ ID NO:1), mutant, or polymorphic Fortilin polypeptide-coding sequences isolated away from, or purified free from, total mammalian or human genomic DNA. Therefore, for example, when the present application refers to the function or activity of Fortilin or a "Fortilin polypeptide," it is meant that the polynucleotide encodes a molecule that has the activity of Fortilin.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular polypeptide from a given species may be represented by natural variants that have slightly different nucleic acid sequences but, nonetheless, encode the same protein (see Table 2 above).

Similarly, a polynucleotide comprising an isolated or purified wild-type, polymorphic, or mutant polypeptide gene refers to a DNA segment including wild-type, polymorphic, or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

In particular embodiments, the invention concerns isolated DNA segments and recombinant vectors incorporating DNA sequences that encode a wild-type, polymorphic, or mutant Fortilin or Fortilin modulator polypeptide or peptide that includes within its amino acid sequence a contiguous amino acid sequence in accordance with, or essentially corresponding to a native polypeptide. Thus, an isolated DNA segment or vector containing a DNA segment may encode, for example, a Fortilin modulator that can inhibit or reduce Fortilin activity. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated Fortilin polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targetting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to the a particular gene, such as the human Fortilin gene (SEQ ID NO:1). A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides, for example, a modified gelonin toxin. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

The sequence of a Fortilin polypeptide will substantially correspond to a contiguous portion of that shown in SEQ ID NO:2, and have relatively few amino acids that are not identical to, or a biologically functional equivalent of, the amino acids shown in SEQ ID NO:2. The term "biologically functional equivalent" is well understood in the art and is further defined in detail herein.

Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 will be sequences that are "essentially as set forth in SEQ ID NO:2."

In certain other embodiments, the invention concerns isolated DNA segments and recombinant vectors that include within their sequence a contiguous nucleic acid sequence from that shown in SEQ ID NO:1. This definition is used in the same sense as described above and means that the nucleic acid sequence substantially corresponds to a contiguous portion of that shown in SEQ ID NO:1 and has relatively few codons that are not identical, or functionally equivalent, to the codons of SEQ ID NO:1. The term "functionally equivalent codon" is used herein to refer to codons that encode the same amino acid, such as the six codons for arginine or serine, and also refers to codons that encode biologically equivalent amino acids. See Table 4 below, which lists the codons preferred for use in humans, with the codons listed in decreasing order of preference from left to right in the table (Wada et al., 1990). Codon preferences for other organisms also are well known to those of skill in the art (Wada et al., 1990, included herein in its entirety by reference).

TABLE 4

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

The various probes and primers designed around the nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It also will be understood that this invention is not limited to the particular nucleic acid and amino acid sequences of SEQ ID NO:1 and SEQ ID NO:2. Recombinant vectors and isolated DNA segments may therefore variously include the Fortilin-coding regions themselves, coding regions bearing selected alterations or modifications in the basic coding region, or they may encode larger polypeptides that nevertheless include Fortilin-coding regions or may encode biologically functional equivalent proteins or peptides that have variant amino acids sequences.

The DNA segments of the present invention encompass biologically functional equivalent Fortilin proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

If desired, one also may prepare fusion proteins and peptides, e.g., where the Fortilin- or Fortilin modulator-coding regions are aligned within the same expression unit with other proteins or peptides having desired functions, such as for purification or immunodetection purposes (e.g., proteins that may be purified by affinity chromatography and enzyme label coding regions, respectively).

Encompassed by certain embodiments of the present invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length sequences set forth in SEQ ID NO:2, or to specific fragments of SEQ ID NO:1 that correspond to differences as compared to the published sequence for Fortilin.

1. Vectors

Native and modified polypeptides may be encoded by a nucleic acid molecule comprised in a vector. The term "vector" is used to refer to a carrier nucleic acid molecule into which a nucleic acid sequence ban be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausubel et al., 1996, both incorporated herein by reference. In addition to encoding a modified polypeptide such as modified gelonin, a vector may encode non-modified polypeptide sequences such as a tag or targetting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targetting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 5 lists several elements/promoters that may be employed, in the context of the present invention, to regulate the expression of a gene. This list is not intended to be exhaustive of all the possible elements involved in the promotion of expression but, merely, to be exemplary thereof. Table 6 provides examples of inducible elements, which are regions of a nucleic acid sequence that can be activated in response to a specific stimulus.

TABLE 5

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al., 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |

TABLE 5-continued

Promoter and/or Enhancer

| Promoter/Enhancer | References |
|---|---|
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 6

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996), and the SM22α promoter.

Also contemplated as useful in the present invention are the dectin-1 and dectin-2 promoters. Additional viral promoters, cellular promoters/enhancers and inducible promoters/enhancers that could be used in combination with the present invention are listed in Tables 5 and 6. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest. Alternatively, a tissue-specific promoter for cancer gene therapy (Table 7) or the targeting of tumors (Table 8) may be employed with the nucleic acid molecules of the present invention.

TABLE 7

Candidate Tissue-Specific Promoters for Cancer Gene Therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas | Type II pneumocytes; Clara cells |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g.: Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 8

Candidate Promoters for Use with a Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |

TABLE 8-continued

Candidate Promoters for Use with a Tissue-Specific Targeting of Tumors

| Promoter | Cancers in which Promoter is active | Normal cells in which Promoter is active |
| --- | --- | --- |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes | b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (available on the World Wide Web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUSEXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX® (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

4. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

5. Antisense and Ribozymes

Modulators of Fortilin include molecules that directly affect RNA transcripts encoding Fortilin polypeptides. Antisense and ribozyme molecules target a particular sequence to achieve a reduction or elimination of a particular polypeptide, such as Fortilin. Thus, it is contemplated that nucleic acid molecules that are identical or complementary to all or part of SEQ ID NO:1 are included as part of the invention.

a. Antisense Molecules

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

b. Ribozymes

The use of Fortilin-specific ribozymes is an embodiment of the present invention. The following information is provided in order to compliment the earlier section and to assist those of skill in the art in this endeavor.

Ribozymes are RNA-protein complexes that cleave nucleic acids in a site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the down regulation of Fortilin include sequences from the Group I self splicing introns including tobacco ringspot virus (Prody et al., 1986), avocado sunblotch viroid (Palukaitis et al., 1979; Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A,C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible. The message for IGFBP-2 targeted here are greater than 1400 bases long, with greater than 260 possible cleavage sites.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in Fortilin-targeted ribozymes is simply a matter of preparing and testing a given sequence, and is a routinely practiced "screening" method known to those of skill in the art.

B. Nucleic Acid Detection

In addition to their use in directing the expression of Fortilin modulator proteins, polypeptides and/or peptides, the nucleic acid sequences disclosed herein have a variety of other uses. For example, they have utility as probes or primers for embodiments involving nucleic acid hybridization. They may be used in diagnostic or screening methods of the present invention. Detection of nucleic acids encoding Fortilin or Fortilin modulators are encompassed by the invention.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO:1 or any other SEQ ID NO corresponding to a nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, ie., new templates are not produced from the resultant RNA transcripts. Other amplification methods include "RACE" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HTLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

a. Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from a cell, such as a Fortilin-encoding transcript. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

b. Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al., 1991). It is contemplated that this technology may be used in conjunction with evaluating the expression level of Fortilin with respect to diagnostic, as well as preventative and treatment methods of the invention.

C. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

D. Transgenic and Knockout Animals

1. Knockout Animals

The generation of an animal model lacking Fortilin or a particular Fortilin modulator is contemplated as part of the present invention to understand further disease progression and Fortilin function. The lack of Fortilin activity may provoke various types of pathophysiological disturbances in a knockout animal; a knockout mouse lacking Fortilin or a Fortilin modulator is specifically contemplated. One method of inhibiting the endogenous expression of Fortilin in an animal is to disrupt the gene in germline cells and produce offspring from these cells. This method is generally known as knockout technology. U.S. Pat. No. 5,616,491, incorporated herein by reference in its entirety, generally describes the techniques involved in the preparation of knockout mice, and in particular describes mice having a suppressed level of expression of the gene encoding CD28 on T cells, and mice wherein the expression of the gene encoding CD45 is suppressed on B cells. Pfeffer et al. (1993) describe mice in which the gene encoding the tumor necrosis factor receptor p55 has been suppressed. The mice showed a decreased response to tumor necrosis factor signaling. Fung-Leung et al. (1991a; 1991b) describe knockout mice lacking expression of the gene encoding CD8. These mice were found to have a decreased level of cytotoxic T cell response to various antigens and to certain viral pathogens such as lymphocytic choriomeningitis virus.

The term "knockout" refers to a partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of: (1) DNA from some portion of the gene (exon sequence, intron sequence, and/or promoter sequence) to be suppressed, such as all or part of SEQ ID NO:1; and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA).

The knockout construct nucleic acid sequence may comprise 1) a full or partial sequence of one or more exons and/or introns of the gene to be suppressed (thus all or part of SEQ ID NO:1), 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phenotype of a mouse heterozygous for Fortilin may lend clues as to the function and importance of Fortilin, as well as contribute an understanding to the physiological relevance of Fortilin, particular with respect to disease states. Mice completely lacking Fortilin (homozygous null) may provide additional information. Mice lacking Fortilin may not be viable, which itself is indicative of the importance of Fortilin. Should such mice be viable (heterozygous or homozygous nulls), they may be crossed with other transgenic or knockout mice, particular p53 or MCL1 knockout mice to evaluate the physiological importance of the interactions between Fortilin and p53 or MCL1. Furthermore, knock-out mice having any phenotype that resembles a disease state may be used to screen or test therapeutic drugs that slow, modify, or cure conditions. As is known to the skilled artisan, a conditional knockout, wherein the gene is disrupted under certain conditions, is frequently used.

2. Transgenic Animals

It is further contemplated that transgenic animals are part of the present invention. A transgenic animal of the present invention may involve an animal in which Fortilin or a Fortilin modulator is expressed temporally or spatially in a manner different than a non-transgenic animal. Thus, it is contemplated that the transgene, such as a gene encoding Fortilin or a Fortilin modulator, may be expressed in a different tissue type or in a different amount or at a different time than the endogenously expressed version of the transgene.

In a general aspect, a transgenic animal is produced by the integration of a given transgene into the genome in a manner that permits the expression of the transgene, or by disrupting the wild-type gene, leading to a knockout of the wild-type gene. Methods for producing transgenic animals are generally described by Wagner and Hoppe (U.S. Pat. No. 4,873,191; which is incorporated herein by reference), Brinster et al. (1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production. Transgenic animals may be crossed with other transgenic animals or knockout animals to evaluate phenotype based on compound alterations in the genome.

II. Screening Methods Involving FORTILIN

A. Screening for Modulators of Fortilin

The present invention further comprises methods for identifying modulators of Fortilin activity. These assays may comprise random screening of large libraries of candidate substances; alternatively, the assays may be used to focus on particular classes of compounds selected with an eye towards structural attributes that are believed to make them more likely to modulate the function of Fortilin.

By function, it is meant that one may assay for a measurable effect on Fortilin activity. To identify a Fortilin modulator, one generally will determine the activity or level of inhibition of Fortilin in the presence and absence of the candidate substance, wherein a modulator is defined as any substance that alters these characteristics. For example, a method generally comprises:

(a) providing a candidate modulator;
(b) admixing the candidate modulator with an isolated compound or cell expressing the compound;

(c) measuring one or more characteristics of the compound or cell in step (b); and (d) comparing the characteristic measured in step (c) with the characteristic of the compound or cell in the absence of said candidate modulator, wherein a difference between the measured characteristics indicates that said candidate modulator is, indeed, a modulator of the compound or cell.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may be a "modulator" of Fortilin, i.e., potentially affect Fortilin activity, directly or indirectly. A modulator may be a "Fortilin inhibitor," which is a compound that overall effects an inhibition of Fortilin activity, which may be accomplished by inhibiting Fortilin expression, translocation or transport, function, expression, post-translational modification, location, half-life, or more directly by preventing its activity, such as by binding Fortilin. A modulator may be a "Fortilin enhancer," which enhances or increases Fortilin activity, by increasing, for example, expression, translocation or transport, function, expression, post-translational modification, location, half-life, or more directly its activity. An direct increase in Fortilin activity may be accomplished by increasing, for example, its binding activity. Any modulator described in methods and compositions herein may be an inhibitor or an enhancer.

The candidate substance may be a protein or fragment thereof, a small molecule, or even a nucleic acid molecule. An example of pharmacological compounds will be compounds that are structurally related to Fortilin, or a molecule that binds Fortilin such as p53 or MCL1. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are well known to those of skill in the art. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on Fortilin. Regardless of the type of inhibitor or activator identified by the present screening methods, the effect of the inhibition or activator by such a compound results in alteration in Fortilin activity as compared to that observed in the absence of the added candidate substance.

2. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

B. Diagnostic Methods

In some embodiments of the present invention, methods of screening for Fortilin activity, expression level, and mutation status of the gene or transcript encoding Fortilin maybe employed as a diagnostic method to identify subjects who have or may be at risk for developing cancer, who have a particularly aggressive form of cancer, or who have or may be at risk for developing another hyperproliferative or vascular disease/condition. Fortilin activity may be evaluated using any of the methods and compositions disclosed herein, including assays involving evaluating Fortilin's binding activity or ability to inhibit apoptosis. Any other the compounds or methods described herein may be employed to implement these diagnostic methods.

Assays to evaluate the level of expression of a polypeptide are well known to those of skill in the art. This can be accomplished also by assaying Fortilin mRNA levels, mRNA stability or turnover, as well as protein expression levels. It is further contemplated that any post-translational processing of Fortilin may also be evaluated, as well as whether it is being localized or regulated properly. In some cases an antibody that specifically binds Fortilin may be used.

Furthermore, it is contemplated that the status of the gene may be evaluated directly or indirectly, by evaluating genomic DNA sequence comprising the Fortilin coding regions and noncoding regions (introns, and upstream and downstream sequences) or mRNA sequence. The invention also includes determining whether any polymorphisms exist in Fortilin genomic sequences (coding and noncoding). Such assays may involve polynucleotide regions that are identical or complementary to Fortilin genomic sequences, such as primers and probes described herein.

IV. Pharmaceutical Formulations, Delivery, and Treatment Regimens

In an embodiment of the present invention, a method of treatment for a hyperproliferative disease, such as cancer, or a vascular disease or condition by the delivery of a Fortilin modulator is contemplated. Hyperproliferative diseases that are most likely to be treated in the present invention are those that result from mutations in an oncogene and/or the reduced expression of a wild-type protein in the hyperproliferative cells. An increase in Fortilin expression or activity may be considered to be related to the promotion or maintenance of unregulated growth control. Examples of hyperproliferative diseases contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, bladder cancer and any other hyperproliferative diseases that may be treated by altering the activity of Fortilin, such as atherosclerosis.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

Preferably, patients will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

A. Administration

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the therapeutic compound such as a polypeptide or an expression construct encoding a polypeptide. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

To effect a therapeutic benefit with respect to a vascular condition or disease, one would contact a vascular cell with the therapeutic compound. Any of the formulations and routes of administration discussed with respect to the treatment or diagnosis of cancer may also be employed with respect to vascular diseases and conditions.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a Fortilin modulator or an Fortilin modulator-encoding construct. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

B. Injectable Compositions and Formulations

The preferred method for the delivery of an expression construct encoding all or part of a Fortilin protein to hyperproliferative cells in the present invention is via intratumoral injection. However, the pharmaceutical compositions disclosed herein may alternatively be administered parenterally, intravenously, intradermally, intramuscularly, transdermally or even intraperitoneally as described in U.S. Pat. Nos. 5,543,158; 5,641,515 and 5,399,363 (each specifically incorporated herein by reference in its entirety).

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Combination Treatments

The compounds and methods of the present invention may be used in the context of hyperproliferative diseases/conditions including cancer and atherosclerosis. In order to increase the effectiveness of a treatment with the compositions of the present invention, such as Fortilin or a Fortilin modulator, or expression construct coding therefor, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery. Likewise, the treatment of a vascular disease or condition may involve both Fortilin, or a Fortilin modulator, of the present invention and conventional vascular agents or therapies. Alternatively, other hyperproliferative diseases or conditions such as restenosis, primary psoriasis, angiogenesis, rheumatoid arthritis, inflammatory bowel disease, psoriasis, eczema, secondary cataracts, and bronchial dysplasia may be treated with compositions and by methods of the present invention in combination with therapeutic agents typically employed in the treatment of the particular hyperproliferative disease or condition.

Various combinations may be employed; for example, a Fortilin modulator is "A" and the secondary anti-cancer or vascular agent/therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic expression constructs of the present invention to a patient will follow general protocols for the administration of that particular secondary therapy, taking into account the toxicity, if any, of the Fortilin or Fortilin modulator treatment. It is expected that the treatment cycles would be repeated as necessary. It also is contemplated that various standard therapies, as well as surgical intervention, may be applied in combination with the described hyperproliferative cell or vascular therapy.

1. Anti-Cancer Therapy

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that Fortilin modulator therapy could be used similarly in conjunction with chemotherapeutic, radiotherapeutic, immunotherapeutic or other biological intervention, in addition to other pro-apoptotic or cell cycle regulating agents.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of Fortilin would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the Fortilin-related therapies described herein.

i) Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

ii) Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

iii) Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated anigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

d. Genes

In yet another embodiment, the secondary treatment is a gene therapy in which a therapeutic polynucleotide (or second therapeutic polynucleotide if a Fortilin modulator is provided to a cell by providing a nucleic acid encoding the modulator) is administered before, after, or at the same time as a Fortilin modulator is administered. Delivery of a vector encoding a Fortilin modulator in conjunction with a second vector encoding one of the following gene products will have a combined anti-hyperproliferative effect on target tissues. Alternatively, a single vector encoding both genes may be used. A variety of proteins are encompassed within the invention, some of which are described below. Table 6 lists various genes that may be targeted for gene therapy of some form in combination with the present invention.

i) Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

ii) Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

In addition to p53, which has been described above, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zacl, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC.

iii) Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 9

Oncogenes

| Gene | Source | Human Disease | Function |
|---|---|---|---|
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis virus; ALV promoter insertion; amplified human tumors | Amplified, deleted Squamous cell Cancer; glioblastoma | EGF/TGF-α/ Amphiregulin/ Hetacellulin receptor |

TABLE 9-continued

Oncogenes

| Gene | Source | Human Disease | Function |
|---|---|---|---|
| ERBB-2/NEU/HER-2 | Transfected from rat Glioblastomas | Amplified breast, Ovarian, gastric cancers | Regulated by NDF/Heregulin and EGF-Related factors |
| FMS | SM feline sarcoma virus | | CSF-1 receptor |
| KIT | HZ feline sarcoma virus | | MGF/Steel receptor Hematopoieis |
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like transcription factor)/PDGF receptor gene Fusion |
| TGF-β receptor | | Colon carcinoma mismatch mutation target | |
| NONRECEPTOR TYROSINE KINASES | | | |
| ABL | Abelson Mul. V | Chronic myelogenous leukemia translocation with BCR | Interact with RB, RNA polymerase, CRK, CBL |
| FPS/FES | Avian Fujinami SV; GA FeSV | | |
| LCK | Mul. V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and Drosophilia homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALL | Signaling |
| MISCELLANEOUS SIGNALING | | | |
| BCL-2 | Translocation | B-cell lymphoma | Apoptosis |
| CBL | Mu Cas NS-1 V | | Tyrosine- |

TABLE 9-continued

Oncogenes

| Gene | Source | Human Disease | Function |
|---|---|---|---|
| CRK | CT10 ASV | | Phosphorylated RING finger interact Abl Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL in CML | Exchanger; protein Kinase |
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary cancer/ovarian cancer | Localization unsettled |
| BRCA 2 | Heritable suppressor | Mammary cancer | Function unknown |
| ERBA | Avian erythroblastosis Virus | | Thyroid hormone receptor (transcription) |
| ETS | Avian E26 virus | | DNA binding |
| EVII | MuLV promotor Insertion | AML | Transcription factor |
| FOS | FBJ/FBR murine osteosarcoma viruses | | Transcription factor with c-JUN |
| GLI | Amplified glioma | Glioma | Zinc finger; cubitus interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Reticuloendotheliosis Virus | | NF-κB family transcription factor |
| SKI | Avian SKV770 Retrovirus | | Transcription factor |

TABLE 9-continued

Oncogenes

| Gene | Source | Human Disease | Function |
|---|---|---|---|
| VHL | Heritable suppressor | Von Hippel-Landau syndrome | Negative regulator or elongin; transcriptional elongation complex |
| WT-1 | | Wilm's tumor | Transcription factor |
| CELL CYCLE/ DNA DAMAGE RESPONSE | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition leukemia | |
| FHIT | Fragile site 3p14.2 | Lung carcinoma | Histidine triad-related diadenosine 5',3''''- $P^1.p^4$tetraphosphate asymmetric hydrolase |
| hMLI/MutL | | HNPCC | Mismatch repair; MutL Homologue |
| HMSH2/MutS | | HNPCC | Mismatch repair; MutS Homologue |
| HPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger |

2. Therapy for Vascular Diseases and Conditions

The treatment, prevention, and diagnosis of vascular conditions and diseases characterized by hyperproliferative cells are contemplated as part of the present invention. Treatment and prevention may involve a Fortilin modulator (inhibitor or enhancer), or it may involve Fortilin. Vascular conditions and diseases include, but are not limited to, chronic heart failure, hypertensive cardiovascular disease, ischemic heart disease (e.g., coronary artery disease, including atherosclerosis and arteriosclerosis), arrhythmia, congenital heart disease, valvular heart disease or stenotic defect, cardiomyopathy, aneurysm, chronic venous insufficiency. Particularly contemplated for use with the compositions and methods of the present invention are atherosclerosis, restenosis, hemangioma, and cancer angiogenesis.

Atherosclerosis involves the deposit of fatty substances, cholesterol, cellular waste products, calcium and other substances in the inner lining of an artery. This accumulation is referred to as "plaque." Arteriosclerosis, which often accompanies atherosclerosis, refers to the hardening of arteries. Plaque can partially or completely block blood flow through an artery, which may lead to a heart attack or stroke. Restenosis is an accelerated form of atherosclerosis in which hyperproliferation of smooth muscle cells in the vascular wall may quickly obstruct the lumen, which may have been enlarged by percuatenous transluminal coronary angioplasty (PTCA), stent placement, or atherectomy. Hemangioma is a form of a benign tumor in which cells of the vascular tissue grow uncontrollably. Cancer angiogenesis involves the development of small vessels to feed growing cancer cells that may metasize. Induction of apoptosis for the treatment of these diseases and conditions is specifically contemplated using the methods and compositions of the present invention.

Alternatively, Fortilin may be provided to a subject susceptible to or experiencing vascular diseases or conditions such as myocarditis, acute myocardial infarction or stroke. Myocarditis is the inflammation of myocardium and loss of contractile myocytes due to apoptosis and necrosis. Therapies that increase the Fortilin level of cardiomyocytes are considered an embodiment of the invention. Similarly, therapies that increase intracellular Fortilin can prove beneficial in patients with acute myocardial infarction or stroke through the prevention of apoptosis of myocytes (hear muscle cells) and neurons that under apoptotis after prolonged ischemia (oxygen deprivation).

Typical treatments of subjects having a vascular disease or condition, termed "vascular therapy" include performing surgery on the subject, providing a cardiovascular mechanical prostheses, angioplasty, mechanical circulatory support, coronary artery reperfusion, catheter ablation, or an implantable cardioverter defibrillator to the subject, or administering to the subject a cardiovascular therapeutic agent, thrombolytic agent, or lipid lowering therapy. The term "cardiovascular therapeutic agent" is used in the present disclosure to refer to an agent that is a diuretic, calcium channel blocker, beta blocker, vasodilator, positive inotropic agent, beta-adrenergic agonist, vasopressor, alpha blocker, ACE inhibitor, ANG receptor blocker, ganglion blocking agent, other sympatholytics, andrenergic antagonist, alpha-beta blocker, calcium antagonist, oral anticoagulant, aspirin, warfarin, Class I antiarrhythmic agent, Class IB antiarrhythmic agent, Class IC antiarrhythmic agent, Class II antiarrhythmic agent, Class III antiarrhythmic agent, Class IV antiarrhythmic agent, nitroglycerin, magnesium, antiobiotic, antiplatelet agent, statins (HMG-CoA reductases), niacins and other vitamins (including vitamins E and C), or NF-κB inhibitors such as leflunomide and its metabolites, resveratrol, oleandrin, and vesnarinone. A mechanical circulatory support may be an intra-aortic balloon counterpulsation or left ventricular assist device. It is further contemplated that the thrombolytic agent comprises heparin, streptokinase, urokinase, tissue plasminogen activator, or a combination thereof. The administration and dosages for the various agents described above are well known in the medical field. Such dosages may need to be adjusted when used in combination with Fortilin-based compositions of the present invention.

Thus, it is contemplated that any of these vascular therapies may be administered to a subject in combination with Fortilin or Fortilin modulator therapies for the treatment of prevention of a vascular disease or condition.

3. Therapy for Other Diseases and Conditions that Benefit by Inhibition of Apoptosis The treatment and prevention of conditions and diseases characterized by apoptosis or cell death are contemplated as part of the present invention. Such conditions and diseases include, but are not limited to, spinal cord injury and muscular atrophy. Spinal cord injury represents the loss of neurons after trauma to the spinal cord through necrosis or apoptosis. A certain neuronal growth hormone has been shown to positively modulate the course of spinal cord injury. Therapies that increase the intracellular level or activity of Fortilin can be beneficial to reduce the post-traumatic neuronal apoptosis thereby improving the prognosis of patients with spinal cord injury. As for muscular atrophy, a variety of situations could lead to this condition in patients. For example, passengers in spacecrafts experience the absence of gravity for prolonged periods of time, causing muscle cells to undergo excessive atrophy and apoptosis. An increase in Fortilin activity or level in muscle tissue can retard such muscle atrophy.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fortilin is an Anti-Apoptotic Protein

A. Material and Methods

Cell Lines and Culture Conditions: The ML1a cell line was maintained in RMPI medium with 10% fetal calf serum (FCS) and antibiotic supplement. The A543, U2OS, HeLa, 293, MCF-7 and NIH 3T3 cell lines were maintained with Dulbecco's modified Eagle's medium (DMEM) supplemented with 10% FCS and antibiotics.

Molecular Cloning: The cDNA fragments of full length Fortilin, p21, LacZ and MCL1 were obtained by standard PCR technique (Ausubel et al., 1998) using appropriate primer sets and were ligated in-frame to appropriate yeast and mammalian expression vectors. In all cases, the authenticity of cloned constructs were confirmed by automated dideoxynucleotide sequencing (SeqWright Co., Houston, Tex.).

Yeast Two-hybrid Library Screening and Sequence Analysis: The full length MCL1 was cloned into pAS2.1 (ClonTech, Palo Alto, Calif.), a vector that encodes GAL4 DNA-binding domain, and used as bait. Screening of human fetus liver library was performed according to the manufacturer's instruction (ClonTech. Yeast Protocols Handbook, 1997) and as described in our previous paper (Gong et al., 1997). The full length human Fortilin sequence was aligned to those of other species using the OMEGA nucleic acid and protein analysis software (Genetics Computer Group, Madison, Wis.). The hydrophilicity score was determined by the same software using Goldman, Engelberg and Steitz (GES) (Engelman et al., 1986) and von Heijne(von Heijine, 1981) methods.

Northern Blotting: Northern blotting was performed using the MULTIPLE TISSUE NORTHERN MEMBRANE (OriGene, Rockville, Md.) and a $^{32}$P-labeled Fortilin probe generated by the random prime method (Roche), as described previously (Kamitani et al., 1997).

Cell death assay: The experiment was performed in duplicate and repeated at least three times. A total of 1×10 (Nigg, 1997) HeLa cells were seeded in each well of a 4-well Lab-Teck™ chamber slides (Nalge Nunc International), and transfected with pFLAG containing Fortilin or other control cDNAs, using FuGENE6 (Roche). Twenty-four hours after the transfection, the cells were challenged by 5 μg/mL etoposide for 12 hours. Cells were stained for the FLAG-epitope using anti-FLAG antibody (M2, Sigma Co) and anti-mouse IgG conjugated to Rhodamine Red X (Jackson ImmunoResearch Laboratories). The nuclei were stained with DAPI (4,6-Diamidino-2-phenylindole, Sigma Co). Cells were then examined under a Zeiss AXIOSKOP fluorescent microscope (Carl Zeiss Ltd.), using appropriate filter sets. Cells that emitted red fluorescence were evaluated for their nuclear morphology. Condensed or fragmented nuclei were counted as apoptotic. An apoptotic index was then calculated as the number of red cells with apoptotic nuclear morphology divided by the number of total red cells counted and multiplied by 100.

Immunocytochemistry: For the intracellular localization of Fortilin, HeLa cells were seeded in 4 well Lab-Teck™ chamber slides (Nalge Nunc International, Rochester, N.Y.), and transfected with pFLAG containing Fortilin or other control cDNAs, using FuGENE6 (Roche). Twenty-four hours after the transfection, the cells were fixed with 4% paraformaldehyde in PBS, permeabilized at −20° C. with acetone-methanol solution (v/v 1:1), blocked with 10% normal goat serum, and probed with anti-FLAG (M2, Sigma Co.). Bound primary antibodies were detected with goat secondary antibody conjugated to Rhodamine Red X (Jackson ImmunoResearch Laboratories, West Grove, Pa.). The nucleus was counterstained by DAPI (4,6-Diamidino-2-phenylindole, Sigma Co.). Slides were examined under a Zeiss AXIOSKOP fluorescent microscope (Carl Zeiss Ltd., Herts, UK) equipped with a Zeiss image processing system using appropriate filter sets. For the detection of native Fortilin, HeLa cells were processed in the same way as above and probed with anti-Fortilin antibody and goat anti-rabbit antibody conjugated to Rhodamine Red X (Jackson ImmunoResearch Laboratories).

Generation of anti-Fortilin antibody: Antiserum specific for Fortilin was prepared in rabbits using a synthetic peptide $NH_2$-CKYIKDYMKSIKGKLEEQRPER-COOH, (SEQ ID NO:10), corresponding to amino acids $90^{th}$-$111^{th}$ conjugated to maleimide-activated keyhole limpet haemocyanin (KLH) and an appropriate adjuvant. Generated antiserum was purified by affinity chromatography on a peptide-Sepharose matrix and tested by ELISA against a control or the Fortilin peptides.

Western blot of fusion proteins: The full length Fortilin cDNA was cloned in frame to pQE-30 bacterial expression plasmid (Qiagen, Valencia, Calif.). The plasmid was co-transformed into BL21 *E. Coli* with pREP4 plasmid (Qiagen). The polyhistidine tagged Fortilin (MRGS-His$_6$-Fortilin) was induced by addition of IPTG (isoprophyl-β-D-thiogalactopyranoside), purified to near homogeneity under native conditions according to the manufacturer's instruction (Qiagen). The integrity of purified MRGS-His$_6$-Fortilin was confirmed by SDS-PAGE (Polyacrylamide gel electrophoresis) and Coomassie staining, showing a single band at around 30 kDa (Data not shown). For the characterization of the rabbit anti-Fortilin antibody, serially diluted RGS-His$_6$-Fortilin (100 ng to 12.5 ng by weight), was subjected to SDS-PAGE and Western transfer. Transferred proteins were probed first with anti-RGS-His monoclonal antibody (Qiagen). The membrane was then stripped and re-probed with rabbit anti-Fortilin antibody. For the evaluation of the specificity of the antibody, a SDS-PAGE and Western transfer were performed in duplicate. Prior to the addition of antibodies, the membranes were pre-incubated either with a control peptide consisting of $210^{th}$-$230^{th}$ amino acid of MCL1 ($NH_2$-LETLRRVGDGVQRNHETVFQG-COOH) (SEQ ID NO:11) or with the Fortilin peptide (NH2-CKYIKDYMKSIKGKLEEQRPER-COOH) (SEQ ID NO:10)used to raise the antibody, both at a concentration of 100 ng/mL. The rest of immuno-probing was performed as previously described (Kamitani et al., 1997).

Western blot of total cell lysates: Total cell lysate was generated as previously described (Kamitani et al., 1997). Briefly, cells were harvested, washed with cold PBS, counted, centrifuged, and immediately frozen in liquid nitrogen. The SDS loading buffer (5 mM Tris.Cl, , pH 6.8, 100 mM Dithiothreitol, 2% SDS, 0.1% bromophenol blue and 10% glycerol) was then added to the frozen pellet (150 μL for 1 million cells) and the samples were incubated at 45° C. for 1 hour. The genomic DNA in the lysate was sheared by passing the lysate through 27 gauge needles three times each. A total of 7.5 μL of a sample, corresponding to $2.5 \times 10^4$ cells, was loaded to each well. SDS-PAGE, Western transfer and immuno-probing were performed as described previously (Kamitani et al., 1997). The rabbit anti-Fortilin, pre-immune sera and horseradish peroxidase (HRP)-conjugated goat anti-rabbit IgG (Southern Biotechnology Associates, Inc., Birmingham, Ala.) were used at the dilutions of 1:2000 and 1:5000, respectively.

Immunohistochemistry: Human breast tissues were obtained from the Novagen Human Disease Tissue Archive (Novagen, Madison, Wis.) and Biogenex Tissue Archive (Biogenex, San Ramon, Calif.). All the sections were stained in one setting using the same reagents. The sections were first de-waxed, re-hydrated, and subjected to antigen retrieval with CITRA PLUS (Biogenex) using the microwave method according to the manufacturer's instructions. Sections were then subjected to the quenching of endogenous peroxidase and the blocking of tissue avidin and biotin. After blocking with normal goat serum, tissues were incubated with an affinity purified rabbit anti-Fortilin antibody (9 μg/mL) or purified normal rabbit IgG (9 μg/mL) (ChromaPure, Jackson ImmunoResearch) for 30 minutes at room temperature. Bound antibodies were detected using goat anti-rabbit antibody conjugated to avidin, streptavidin-horseradish peroxidase complex (Biogenex, San Ramon, Calif.) and diaminobenzidine (DAB). Tissues were then lightly counterstained with hematoxylin. A brown stain indicated positive Fortilin immunoreactivity. The relative frequency and density of Fortilin positive cells in tissues were quantified using a SAMBA 4000 image analyzer (Dynatech Laboratoreis Inc., Imaging Products International Inc., Chantilly, Va.) equipped with a Nikon Labophoto microscope and a JVC three chip color camera as previously described (Guidozi et al., 1996). The labeling index, mean optical density and integrated score were then calculated. The labeling index is a computer-generated index, representing the ratio of the number of labeled cells divided by the total number of cells. The mean optical density is the mean of optical densities measured over a labeled area. The integrated score is the double product of the labeling index and mean optical density.

Statistical analysis: For the analysis of statistical significance of apoptotic indices among cells transfected with different plasmids, Dunnett's T tests were performed. In all cases, the confidence intervals were 0.95 with the alpha value of 0.05. For the statistical evaluation of the significant linear trend between the amount of plasmids used for the transfection and apoptotic indices, ANOVA (Analysis of Variance) regression analysis was employed. The p-value less than 0.05 was considered to be statistically significant. For the analysis of statistical significance of possible correlation between the degree of malignancy and the indices of Fortilin immunoreactivity, Dunnett's multiple range tests were performed.

Molecular cloning. The cDNA fragments of full-length Fortilin, p21, β-galactosidase (LacZ), bcl-xL, and MCL1 were obtained by standard PCR techniques, using appropriate primer sets and were ligated in-frame to the appropriate bacterial, yeast, and mammalian expression vectors. In all cases, the authenticity of cloned constructs was confirmed by automated dideoxynucleotide sequencing (SeqWright Co., Houston, Tex.).

Generation and characterization of U2OS cells stably expressing Fortilin. U2OS cells were transfected with empty pcDNA6, a mammalian expression vector containing a blasticidine resistance gene (Invitrogen, Carlsbad, Calif.), or with pcDNA6 vector encoding wild-type Fortilin, by using FuGENE6 (Roche Molecular Biochemicals) according to the manufacturer's instructions. Transfected cells were selected for approximately 3 weeks and characterized by Western blot analysis. For the cytotoxicity assay, U2OS cells stably expressing wild-type Fortilin (U2OS.F) and U2OS cells stably harboring empty pcDNA6 (U2OS.E) were seeded in a 96 well plate in quadruplicate. For the investigation of dose response, cells were challenged with various concentrations of etoposide (0-20 µg/mL) for 48 hours. For the time course study, cells were challenged with 5 µg/mL of etoposide and harvested after various incubation periods (0-96 hours). In both cases, the cell media were assayed for the lactate dehydrogenase (LDH) activity released from the cytosol of damaged cells, using a cytotoxicity detection kit (Roche Molecular Biochemicals) according to the manufacturer's instructions. The cytotoxicity index was calculated as follows: (LDH activity in the media–background LDH activity)÷(LDH activity in the medium of cells lysed by 1% Triton X-100–background LDH activity)×100.

Assay of caspase 3-like activity. Approximately $2 \times 10^6$ U2OS stable transfectants, either expressing Fortilin (U2OS.F) or harboring empty expression vector (U2OS.E), both of which have been characterized above, were challenged either with dimethyl sulfoxide (DMSO) (vehicle) or with etoposide at a final concentration of 10 µg/mL for 48 hours. Caspase 3-like activity was then determined as previously described (Mannick et al., 1999). In brief, cytosolic proteins were extracted in hypotonic cell lysis buffer (25 mM HEPES, pH 7.5, 5 mM MgCl$_2$, 5 mM EDTA, 5 mM dithiothreitol, 0.05% phenylmethylsulfonyl fluoride [PMSF]; all from Sigma) by three cycles of freezing and thawing. The protein concentration of samples was determined by using a BioRad Bradford protein assay kit (BioRad). Ten micrograms of cytosolic extracts were added to caspase assay buffer (312.5 mM HEPES, pH 7.5, 31.25% sucrose, 0.3125% CHAPS) with Z-DEVD-AFC as substrates (CalBiochem, San Diego, Calif.). Release of 7-amido-4-(trifluoromethyl) coumarin (AFC) was quantified, after 2 hours of incubation at 37° C. (or, in the case of time course experiment, every 10 minutes), using a Fluoroskan system (Thermo-Labsystems, Helsinki, Finland) set to an excitation value of 355 nm and emission value of 525 nm. The results were expressed as relative fluorescence unit (R.F.U.) per microgram of protein.

Assay of antisense-treated MCF-7 cell survival. For the Western blot analysis to evaluate intracellular Fortilin concentration with antisense treatment, $1 \times 10^6$ MCF-7 cells, a malignant breast ductal carcinoma cell line, were seeded on a 6 well plate. Next day, Z-DEVD-FMK (Kamiya Biomedical Company, Seattle, Wash.), a caspase-3 inhibitor, was added to the media at the concentration of 100 µM. Twenty-four hours after the addition of the caspase inhibitor, cells were transfected with pFLAG-antisense Fortilin by FuGENE6 (Roche Molecular Biochemicals). Cells were harvested immediately after the transfection and eight-hours after the transfection by the direct addition of RIPA buffer (50 mM Tris-HCl, pH 7.2, 150 mM NaCl, 1% Nonidet P-40, 1% dosium deoxycholate, 0.1% SDS), supplemented with PMSF and aporotinin. Exactly ten micrograms of protein extracts were then resolved by SDS-PAGE and subjected to Western blot analysis using anti-actin (Chemicon, Temecula, Calif.) and anti-Fortilin antibodies with appropriate secondary antibodies conjugated to horseradish peroxidase (HRP) (Southern Biotechnology Associates, Inc). The rest of the immunoprobing was performed as previously described (Fujise et al., 2000). For the cell survival assay, MCF-7 cells were seeded onto 24-well plates in triplicate. The next day, cells were transfected by FuGENE6 (Roche Molecular Biochemicals) with either pFLAG-antisense Fortilin or empty pFLAG vector, with pFLAG-LacZ used as a transfection-survival marker. Cells were harvested 12, 24, 36, 48 or 72 hours after the transfection and assayed for β-galactosidase activity with Galacto-Light Plus Assay Kit (Tropix, Bedford, Mass.). The loss of exogenous β-galactosidase activity in the assay reflected the death and loss of transfected cells while the remaining exogenous β-galactosidase activity represented the survival and retention of transfected cells. The survival index of the antisense-treated cells was calculated as (β-galactosidase activity of antisense-treated cells at a given time point)÷(β-galactosidase activity of control cells at the same time point)×100.

Cells, cell lines and culture conditions. The U2OS osteosarcoma cell line and Human Embryonic Kidney 293 cell line were used along with the COS-7 transformed African green monkey fibroblast cell line. These cell lines were maintained in Dulbecco's modified Eagle's medium (DMEM) supplemented with 10% fetal calf serum (FCS) and antibiotics. Human aortic vascular smooth muscle cells were purchased from Cascade Biologics (Portland, Oreg.) and maintained in M231 medium according to the manufacturer's instructions. Cells from passages 4-7 were used.

Molecular cloning. The cDNA fragments of full-length Fortilin and its deletion mutants, MCL1, Bcl-xL, Bak, Bax, and PCNA were obtained by standard polymerase chain reaction (PCR) technique as described previously (Fujise et al., 2000), using appropriate primer sets, and were ligated in-frame to appropriate yeast and mammalian expression vectors. In all cases, the authenticity of cloned constructs was confirmed by automated dideoxynucleotide sequencing (SeqWright Co., Houston, Tex.).

Yeast two-hybrid library screening. The full-length MCL1 was cloned into pAS2.1 (ClonTech, Palo Alto, Calif.), a vector that encodes a GAL4 DNA-binding domain, and used as bait. *Saccharomyces cerevisiae* PJ69-2A cells (MATa; ClonTech) were transformed with the pAS2.1-MCL1 vector, using the lithium acetate method as described previously (Gong et al.,). Yeast mating was then performed between PJ69-2A cells containing pAS2.1-MCL1, and Y187 cells (MATα) containing a human fetal liver library in pACT2 (a vector that encodes GAL4 DNA-activating domain) for 27 hours, according to the manufacturer's instructions (ClonTech). Diploid yeast cells were selected for growth on synthetic dropout (SD) plates lacking adenine, histidine, leucine and tryptophan (SD/-Ade/-His/-Leu/-Trp) for 14 days at 30° C. Positive colonies were screened for β-galactosidase activity using a X-gal (5-bromo-4-chloro-3-indolyl β-D-galactopyranoside; Sigma Co., St. Louis, Mo.) filter lift assay. Plasmid DNAs were then isolated from colonies that activated all three yeast reporter genes (HIS3, ADE2, lacZ) using the lyticase method (Fujise et al., 2000); propagated in *Escherichia coli*; and analyzed by restriction digestion and automated dideoxy-nucleotide sequencing (SeqWright).

Yeast two-hybrid assay. *Saccharomyces cerevisiae* SFY526 cells (CloneTech) were cotransformed with (a) empty pAS2.1 vector or pAS2.1 vector containing a full-length MCL1 construct and (b) empty pACT2 vector or pACT2 vector containing FL1, the original clone isolated from yeast two-hybrid screening and representative of the nearly full-length Fortilin molecule (amino acids 5-172). FL1 was redesignated as Fortilin$_{\Delta 5-172}$. Transformed cells were selected on SD plates lacking tryptophan and leucine (SD/-Trp/-Leu plates) for 7 days and subjected to a X-gal filter lift assay as described above. The blue color that developed within 8 hours was considered to represent a positive interaction.

In vitro pull-down assay. Radiolabeled proteins for use in an in vitro binding assay were generated by a TNT Quick Coupled Transcription/Translation System (Promega, Madison, Wis.) according to the manufacturer's instructions, using

[$^{35}$S]methionine (Amersham-Pharmacia, Piscataway, N.J.) as labeling agent. DNA templates were either circular plasmids or gel-purified PCR products containing a T7 RNA polymerase promoter. The in vitro translated, influenza hemagglutinin-tagged Fortilin (Fortilin-HA) or its mutants and another in vitro translated protein namely, MCL1, Bcl-xL, Bak, Bax or PCNA, were added to Buffer A (50 mM HEPES, pH 7.5, 70 mM KCl, 0.5 mM ATP, 5 mM MgSO$_4$, 1 mM DTT, 0.001% NP-40, 50 µM MG132, 2 µg/mL BSA, 2 µg/mL aporotinin, 0.5 mM PMSF and protease inhibitor cocktail [Sigma]), and allowed to form complexes at 4° C. for 90 minutes. Fortilin-HA or its mutants were then pulled down with rat anti-HA antibody (Clone 3F10; Roche Molecular Biochemicals, Indianapolis, Ind.) and sheep anti-rat polyclonal antibody conjugated to Dynabeads™ (M480; Dynal USA, Lake Success, N.Y.). Immune complexes were then washed 5 times with Buffer A and once with Buffer B (Buffer A supplemented with 0.01% NP-40). Finally, precipitated proteins were eluted into SDS gel loading buffer (50 mM Tris-Cl, pH 6.8, 100 mM DTT, 2% SDS, 0.1% bromophenol blue, and 10% glycerol), boiled for 5 minutes, subjected to 12% SDS-polyacrylamide gel electrophoresis (SDS-PAGE) and visualized by fluorography and imaging with a phosphoimager system (Bio-Rad, Hercules, Calif.).

In vivo coimmunoprecipitation assay. COS-7 cells (2.5× 10$^6$) were cotransfected with pcDNA3-Fortilin-HA or pcDNA3 and with FLAG-MCL1/pFLAG-CMV or pFLAG-CMV vectors using FuGENE6 (Roche Molecular Biochemicals), according to the manufacturer's instructions. Thirty-six hours after transfection, cells were harvested by trypsinization, washed with chilled PBS, suspended in the Buffer A, and lysed by a nitrogen cavitation method (PARR Instrument Co, Moline Ill.) (Eichinger et al., 1998) After centrifugation, total cell lysates were incubated with either rat monoclonal anti-HA antibody (Clone 3F10) or control rat monoclonal antibody, both at a concentration of 2 µg/mL. Formed complexes were precipitated by sheep anti-rat antibodies conjugated to Dynabead™ (Dynal USA); washed with Buffers A and B; eluted into SDS gel loading buffer; and subjected to SDS-PAGE, Western blot transfer and immuodetection with anti-HA (16B12; Covance, Richmond, Calif.) and anti-FLAG (M2; Sigma) antibodies. For the in vivo coimmunoprecipitation assay for the stable transfectants of Fortilin and its mutants, U2OS cells stably expressing wild type Fortilin or its mutants were used, along with control U2OS cells stably possessing the empty plasmid. Cells were harvested by scraping, washed with chilled PBS, suspended in Buffer C (Buffer A supplemented with 0.02% NP-40), and lysed by a nitrogen cavitation method (PARR Instrument Co). Cleared total cell lysates were incubated with either rat monoclonal anti-HA antibody (Clone 3F10) or control rat monoclonal antibody, both at a concentration of 2 µg/mL. Formed complexes were precipitated by sheep anti-rat antibodies conjugated to Dynabeads™ (Dynal USA); washed with Buffers C; eluted into SDS gel loading buffer; and subjected to SDS-PAGE, Western blot transfer and immuodetection with anti-HA (16B12; Covance, Richmond, Calif.) and anti-MCL1 (Santa Cruz Biotechnology) antibodies.

Indirect immunofluorescence and confocal laser scanning microscopy. For the intracellular localization of Fortilin and MCL1, U2OS cells that stably express HA-tagged Fortilin (see below for a description of the generation of stable transfectants) were seeded on glass coverslips in 6-well tissue culture plates. The next day, the cells were fixed with 4% paraformaldehyde in PBS, permeabilized at −20° C. with an acetone-methanol solution (v/v 1:1), blocked with 10% normal goat serum and probed with anti-HA monoclonal antibody (16B12; Covance) and rabbit anti-MCL1 polyclonal antibody (Santa Cruz Biotechnology, Inc., Santa Cruz, Calif.). Bound primary antibodies were detected with goat anti-mouse secondary antibody conjugated to Cy-2 and goat anti-rabbit secondary antibody conjugated to rhodamine Red X, respectively (Jackson ImmunoResearch Laboratories, West Grove Pa.). Cell nuclei were counterstained with DAPI (4,6-diamidino-2-phenylindole; Sigma). Stained cells were analyzed on a Zeiss 210 confocal laser scanning microscope equipped with argon 488 nm and helium-neon 543 nm lasers, using a 63× objective and appropriate filter sets (Carl Zeiss Ltd., Herts, United Kingdom). Green and red colors were assigned to the Cy-2 and rhodamine Red-X signals, respectively. Image files were loaded into Adobe Photoshop (Adobe System, Inc., San Jose, Calif.), where superimposed images of Cy-2 and rhodamine Red-X staining were generated. For the characterization of U2OS cells stably expressing HA-tagged Fortilin mutants, transfectant cells were seeded in 4-well Lab-Tek™ chamber slides (Nalge Nunc International, Rochester, N.Y.) and then immunostained as described above, using anti-HA monoclonal antibody (Covance) and goat anti-mouse antibody conjugated to rhodamine Red X (Jackson ImmunoResearch Laboratories). Cells were then examined under a Zeiss Axioskop fluorescent microscope (Carl Zeiss Ltd.) equipped with a Zeiss image processing system and appropriate filter sets.

Generation of recombinant adenoviral vectors encoding Fortilin. The pBHG10, an adenoviral vector with compensating deletions in the early region 1 (E1), was purchased from Microbix Biosystems Inc (Ontario, Canada). Recombinant virus encoding for Fortilin (Ad.Fortilin) was generated, according to the manufacturer's instruction and as described previously (Zoldhelyi et al., 1996; Zoldhelyi 2000). FLAG-epitope-tagged human Fortilin cDNA was cloned into the plasmid shuttle vector pDC515, using a standard PCR based technique. Human embryonic kidney 293 cells then were co-transfected with pBHG10 and pDC515-FLAG-Fortilin using LipofectAMINE PLUS (Roche). Recombinant virus (Ad.Fortilin) generated was further purified by plaque-picking and propagated in HEK293 cells. For control, recombinant virus with no inserted cDNA (Ad.Null) was used.

Western blot analysis of total cell lysates. Total cell lysate from human aortic vascular smooth muscle cells was generated as previously described (Kamitani et al., 1997). In brief, approximately 1×10$^6$ cells in 10-cm tissue culture dishes were made quiescent by maintaining them for 48 hours in Media 231 (Cascade Biologics) containing no serum supplements. Cells were then exposed to Media 231 containing serum supplements and harvested at 0, 1, 2, 4, 8, 24, 48 and 72 hours after the medium change. For the harvesting of cells, 500 µL SDS loading buffer was directly added to cell monolayers after two washings with PBS. Collected samples were incubated at 45° C. for 1 hour. The genomic DNA in the lysate was sheared by passing the lysate through 27-gauge needles three times. Twenty micro-liter of samples, corresponding to 4.0×10$^4$ cells, was loaded in each lane of a 12% SDS-polyacrylamide gel. The SDS-PAGE, Western blot, and immunoprobing were performed as described previously (Fujise et al., 2000). Anti-MCL1 (Santa Cruz Biotechnology, Inc), anti-actin (Roche Molecular Biochemicals) and anti-Fortilin antibodies were used along with appropriate horseradish peroxidase-conjugated secondary antibodies (Southern Biotechnology Associates, Inc., Birmingham, Ala.). Bound antibodies were detected, using an enhanced chemiluminescence (ECL) kit (West Pico; Pierce, Rockville, Md.) according to the manufacturer's instructions. Densitometric analysis was performed using a Bio-Rad chemiluminescence screen and Quantity One software system, according to the manufacturer's instruction. The signal intensities of MCL1 and Fortilin bands were divided by the signal intensity of actin band from the same time point and expressed in terms of fold increase from the Time 0 signals, after normalizing signal intensities at Time 0 to one. The same methods were utilized to assess the influence of Fortilin overexpression on native MCL1 level, and the characterization of stable transfectants.

Generation of stable Fortilin and mutant Fortilin transfectants. U2OS cells were transfected with empty pcDNA6, a mammalian expression vector with blasticidine selection marker (Invitrogen, Carlsbad, Calif.), or the same pcDNA6 vector encoding either wild-type Fortilin, Fortilin$_{\Delta5-172}$ Fortilin$_{\Delta23-172}$, or Fortilin$_{\Delta46-172}$, using FuGENE6 (Roche Molecular Biochemicals). Transfected cells were selected for at least 3 weeks and characterized by immunostaining, Western blot analysis and in vivo immunoprecipitation assay.

Cell death assay. U2OS cells stably expressing Fortilin or its mutants were seeded in 96-well plates in triplicate. Cells were then challenged with 5 μg/mL of etoposide (Sigma) for 48 hours. Then the cell media were assayed for the lactate dehydrogenase (LDH) activity released from the cytosol of damaged cells, using a Cytotoxicity Detection Kit (Roche Molecular Biochemicals), according to the manufacturer's instructions. The cytotoxicity index was calculated as follows: (LDH activity in the media−background LDH activity)/ (LDH activity in the medium of the cells lysed by 1% Triton X-100−background LDH activity)×100.

Statistical analysis. For analysis of the statistical significance of differences in cytotoxicity indices among cells stably transfected with Fortilin, its mutants or control plasmids, Student's t-test was performed using a commercial software (Minitab Inc., State College, Pa.). In all cases, a P-value less than 0.05 was considered to be statistically significant.

B. Results

Using the yeast two-hybrid system, about 1×10 (Schmitt et al., 1998) independent clones in a human fetal liver library were screened with MCL1 (Myeloid Cell Leukemia 1), a Bcl-2 homologue, as bait. The amino acid sequence of one positive clone that specifically interacted with MCL1 was found to be identical to that of human TCTP (Translationally Controlled Tumor Protein). Human TCTP was cloned as a human homologue of the mouse p21 protein, which was originally identified from a mouse L cell library (Chitpatima et al., 1988; Gross et al., 1989). However, mouse L cell line was established from normal mouse subcutaneous connective tissue (Sanford, 1948). In addition, there has been little evidence that the expression of this protein is translationally controlled. The function of this protein has not been elucidated. Based on our observation that TCTP functions as an anti-apoptotic protein (see below), it is now designated Fortilin (Fortis=strong, robust, in Latin).

The Fortilin cDNA encodes for a 172 amino acid polypeptide with no significant homology to any known proteins described previously, in part or as a whole. FIG. 1A shows the amino acid alignment of Fortilin from various species. Clearly, Fortilin is highly conserved not only in mammalian species but also in non-mammalian species (FIG. 1A). The degree of the conservation is unusually high in Fortilin: human and mouse Bcl-2 are 72% identical while human and mouse Fortilin are 95% identical. Fortilin has no homology to any known proteins. Fortilin does not contain typical nuclear localization signals (NLS) (Nigg, 1997) (FIG. 1A), a hydrophobic transmembrane anchor (FIG. 1B) or signal sequence (FIG. 1A).

The amino acid sequence of Fortilin was evaluated for its hydrophilicity using Goldman, Englberg and Steiz (GES) (black line) and von Heijne (gray line) methods, respectively (FIG. 1B). The mid one-thirds of Fortilin is highly hydrophilic, which we designated Domain 2. A peptide representing the $90^{th}$-$111^{th}$ amino acids of Fortilin was used to raise antibody against Fortilin in rabbits. Overall, Fortilin is a hydrophilic protein with the central portion (designated Domain 2) being most hydrophilic.

Northern blot analysis using $^{32}$P-labeled human Fortilin cDNA as probe (FIG. 1C) revealed the ubiquitous presence of Fortilin in normal human tissue. Fortilin signals were found especially abundant in the liver, kidney, small intestine, skeletal muscle and testis (FIG. 1C). The wide tissue distribution of Fortilin indicates that it may be important in the maintenance of basic cellular functions. The presence of weaker band at 1.2 kb, just above the 1.0 kb Fortilin band, may represent the message of a Fortilin-like molecule that remains unidentified (FIG. 1C).

Figure 2A:
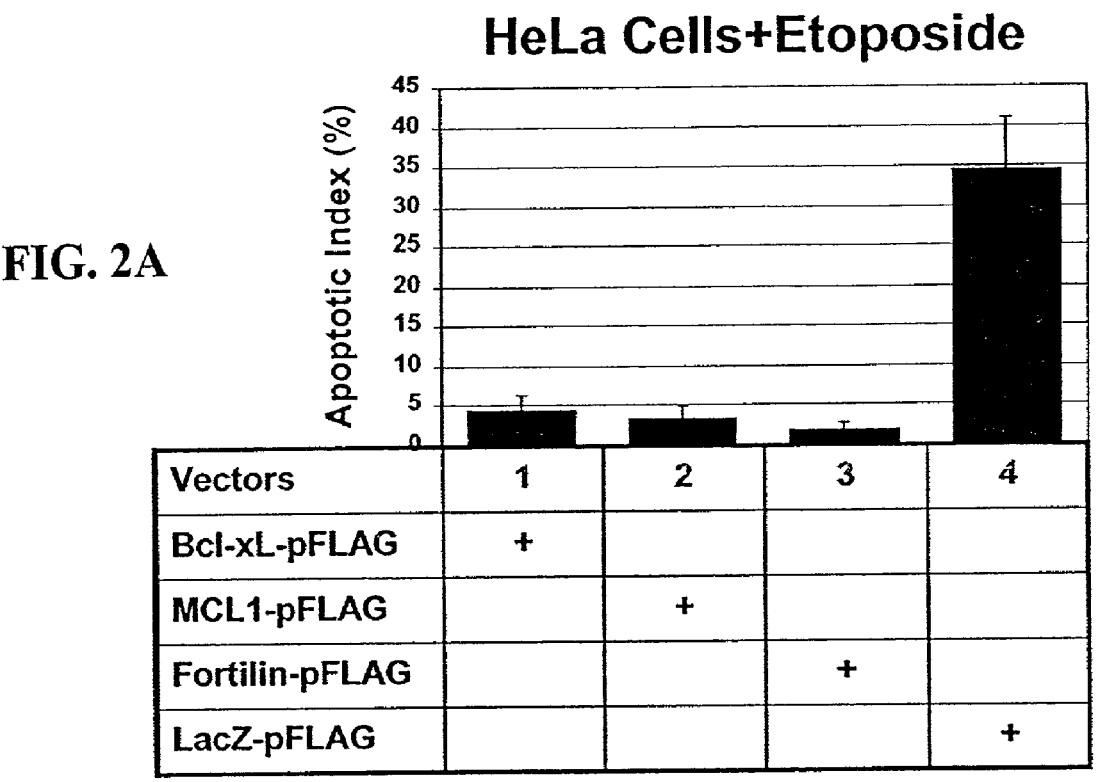
FIGS. 2A-2B. Anti-apoptotic Function of Fortilin.
Figure 2B:
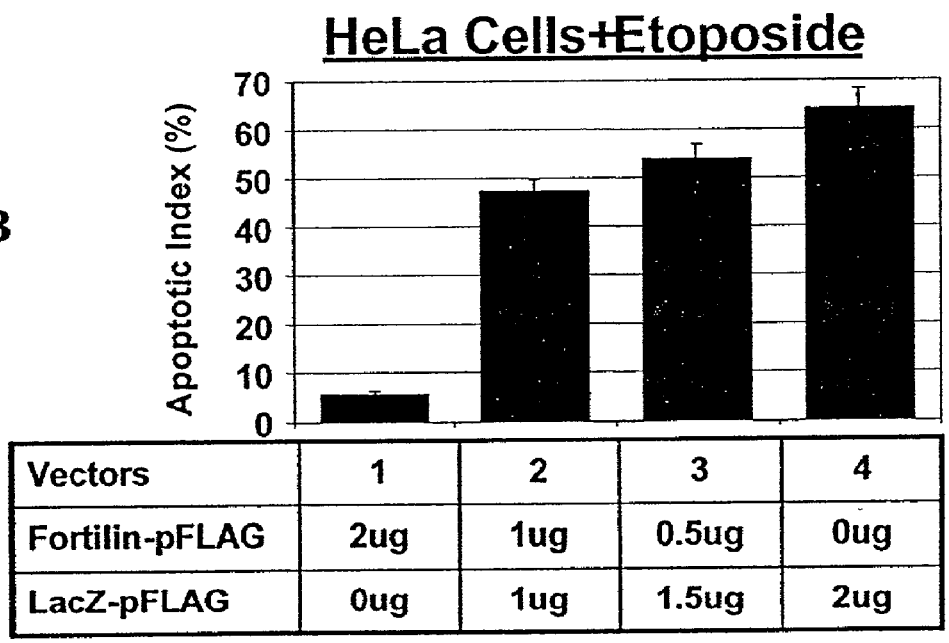

Although the specific function of Fortilin had remained unclear, the fact that we identified Fortilin as a protein that would bind an anti-apoptotic protein MCL1 suggested that it may play a role in apoptosis regulation. Accordingly, whether Fortilin prevented cell death induced by Etoposide (VP16), a chemotherapeutic agent (Hande, 1998), was investigated. The FLAG epitope-tagged Fortilin, Bcl-xL, MCL1, or β-galactosidase (LacZ) was ectopically expressed in HeLa cells. Cells were then challenged by Etoposide. Cells expressing FLAG-tagged proteins were identified by immunostaining with anti-FLAG antibody. Nuclei were stained with DAPI (4,6-Diamidino-2-phenylindole) and examined for their apoptotic morphology. As is shown in FIG. 2A, the overexpression of Bcl-xL and MCL1 prevented HeLa cells from undergoing apoptosis, consistent with previous reports (Schmitt et al., 1998; Zhou et al., 1997). In this system, Fortilin exhibited as strong an anti-apoptotic effect as that of Bcl-xL and MCL1. In addition, the higher levels of Fortilin expression were associated with more prominent anti-apoptotic effects (FIG. 2B). Thus, Fortilin is an anti-apoptotic protein, which inhibits Etoposide induced apoptosis in HeLa cells. Intriguingly, Fortilin does not have structural homologies either to Bcl-2 (Adams & Cory, 1998) or IAP (Inhibitors of apoptosis) family proteins (Duckett et al., 1996) (FIG. 1A). This suggests that Fortilin represents a new class of anti-apoptotic proteins.

In order to investigate the clinical relevance of Fortilin, a polyclonal rabbit anti-Fortilin antibody was raised against the $99^{th}$-$113^{th}$ amino acids, which are within Domain 2 of Fortilin (FIG. 1B). The anti-Fortilin antibody was found capable of recognizing full-length recombinant Fortilin with a good sensitivity and specificity. Various amounts of recombinant polyhistidine-tagged human Fortilin were size-fractionated using SDS-PAGE and probed with anti-polyhistidine monoclonal antibody (Qiagen) and with anti-Fortilin antibody. The sensitivity of the anti-Fortilin antibody is comparable to that of anti-polyhistidine antibody. Supporting the specificity of the antibody, the anti-Fortilin antibody did not bind to Fortilin transferred to a nitrocellulose membrane when blocked with a Fortilin specific peptide.

Figure 3:
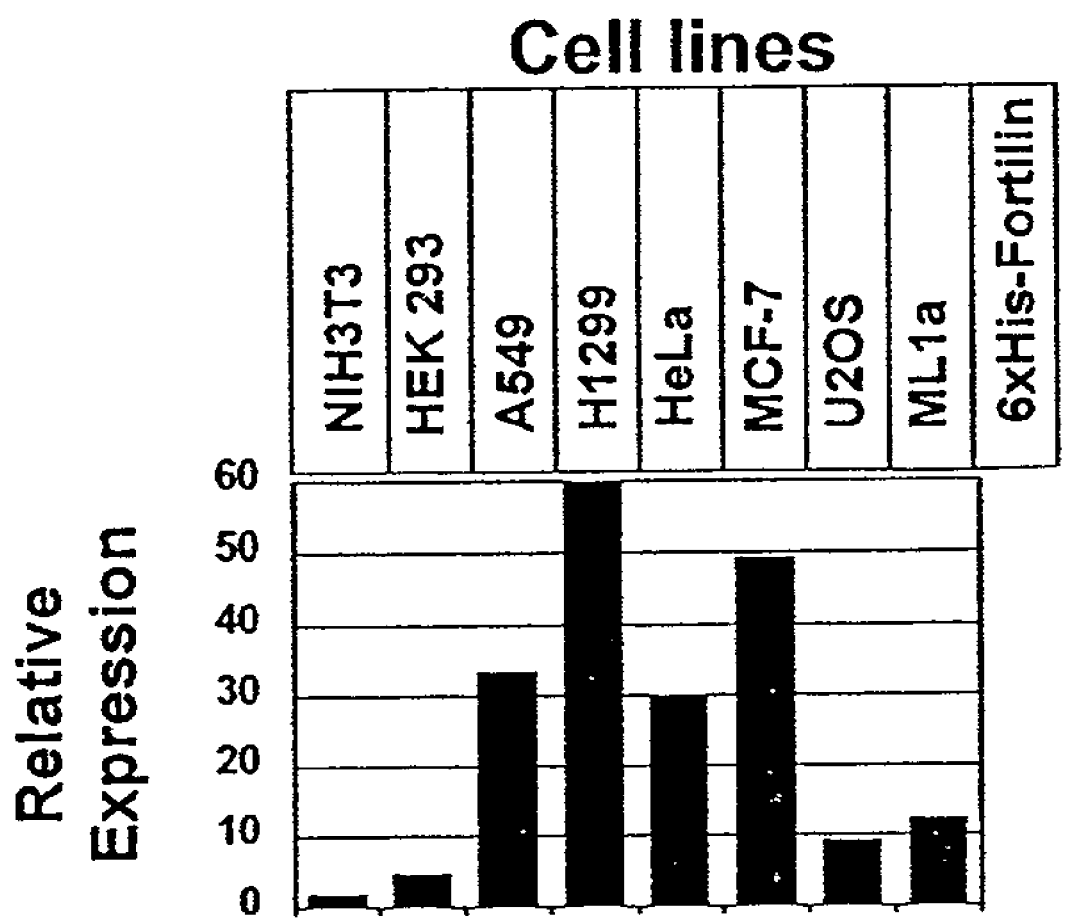
FIG. 3. Expression of Fortilin. Cell lysates from various cell lines, corresponding to approximately $2.5 \times 10^4$ cells, were evaluated for Fortilin expression using the anti-Fortilin antibody characterized above. Fortilin expression was highly abundant in tumor cell lines of epithelial origin.
Figure 4:
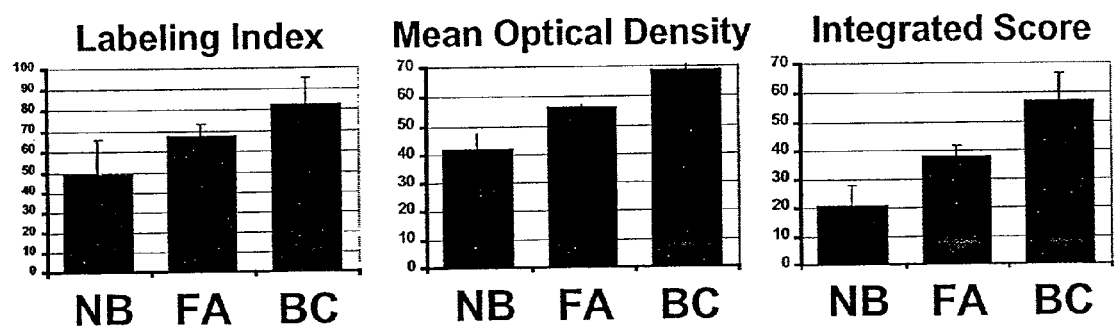
FIG. 4: The Overexpression of Fortilin in Breast Tissue. Normal human breast (NB), fibroadenoma (FA), and ductal carcinoma (BC) sections were stained using anti-Fortilin antibody. The computational antigen quantification, using a SAMBA 4000 Image Analysis System, is shown in the figure. As is seen in the graphs of the labeling index, mean optical density and integrated score, the DAB signal score was highest in tissues from malignant ductal carcinoma tissue (BC), followed by fibroadenoma (FA) and normal breast tissues (NB). A statistically significant linear relationship was present between the degree of malignancy (normal to fibroadenoma to breast cancer) and the mean optical density and integrated score at the 0.05 level.

The expression of native Fortilin in various cell lines was evaluated by immunoblot analysis. While there was no significant signal detected when immunoblotted with rabbit preimmune sera, the anti-Fortilin sera yielded one discrete band with the size of ~28 kDa (FIG. 3). The calculated size of Fortilin is ~19 kDa. Since the recombinant polyhistidine tagged human Fortilin exhibited a band at ~30 kDa, the discrepancy between the calculated size and apparent size on the immunoblot may be due to its aberrant migration on the SDS (Sodium Dodecyl Sulfate) gel. Aside from the uniformity of the size of immunoblotted Fortilin, a significant variation in the degree of its expression also was observed. Elevated expression of Fortilin was observed in cancerous cell lines such as H1299 (non-small cell lung cancer cell line), MCF-7 (breast cancer cell line), HeLa (cervical cancer cell line) and A549 (lung adenocarcinoma cell line), as compared to soft tissue tumor cell lines such as ML1a (promyelocytic leukemia cell line) and U2OS (osteosarcoma cell line). Cell lines derived from normal tissues, such as NIH-3T3 (mouse fibroblast cell line) and Human Embryonic Kidney (HEK) 293 cells, expressed very little Fortilin (FIG. 3). The expression of Fortilin thus appears to be up-regulated in tumor cells, especially in those of epithelial in origin. This observation, taken together with the fact that Fortilin is an anti-apoptotic protein, suggests that Fortilin may contribute to tumorigenesis by preventing cells that come to possess genetic mutations or abnormalities from being eliminated by apoptosis.

In order to determine the intracellular localization of Fortilin, immunostaining was performed on HeLa cells transiently transfected with FLAG-tagged p21, β-galactosidase (LacZ) or Fortilin. Cells were then fixed, permeablized and stained with anti-FLAG monoclonal antibody and anti-mouse IgG conjugated to Rhodamine Red X. The nuclei were counter stained with DAPI (4,6-Diamidino-2-phenylindole). When probed with anti-FLAG antibody, the FLAG-tagged p21 and LacZ were detected mostly in the nucleus and cytosol, respectively, consistent with previous reports (Taules et al., 1999; Sato & Yamashina, 1975). In this system, the FLAG-tagged Fortilin was found predominantly localized in the nucleus. Immunostaining with the rabbit anti-Fortilin anti-sera characterized above further supported the current results. It has been shown that the main sites of action of Bcl-xL, a Bcl-2 family protein, and XIAP, a member of IAP family, are in the cytosol (Adams & Cory, 1998; Deveraux et al., 1997). It is possible that Fortilin is an anti-apoptotic protein that modulates the nuclear events of apoptosis.

Finally, Fortilin expression was examined in human breast tissue samples. Normal human breast (NB), fibroadenoma (FA), and ductal carcinoma (BC) sections were stained in a single setting, using anti-Fortilin antibody, biotin conjugated goat anti-rabbit antibody, streptavidin-horseradish peroxidase complex, and the DAB (diaminobenzidine) as chromogen. Hematoxylin counterstaining was then performed. Again, Fortilin immunoreactivity (brown color) was highest in the nucleus with minimal signals in the cytosol. Strikingly, tissues from malignant breast ductal cancer showed significantly more Fortilin immunoreactivity as compared to tissues from fibroadenoma or to normal breast tissues.

Stained sections were then subjected to computational antigen quantification using a SAMBA 4000 Image Analysis System. The labeling index represents the number of DAB positive cells divided by total number of cells. The mean optical density, equivalent to mean labeling concentration, is the mean of optical densities of DAB signals in the cells. The integrated score is the double products of the labeling index and mean optical density. As is seen in the graphs of the labeling index, mean optical density and integrated score, the DAB signal score was highest in tissues from malignant ductal carcinoma (BC), followed by fibroadenoma (FA) and normal human breast (NB). A statistically significant linear relationship was present between the degree of malignancy (normal to fibroadenoma to breast cancer) and the mean optical density and integrated score at the 0.05 level. The staining experiments were confirmed by the interactive computational antigen quantification method: both the mean optical density (the average intensity of immunoreactivity signals) and the integrated score (the double products of the labeling index and the mean optical density) were higher in breast cancer tissue than in fibroadenoma and normal breast tissue. Interestingly, it has been shown that invasive breast cancer has reduced Bcl-2 immunostaining compared with normal breast epithelia and preinvasive breast lesions (Daidone et al., 1999). Moreover, high Bcl-2 expression has been shown to associate with a number of favorable prognostic factors (Daidone et al., 1999). In contrast, Survivin, a member of IAP (Inhibitor of Apoptosis Protein) family, is shown to be over-expressed in high-grade non-Hodgkin's lymphoma, but not in low-grade lymphomas (Ambrosini et al., 1997). In addition, the presence of the Survivin in non-small cell lung cancers was associated with the poor clinical outcome (Monzo et al., 1999). Given the fact that Forilin expression was more extensive in the malignant breast cancer tissue, it is possible that the expression of Fortilin, like Survivin, may contribute to the aggressiveness of human neoplasm.

Example 2

Fortilin Specifically Binds p53

Studies were initiated to determine whether p53 and Fortilin specifically interact. Either recombinant GST-Fortilin or GST only were incubated at 4° C. for 90 minutes with in vitro translated, [$^{35}$S-Met]-labeled p53, MCL1 or Bcl-xL, in Binding Buffer (50 mM HEPES, pH7.5, 70 mM KCl, 0.5 mM ATP, 5 mM MgSO$_4$, 1 mM DTT, 0.001% NP40, 50 μM MG132, 2 μg/mL BSA, Aporotinin, PMSF and protease inhibitor cocktail (Sigma Co., St. Louis, Mo.)). The GST or GST-Fortilin was then pulled down with Glutathione Sepharose 4B beads (Amersham-Pharmacia Biotechnologies). Formed complexes were extensively washed and eluted into SDS loading buffer. The eluted proteins were subjected to SDS-PAGE in duplicate. The first SDS gel was stained with Commassie Blue to confirm the successful immunoprecipitation of GST and GST-Fortilin (IP). The second SDS gel was fixed and subjected to fluorography (Co-IP). p53, not Bcl-xL, was co-immunoprecipitated with Fortilin in vitro. MCL1 was co-precipitated with Fortilin. Thus, there is a specific interaction present between Fortilin and p53, between Fortilin and MCL1.

Example 3

Fortilin Inhibits p53-Mediated Apoptosis

Figure 5:
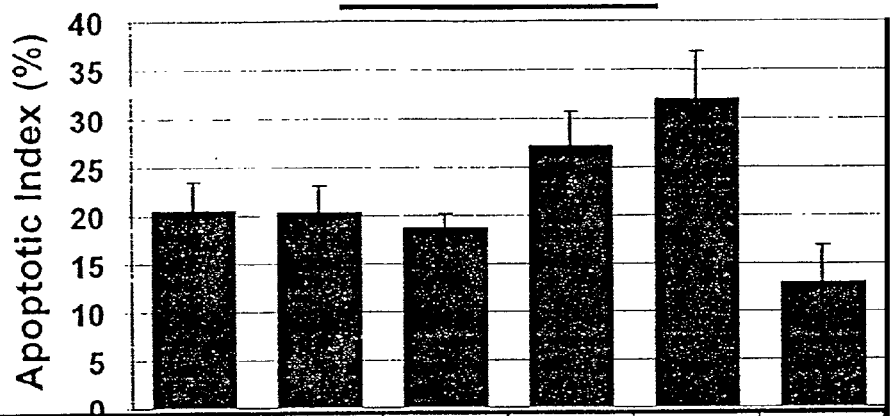
FIG. 5. Fortilin prevents p53-mediated apoptosis in H1299 cells. H1299 cells were transfected with indicated combinations of mammalian expression constructs. Apoptotic index was calculated as (Blue cells with apoptotic plasma membrane morphology)/(Total blue cells counted)×100. There was statistically significant (p<0.001) suppression of p53-induced apoptosis by overexpression of Fortilin, MCL1 and Bcl-2 in H1299 cells. Fortilin(23-172), a truncation of Fortilin representing amino acids 23-172 of Fortilin, did not significantly prevent p53-mediated apoptosis in this system.

Because wild-type p53 can induce apoptosis, the ability of Fortilin to prevent or inhibit p53-mediated apoptosis was examined. H1299 cells were transfected with indicated combinations of mammalian expression constructs. Thirty hours after the transfection, cells were fixed and stained for beta-galactosidase activities. Cells that were round in shape with significant membrane irregularity were counted as apoptotic (FIG. 5). Apoptotic index was calculated as (Blue cells with apoptotic plasma membrane morphology)/(Total blue cells counted)×100. There was statistically significant ($p<0.001$) suppression of p53 induced apoptosis by overexpression of Fortilin, MCL1 and Bcl-2 in H1299 cells. Fortilin(23-172), a mutant of Fortilin representing $23^{rd}$-$172^{nd}$ amino acids of Fortilin, did not significantly prevent p53 mediated apoptosis in this system.

Example 4

Fortilin Reduces Activation of Bax by p53

Figure 6A:
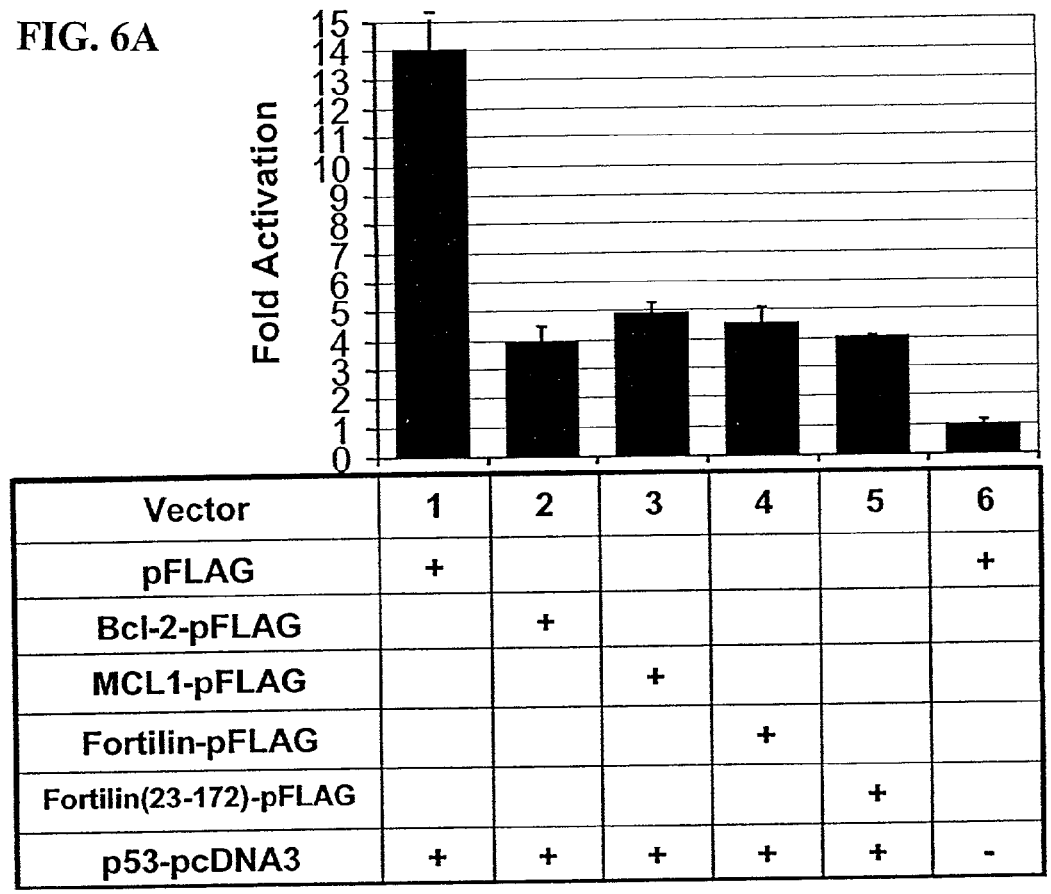
FIGS. 6A-6B. Graphs indicating Fortilin prevents transactivation by p53 of Bax gene in H1299 cells.

The tumor suppressor p53 is a transcription factor that has been shown to transactivate the Bax gene, which is involved in apoptosis. The ability of Fortilin to interfere with transactivation of the Bax gene by p53 was investigated. Non-small cell lung cancer cell line H1299 cells were transfected with p53-pcDNA3, LacZ-pFLAG, p-Bax-RE-Luc (a plasmid encoding the Luciferase gene under the control of the Bax responsive element) and pFLAG vector encoding Bcl-2, MCL1, Fortilin or truncated Fortilin as indicated in FIG. 6. Twenty-four hours after the transfection, luciferase activity was measured and normalized to the β-galactosidase activity, the latter representing transfection efficiency. Bcl-2 has been shown to inhibit p53 transactivation of Bax gene by preventing p53 translocation into the nucleus. MCL1, Fortilin and truncated Fortilin (23-172) inhibited p53 transactivation of Bax gene (FIG. 6A).

Figure 6B:
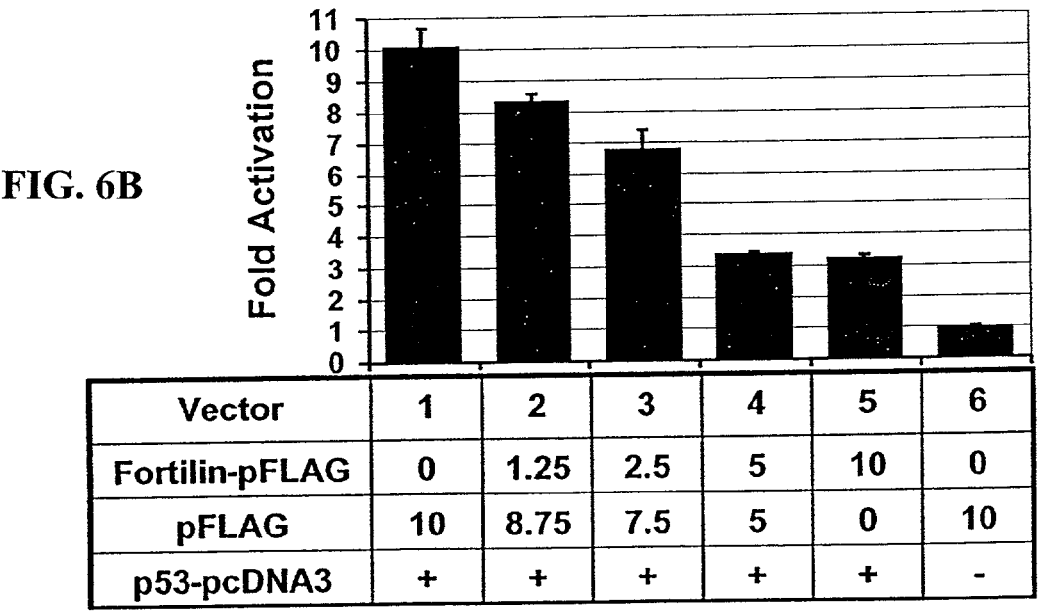

Next, studies were conducted to determine whether the inhibition was dosage dependent. H1299 cells were transfected with p53-pcDNA3, LacZ-pFLAG, p-Bax-RE-Luc and various amount of Fortilin-pFLAG. The total amount of DNA added was adjusted by the addition of empty pFLAG vector. Twenty-four hours after the transfection, luciferase activity was measured and normalized to the β-galactosidase activity. Transfection with a larger amount of Fortilin was associated with larger inhibitory effect on p53 transactivation of Bax gene (FIG. 6B).

Example 5

Fortilin is Upregulated in Atherosclerotic Aorta Tissue

To investigate whether Fortilin is upregulated in human atheroma, human aortae (Atheroma-1 from one patient and Atheroma-2 from the other) were harvested during the aneurysmectomy. The normal control represents normal human aorta from an organ donor. The tissue were frozen immediately after harvest in liquid nitrogen and stored at −80° C. Subsequently the tissue was pulverized while frozen and the proteins were extracted in extraction buffer (10% SDS, 10 mM Tris-HCl, pH 7.6, 20 mM NaCl). The protein concentration was then determined. A total of 7 μg of protein was loaded in each lane of a 12% SDS gel. Following the SDS-PAGE and Western transfer to a nitrocellulose membrane, transferred proteins were probed with anti-actin (clone C4, Roche) and anti-Fortilin antibodies. Fortilin signals were stronger in both samples of atheroma tissue than in normal tissue. An equal amount of protein was analyzed, as shown by an actin control.

Example 6

Fortilin Specifically Interacts with MCL1 in Yeast

Figure 7:
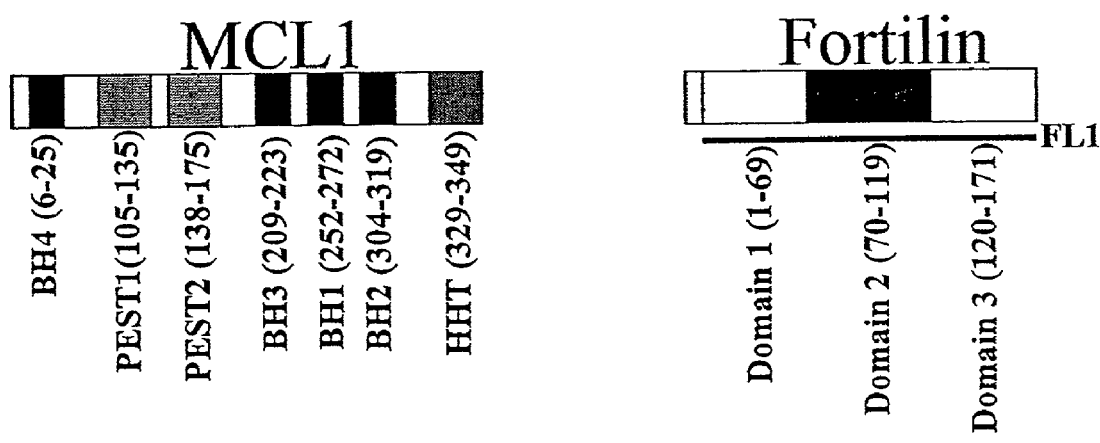
FIG. 7. Constructs used in yeast two-hybrid assay. Domain structures of MCL1 and Fortilin are shown. MCL1 consists of four BH (Bcl-2 homology) domains and two PEST (proline (P), glutamic acid (E), serine (S) and threonine (T)) sequences. "CHT" denotes the C-terminus Hydrophobic Tail. Fortilin consists of three major domains with different hydrophilicity: the Domain 1, 2 and 3.

The yeast two-hybrid system was employed to evaluate any interaction between Fortilin and MCL1. *Saccharomyces cerevisiae* SFY526 cells were co-transformed with pAS2.1 or pAS2.1-MCL1 and pGAD GH or pGAD GH-FL1, the $5^{th}$-$172^{st}$ amino acids of Fortilin. Transformed cells were selected on SD/-Trp/-Leu plates. Grown colonies on these selection plates were subjected to a X-gal filter lift assay, as the reporter gene was X-gal under the control of a promoter containing the element recognized by the DNA binding domain. X-gal activity was observed when amino acids 5-172 of Fortilin fused to a transactivating domain and MCL1 fused to a DNA binding domain were transfected into yeast. FIG. 7 shows the domain structures of MCL1 and PCNA. MCL1 consists of four BH (Bcl-2 homology) domains and two PEST (proline (P), glutamic acid (E), serine (S) and threonine (T)) sequences. "CHT" denotes the C-terminus Hydrophobic Tail. Fortilin consists of three major domains with different hydrophilicity: the Domain 1, 2 and 3.

An in vitro binding assay to evaluate MCL1/Fortilin binding was employed. The in vitro translated, [$^{35}$S-Met]-labeled influenza hemagglutinin-tagged Fortilin (Fortilin-HA) and another in vitro translated, [$^{35}$S-Met]-labeled protein, as indicated in the figure, were incubated at 4° C. for 90 minutes. Fortilin-HA was then pulled down with rat anti-HA monoclonal antibody and sheep anti-rat polyclonal antibody conjugated to Dynabeads™ (Dynal USA). Immune complexes were extensively washed, subjected to SDS-PAGE and visualized by fluorography and a phosphoimager system. MCL1, and not PCNA, was co-immunoprecipitated with Fortilin in vitro.

The total cell lysate from 2×10 (Zhou et al., 1997) COS cells transfected with indicated plasmids were incubated either with rat anti-HA monoclonal antibody (Roche) or a control monoclonal antibody. After a 2 hour incubation, goat anti-rat IgG conjugated to Dynabeads™ was added, and the mixtures were incubated for additional one hour. After extensive wash, the precipitated complexes were eluted to SDS gel loading buffer, separated on 12% SDS-PAGE, and subjected to Western blotting and immuno-probing with anti-HA and anti-FLAG antibodies. Total cell lysates contained abundant amount of FLAG-MCL1 and Fortilin-HA. Fortilin-HA was successfully immunoprecipitated by anti-HA antibody, but not by control antibody. FLAG-MCL1 was co-precipitated only in the presence of immunoprecipitated Fortilin-HA. Taken together, this data indicates there is a specific interaction between Fortilin and MCL1 in vivo.

Example 7

Biochemistry of Fortilin-MCL1 Interaction

The binding between in vitro translated, [$^{35}$S-Met]-labeled influenza hemagglutinin tagged Fortilin (Fortilin-HA) and other in vitro translated, [$^{35}$S-Met]-labeled protein (i.e. MCL1, Bcl-xL, Bak, Bax or PCNA) was assessed in the system described in Example 6. Only MCL1, and not Bcl-xL, Bak, or Bax, was co-immunoprecipitated with Fortilin in vitro. Furthermore, only the $5^{th}$-$22^{nd}$ amino acids of Fortilin are necessary for the Fortilin-MCL1 interaction. The binding between in vitro translated, [$^{35}$S-Met]-labeled influenza hemagglutinin tagged Fortilin (Fortilin-HA), or truncated Fortilin, and another in vitro translated, [$^{35}$S-Met]-labeled protein (i.e. MCL1 or Bcl-xL) was assessed. Only full-length Fortilin and Fortilin (5-172), but not Fortilin (23-172), Fortilin (46-172), or Bcl-xL, co-immunoprecipitated MCL1 in vitro. MCL1 is unique among Bcl-2 family member proteins in its ability to interact with Fortilin.

Example 8

Figure 8:
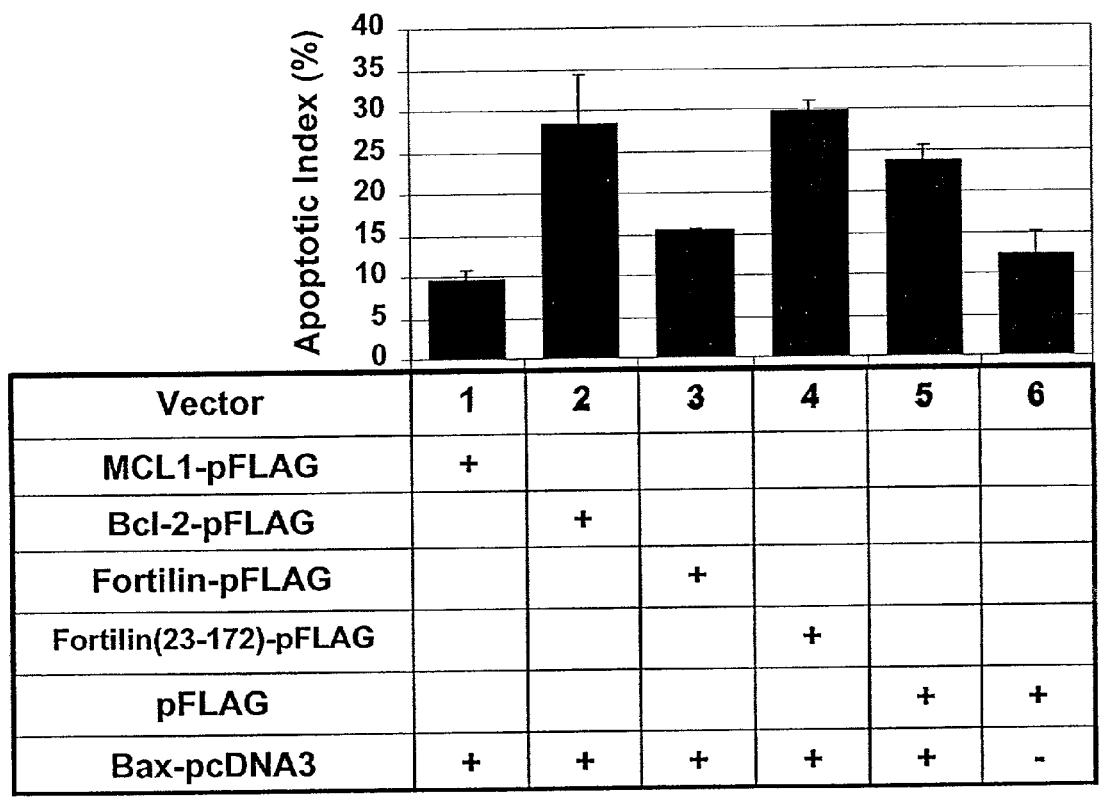
FIG. 8. Graph showing inhibition of Bax-mediated apoptosis by Fortilin. Osteosarcoma cell line U2OS cells were transfected with Bax-pcDNA3, LacZ-pFLAG, and various plasmids indicated in the figure. Cells were stained with X-gal. Blue cells represented cells expressing Bax, β-galactosidase, and indicated proteins in question. Apoptotic index was calculated as the number of blue apoptotic cells divided by the number of total blue cells counted, expressed in percentage.

Fortilin-MCL1 Interaction is Necessary for Fortilin to Prevent Bax-Mediated Apoptosis Osteosarcoma cell line U2OS cells were transfected with Bax-pcDNA3, LacZ-pFLAG and various plasmids indicated in FIG. 8. The amount of LacZ-pFLAG was 1/10 to 1/20 (w/w) of total amounts of DNA added. Thirty hours after the transfection, cells were stained with X-gal. Blue cells represented cells expressing Bax, β-galactosidase and indicated proteins in question. At least 300 blue cells were counted and evaluated for plasma membrane morphology. Rounded cells were counted as apoptotic. Apoptotic index was calculated as the number of blue apoptotic cells divided by the number of total blue cells counted, expressed in percentage. Without the expression of Bax, there was a modest amount of background cell death noted (Lane 6). On the other hand, the presence of Bax caused 2 holds increase in the number of apoptotic cells (Lane 5). An anti-apoptotic protein MCL1 prevented cells from undergoing Bax mediated apoptosis. In this system, wild type Fortilin suppressed Bax induced cell death. Strikingly Fortilin (23-172), a Fortilin mutant that lacks MCL1 binding, failed to prevent cells from undergoing Bax mediated apoptosis in this system. Taken together, the ability of Fortilin to inhibit Bax mediated apoptosis is mediated by its interaction with MCL1.

In summary, Fortilin is a predominantly nuclear protein with anti-apoptotic function, which is also highly conserved among species and distributed widely in normal tissues. The expression of Fortilin appears to be more abundant in cancerous cell lines and tissues with a higher degree of malignancy. These data suggest that Fortilin may play an important role in tumorigenesis and resistance of cancer cells to chemotherapeutic agents through its anti-apoptotic function. Since Fortilin has no sequence homology to the two major classes of anti-apoptotic molecules, i.e., Bcl-2 and IAP family proteins, it is possible that Fortilin may represent a member of a novel anti-apoptotic family.

Example 9

Identification of Inhibitors of p53-Fortilin Interaction

To identify inhibitors of the p53-Fortilin interaction, an in vitro assay will be employed. To implement the assay, recombinant Fortilin will be coated on 96-well plates. A candidate substance (either polypeptides, peptides, or small molecules) dissolved in phosphate buffered saline (PBS) will be added to the wells and incubated in the presence of recombinant p53. A PBS only Negative control will be included. Wells will then be washed with PBS. Diluted anti-p53 antibody conjugated to horse raddish peroxidase (HRP) will be added to wells and incubated. Wells will be washed again with PBS. Diluted substrate of HRP will be added. Absorbance will be determined using a spectrophotometer.

Once promising compounds are identified, related compounds and compounds with various modification will be also tested. The best compound among the class will be subjected to in vivo testing to confirm the ability of a candidate substance to inhibit the p53-Fortilin interaction. To do this, a Stable transfection will be established in mammalian cells. These cells will have stably transfected plasmids: i) A plasmid to produce the GAL4-DNA-BD (binding domain)-Fortilin; ii) A plasmid to produce the VP16-DNA-AD (activating domain)-p53; and iii) A reporter plasmid that contain beta-galactosidase reporter gene under the control of a GAL4-responsive element and the minimal promoter of the adenovirus E1b.

The transfected cells will be seeded on 96 well plates. Candidate compounds will be disolved in PBS (pH=7.4), added to the media, and incubated before cells are assayed for β-galactosidase activity. The lower the activity of β-galactosidase, the higher the inhibitory effect of the candidate compound.

Several strategies may be employed to design or identify candidate compounds. Determining which regions of Fortilin are important for the p53 binding is one strategy. Polypeptides that are identical or similar to the amino acid sequence of the region(s) of Fortilin that are necessary for the p53 binding will be candidate molecules. Another strategy involves determining ternary structures of such polypeptides by computational analysis and designing the small molecules that would mimic such ternary structures. Importantly, Fortilin expression is higher in cancerous tissue. Thus, effect of such disruption would be greatest in cancerous tissue, suggesting there would be selective intervention in cancerous tissue.

Example 10

Identification of Inhibitors of MCL1-Fortilin Interaction

A similar system and principle as described in Example 9 can be used to discover the compound(s) that interfere with the Fortilin-MCL1 interaction. Fortilin that lacks the MCL1 binding region does not prevent Bax-mediated apoptosis. Therefore, Fortilin may bind MCL1 to protect cells from Bax-induced apoptosis. Molecules that disrupt Fortilin-MCL1 interaction would have pro-apoptotic effects through the facilitation of Bax-mediated cell death.

Example 11

Diagnostic Method to Assess the Aggressiveness of Cancer

An anti-Fortilin antibody in rabbits, using $90^{th}$-$111^{th}$ amino acids of Fortilin as an antigen was characterized, showing good sensitivity and specificity to recognize human Fortilin (FIG. 3). Human breast tissue, including normal breast tissue, fibroadenoma and ductal breast cancer was stained using the antibody. As described above, the Fortilin signal was strongest in malignant ductal breast cancer, followed by in fibroadenoma and normal breast tissue. Fortilin expression may correlate with the degree of malignancy at least in breast tissue. Data reported herein suggest that the degree of Fortilin expression can be used to assess the degree of malignancy of human cancers and to estimate the prognosis of patients with such cancers. To do this, Breast tissue will be fixed in formalin and embedded in a standard fashion in paraffin. Tissue is stained, with normal breast tissue as a control, using the anti-Fortilin antibody with DAB as a chromogen. The level of Fortilin expression will be assessed either visually or using computational antigen quantification methods.

Example 12

Fortilin Binds p53 in Stably Transfected U2OS Cells

As in example 2, studies were initiated to determine whether p53 and Fortilin specifically interact in U2OS cells.

Six million U2OS cells stably expressing either HA-fortilin or HA-only were suspended in lysis-binding-wash buffer (50 mM HEPES, pH7.5, 70 mM KCl, 0.5 mM ATP, 5 mM MgSO4, 1 mM DTT, 0.1% NP40, 2 mg/mL BSA, Aprotinin, PMSF, MG132 and protease inhibitor cocktail). Cells were then mechanically disrupted by nitrogen excavitation method. Cleared total cell lysates were incubated with 20 mg anti-HA antibody (3F10, Roche), followed by the incubation with anti-mouse IgG conjugated to magnetic beads (Dynal USA) and extensive wash with lysis-binding-wash buffer. Finally, formed complexes were eluted into SDS-loading buffer and subjected to SDS-PAGE, Western transfer and immunodetection using anti-p53 and anti-HA antibodies. In the presence of adequate inputs of p53 and HA-fortilin, the presence of fortilin was necessary and sufficient for the co-precipitation of p53.

Further experiments were conducted to determine in vivo immunoprecipitation of fortilin by p53. Twenty million U2OS cells were suspended in lysis-binding buffer (50 mM HEPES, pH7.5, 70 mM KCl, 0.5 mM ATP, 5 mM MgSO4, 1 mM DTT, 0.001% NP40, 2 mg/mL BSA, Aprotinin, PMSF, MG132 and protease inhibitor cocktail). Cells were then mechanically disrupted by nitrogen excavitation method. Cleared total cell lysates were divided equally into two eppendorf tubes. To the first tube, anti-p53 antibody (DO-1, 10 mg) was added, while 20 mg control monoclonal antibody was added to the second tube. After incubation, formed complexes were precipitated by goat anti-mouse IgG conjugated to magnetic beads (Dynal USA), followed by extensive wash. Finally, formed complexes were eluted into SDS-loading buffer and subjected to SDS-PAGE, Western transfer and immunodetection using anti-p53 and anti-fortilin antibodies. The presence of immunoprecipitated p53 was necessary and sufficient to co-precipitate fortilin. Thus, there is a specific interaction between fortilin and p53 in vivo.

Example 13

Apoptotic Activity of Fortilin in Stably Transfected U2OS Cells

Figure 9A:
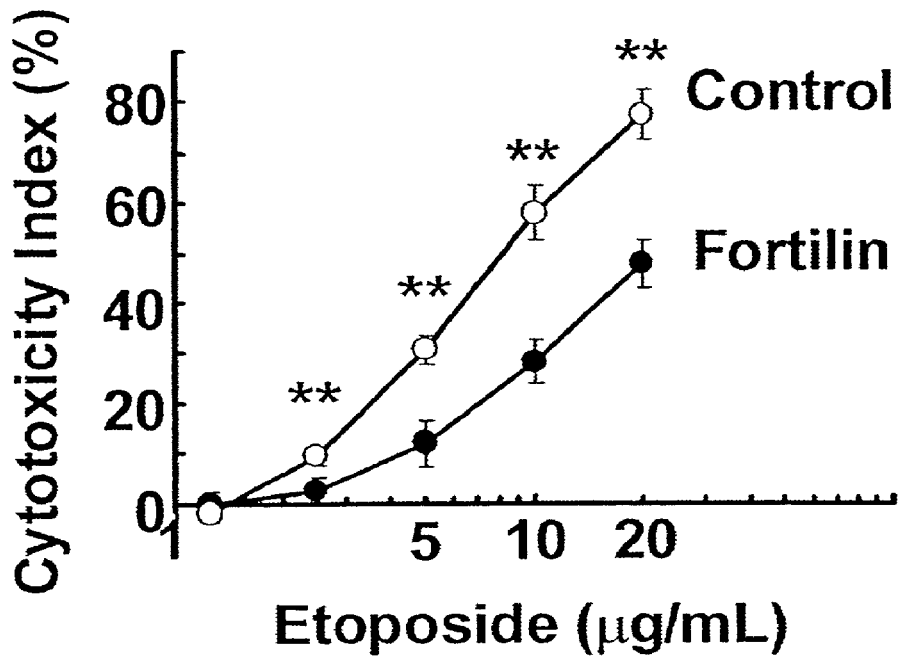
FIGS. 9A-9B. Inhibition of etoposide-induced cell death by stable expression of fortilin in U2OS cells. U2OS cells were stably transfected with either pcDNA6-fortilin ("Fortilin") or empty pcDNA6 ("Control") and selected by blasticidine. Cells were seeded in a 96-well plate in quadruplicate and either challenged by FIG. 9A various doses (0, 2.5, 5, 10 and 20 μg/mL) of etoposide for 48 hours or FIG. 9B 5 μg/mL of etoposide for various time periods (0, 1, 2, 3 and 4 days). In both cases, the cell media were assayed for the lactate dehydrogenase (LDH) activity released from the cytosol of damaged cells, using a cytotoxicity detection kit (Roche Molecular Biochemicals), according to the manufacturer's instructions. The cytotoxicity index was calculated as follows: (LDH activity in the media−background LDH activity)÷(LDH activity in the medium of the cells lysed by 1% Triton X-100−background LDH activity)×100. Fortilin overexpression was associated with significantly lesser amounts of etoposide-induced cytotoxicity at the concentrations of 2.5, 5, 10, and 20 μg/mL (**, P<0.001) FIG. 9A. Fortilin overexpression was also associated with lesser amounts of etoposide-induced cytotoxicity after incubation periods of 48, 72, and 96 hours (*, P<0.05; **, P<0.001) FIG. 9B. Western blot analysis confirmed the presence of overexpressed fortilin in cells.
Figure 9B:
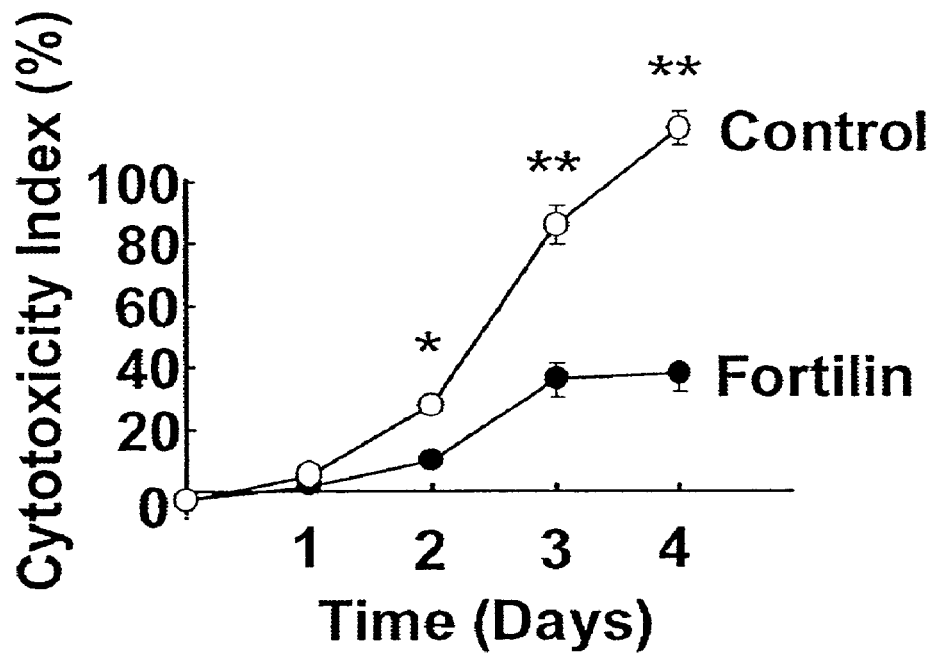

The apoptotic activity of Fortilin was confirmed using a different cell line and a different cell death detection system. U2OS cells stably expressing Fortilin (U2OS.F) were generated and compared with control U2OS cells stably possessing empty pcDNA6 vector (U2OS.E) for their ability to withstand etoposide-induced cytotoxicity, using a standard LDH cytotoxicity assay as described in Methods. As shown in FIG. 9A, the stable expression of Fortilin in U2OS cells was associated with significantly less cytotoxicity over the wide range of etoposide concentrations (2.5, 5, 10, and 20 μg/mL; all , $P<0.001$) (FIG. 9A). Furthermore, U2OS.F exhibited significantly less cytotoxicity at various time points after the etoposide challenge (48 hours, $P<0.05$; 72 and 96 hours, $P<0.001$) (FIG. 9B). Taken together, these results suggested that Fortilin is an anti-apoptotic protein that prevents etoposide-induced cell death.

Example 14

Caspase-3-like Activity in Fortilin-Overexpressing Cells

Figure 10A:
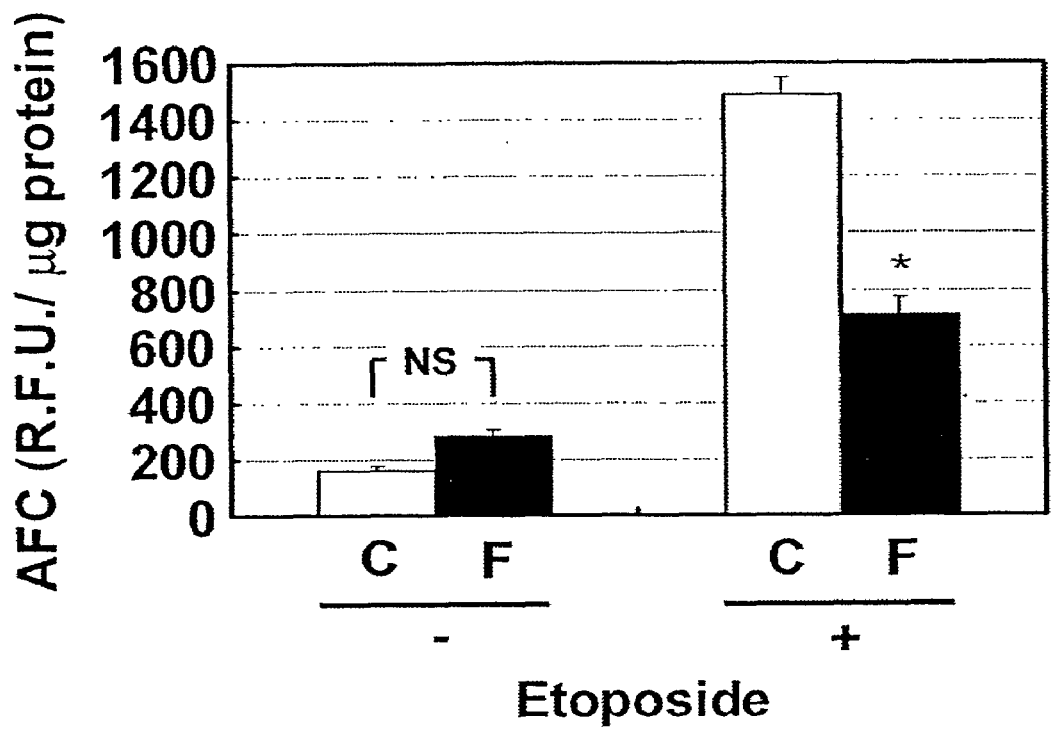
FIGS. 10A-10B. Inhibition of caspase-3-like activity by fortilin in etoposide-challenged U2OS cells.
Figure 10B:
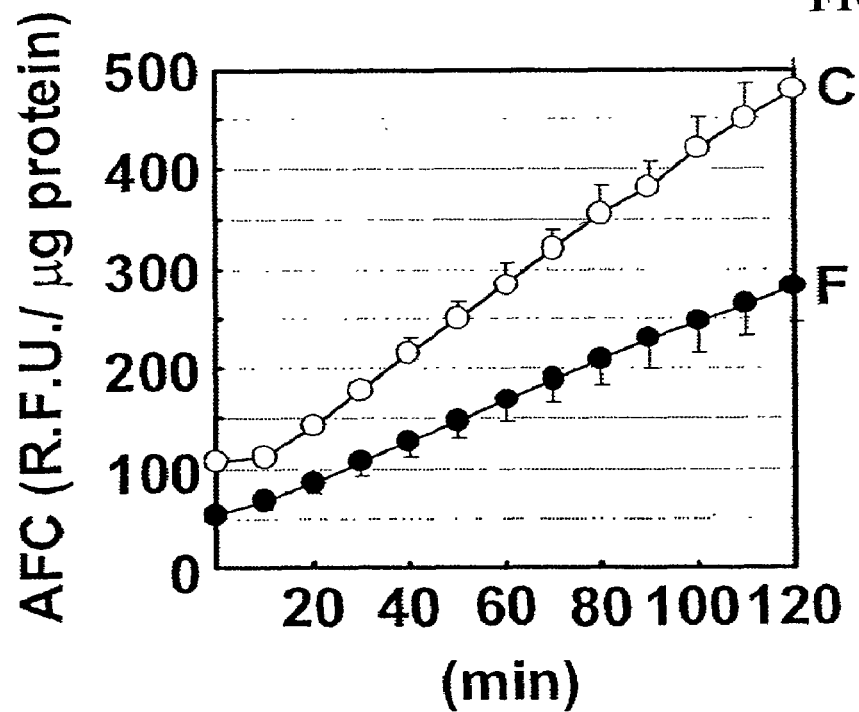

To further explore the role of Fortilin in apoptosis regulation, the status of caspase-3-like activity in Fortilin-overexpressing cells upon etoposide challenge was examined. In brief, the caspase-3-like activity of the U2OS cells stably expressing Fortilin (U2OS.F) as described above was compared with that of the control U2OS cells (U2OS.E) when challenged with etoposide. As shown in FIG. 10A, in the absence of etoposide challenge (FIG. 10A, "Etoposide −"), the caspase-3-like-activities of U2OS.E (FIG. 10A, "C") and U2OS.F (FIG. 10A, "F") were similarly low (158.2±18.0 and 283±22.6 for U2OS.E and U2OS.F, respectively; not statistically significant, "NS") FIG. 10A). When these cells were challenged with etoposide (FIG. 10A, "Etoposide +"), however, U2OS.E exhibited a 9.4-fold increase in the activity with caspase-3-like activity index reaching 1488.1±58.7, while the caspase-3-like activity index of U2OS.F remained at 713.9±62.6 ($P<0.05$) (FIG. 10A, asterisk). Consistently, the caspase-3-like activities of etoposide challenged U2OS.E were always higher than, and diverged continuously from, those of U2OS.F during the two-hour period of the kinetics assay (FIG. 10B). Together, these data suggested that the protection by Fortilin against etoposide-induced cytotoxicity, as assessed by LDH assay (FIGS. 10A-10B), was at least partially due to the prevention of caspase-3 activation by Fortilin, an antiapoptotic molecule.

Example 15

Antiapoptotic Role of Fortilin in MCF-7 Cells

Figure 11:
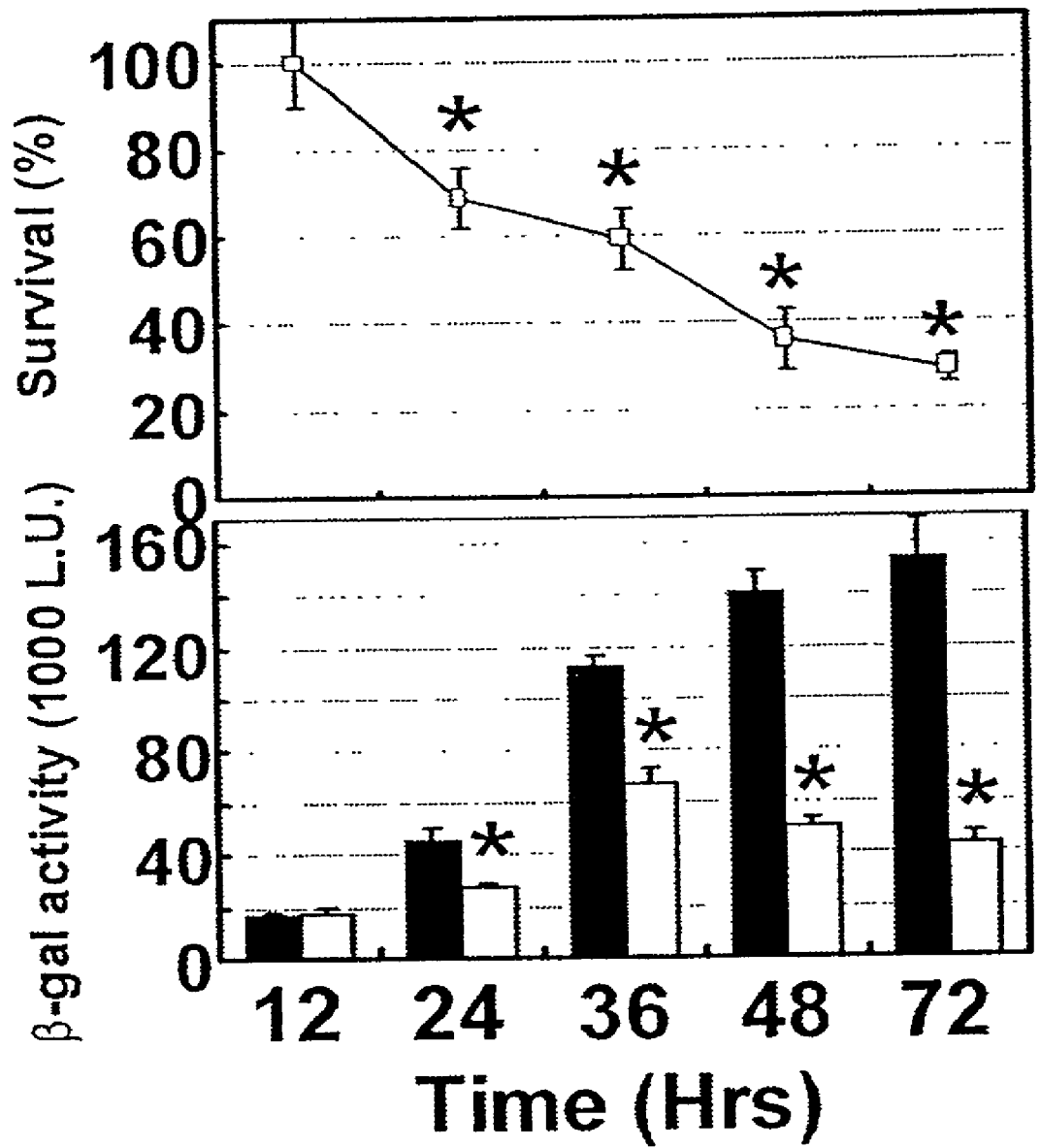
FIG. 11. The anti-cell death activity of fortilin in MCF-7, a human breast ductal cardinoma cell line. The reduction of intracellular fortilin concentration by antisense fortilin treatment: To test the antiapoptotic role of fortilin in MCF-7 cells, the effect of fortilin depletion by antisense fortilin treatment on the survival of MCF-7 cells was studied. The intracellular concentration of fortilin was evaluated in MCL-7 cells that were treated and compared with that from control cells, using Western blot analysis of total cell lysates by anti-actin and anti-fortilin antibodies. The antisense fortilin treatment, using a pFLAG vector containing the antisense fortilin polynucleotide sequence (pFLAG-antisense-fortilin), significantly reduced the intracellular concentration of fortilin. The induction of spontaneous MCF-7 cell death by antisense fortilin treatment was then assessed: MCF-7 cells were transfected with either pFLAG-antisense fortilin or empty pFLAG, along with pFLAG-LacZ used as a transfection-survival marker. Cells were harvested at the indicated times, assayed for β-galactosidase, and the survival index was calculated. L.U. denotes the light units. Asterisks in the survival curve indicate statistically significant (P<0.01) reduction in survival rate relative to that at 12 hours. Asterisks in the β-galactosidase activity indicate statistically significant (P<0.01) differences in the activity between antisense-treated cells (open bars) and control cells (closed bars).

The effect of Fortilin depletion by antisense Fortilin treatment on the survival of MCF-7 cells, a malignant human ductal carcinoma cell line, was studied. Antisense Fortilin treatment, using a pFLAG vector containing the antisense Fortilin polynucleotide sequence (pFLAG-antisense-Fortilin), was shown to significantly reduce the intracellular concentration of Fortilin, by Western blot analysis. MCF-7 cells were thereby transiently transfected with either an empty pFLAG vector or pFLAG-antisense-Fortilin along with pFLAG-LacZ as a transfection-survival marker. Cells were harvested at various time points, and assayed for β-galactosidase activity. MCF-7 cells that had been transfected with the empty pFLAG vector and pFLAG-LacZ accumulated β-galactosidase intracellularly over time, as evidenced by the increase in β-galactosidase activities at 24, 36, 48 and 72 hours (FIG. 11, lower panel, closed bars). In contrast, MCF-7 cells that had been transfected with pFLAG-antisense Fortilin and pFLAG-LacZ had significantly less β-galactosidase activity than did the control cells at these time points (FIG. 11, lower panel, open bars, $P<0.01$ for 24, 36, 48 and 72 hours). The survival of the antisense-treated cells, calculated as the ratio of β-galactosidase activities of the antisense-treated and control cells, dropped drastically from 100% to 29% over 72 hours (FIG. 11, upper panel, $P<0.01$ for all time points in comparison with 12-hour time point). Thus, the antisense depletion of Fortilin caused MCF-7 cells to undergo spontaneous and massive cell death. The presence of high intracellular levels of Fortilin may allow aberrant cells to escape the normal tumor surveillance system to propagate and form tumors, perhaps through the inhibition of protective apoptosis.

Example 16

Intracellular Colocalization of MCL1 and Fortilin in U2OS Cells

To determine the intracellular localization of Fortilin in relation to that of MCL1, U2OS cells stably expressing Fortilin-HA that had been seeded on glass cover slides were fixed with 4% paraformaldehyde in phosphate-buffered saline (PBS), treated with an methanol-acetone mixture at −20° C. and probed with rabbit anti-MCL1 polyclonal antibody and mouse anti-HA antibody. Bound antibodies were detected by goat anti-rabbit and anti-mouse IgG conjugated to rhodamine Red X and Cy-2, respectively. Stained cells were analyzed on a Zeiss 210 confocal laser scanning microscope (63×objective). Fortilin expression occurred predominantly in the nucleus. There was no significant Fortilin expression present in either the cytosol or nucleolus. The pattern of MCL1 expression was very similar pattern to that of Fortilin: predominantly nuclear, but outside the nucleolus. Superimposition of both signals showed that most colocalization occurred in the nucleus but outside the nucleolus. These findings indicated that Fortilin and MCL1 were both present in the same intracellular compartment, i.e., in the nucleus, and thus capable of interacting with each other. Furthermore, the data suggest that the MCL1-Fortilin interaction might take place in the nucleus.

Example 17

Fortilin Expression Temporally Correlates with MCL1 Expression in Serum-Stimulated Human Aortic Vascular Smooth Muscle Cells.

Figure 12:
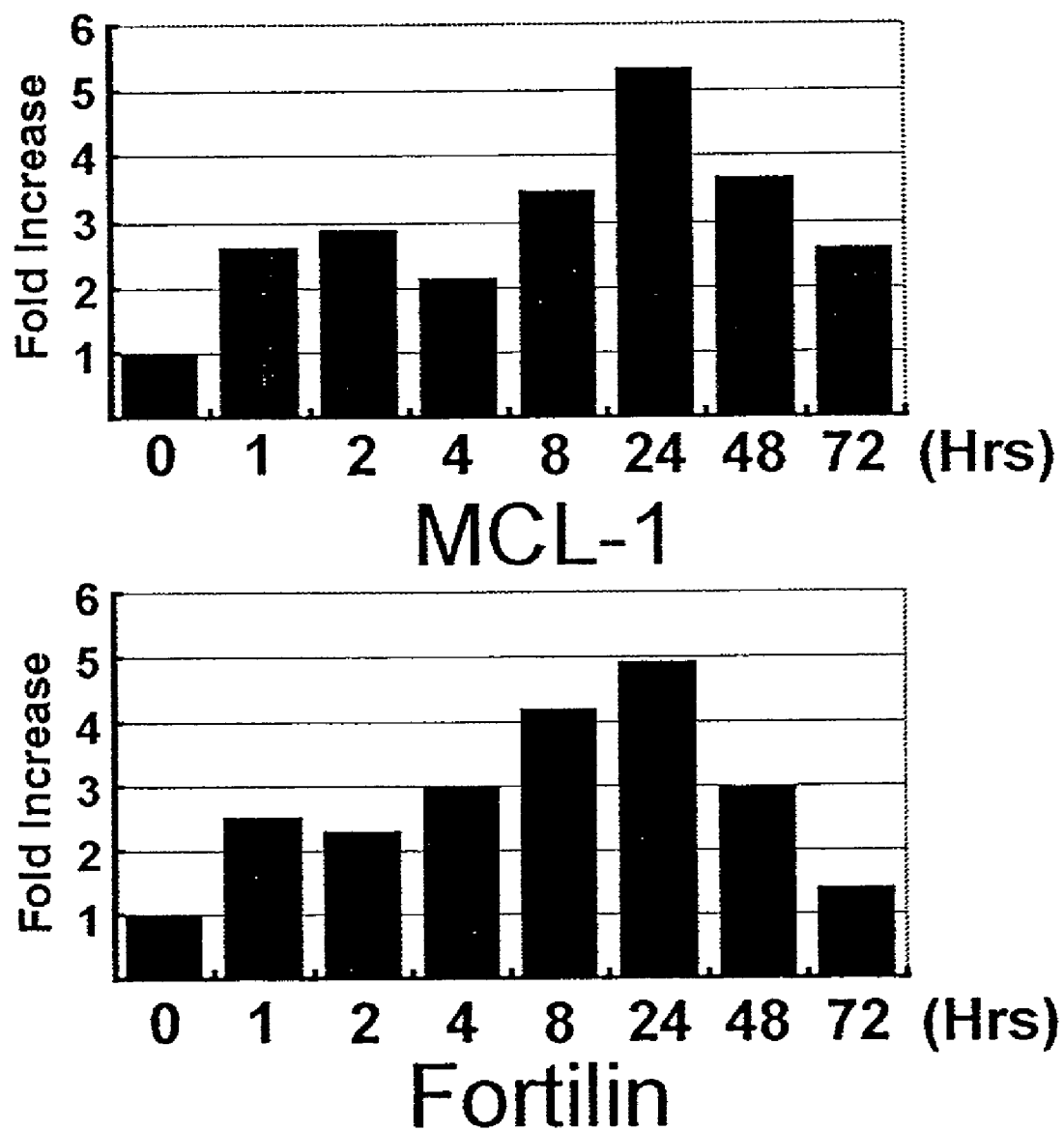
FIG. 12. Similar temporal expression patterns of MCL1 and fortilin in serum-stimulated human aortic vascular smooth muscle cells. Human aortic vascular smooth muscle cells ($1\times10^6$) were seeded on each of eight 10-cm tissue culture dishes. Cells were made quiescent in serum-deprived media for 48 hours. At the end of 48 hours, the cells in the first dish were harvested (Time 0). Media from all the other dishes were then exchanged for the one supplemented by serum. Cells were harvested at 1, 2, 4, 8, 24, 48 and 72 hours after the media change. Western blot analysis using anti-MCL1, anti-fortilin and anti-actin antibodies (upper 3 panels), followed by computer-assisted densitometric analysis (lower 2 panels), showed that both MCL1 and fortilin expression drastically increased over 24 hours of serum stimulation. Taken together, the data indicate that the temporal expression patterns of MCL1 and fortilin in serum-stimulated human aortic vascular smooth muscle cells are similar, consistent with a biologically significant interaction between MCL1 and fortilin.

Although MCL1 is a member of the bcl-2 family, it is unique in being inducible by a number of growth factors including sera. Therefore, upregulation MCL1 expression in serum-stimulated human vascular smooth muscle cells was examined. To this end, cultured human aortic vascular smooth muscle cells that had been made quiescent in serum-free media were stimulated by serum, and the status of MCL1 expression was evaluated at various time points by Western blot analysis using anti-MCL1 antibody. As shown in FIG. 12, MCL1 expression was minimal in quiescent vascular smooth muscle cells (Time 0). The expression of MCL1 rapidly increased, however, upon serum stimulation and peaked around 24 hours (FIG. 12). Therefore, it was hypothesized that if Fortilin functionally interacted with MCL1, then the response pattern of Fortilin to serum-stimulation might be similar to that of MCL1 in this system. Accordingly, the expression status of Fortilin was evaluated by Western blot analysis using anti-Fortilin antibody. The expression of Fortilin was modest in quiescent vascular smooth muscle cells (Time 0) but upregulated upon serum stimulation and maximal around 24 hours (FIG. 12). Thus, the temporal expression pattern of Fortilin was essentially identical to that of MCL1 in serum-stimulated vascular smooth muscle cells. The data indicates that MCL1 is likely a physical and functional protein partner of Fortilin that supports the biological functions of Fortilin.

Example 18

Fortilin Overexpression Does Not Change the Intracellular Concentration of MCL1

Figure 13:
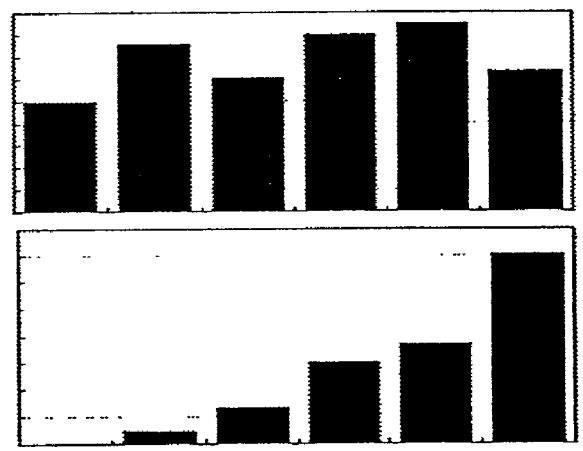
FIG. 13. The absence of change in intracellular MCL1 concentration by fortilin overexpression. In order to test whether fortilin would affect the intracellular concentration of MCL1, U2OS cells were transduced with various amount of adenoviral vector encoding FLAG-tagged fortilin (Ad. FLAG-fortilin). The expression of fortilin, MCL1 and actin was evaluated by Western blot analysis, using anti-FLAG, anti-MCL1 and anti-actin antibodies, respectively, and subjected to a quantitative signal analysis (Quantity One, Bio-Rad). MCL1 and fortilin expression indices were calculated as described in Methods. The intracellular concentration of MCL1 did not significantly change upon forced expression of fortilin.

In order to test whether Fortilin would affect the intracellular concentration of MCL1, U2OS cells were transduced with various amount of plaque-purified adenoviral vector encoding FLAG-tagged Fortilin (Ad.FLAG-Fortilin) and the expression of MCL1 examined by Western-blot analysis. When increased amount of Ad.FLAG-Fortilin was used to transduce U2OS cells, the amount of Fortilin expression in U2OS cells increased drastically (FIG. 13, Fortilin Expression Index). In this system, however, the intracellular concentration of MCL1, as assessed by Western blotting with anti-MCL1 antibody, did not significantly change (FIG. 13, MCL1 Expression Index). These data suggest that Fortilin does not have significant effect on the intracellular concentration of MCL1. It is thus unlikely that Fortilin's anti-apoptotic effect is through its increasing the intracellular concentration of an anti-apoptotic protein MCL1.

Example 19

Fortilin Overexpression Does Not Change the Intracellular Localization of MCL1

In order to determine whether the overexpression of Fortilin would affect the intracellular localization of MCL1, HA-tagged Fortilin (pcDNA-Fortilin-HA) was transiently overexpressed in U2OS cells. Cells were then immunocytochemically evaluated for the intracellular distribution of MCL1, using anti-HA and anti-MCL1 antibodies. The nucleus was counterstained by 4,6-diamidino-2-phenlindole (DAPI). In the cells transfected with empty pcDNA6 vector, MCL1 was typically localized in nucleus, consistent with previous reports (Moulding et al., 1998; Fujise et al., 2000). When cells are transfected with pcDNA6 vector containing Fortilin-HA, MCL1 was consistently localized in the nucleus just as it was in the cells transfected with empty vector. Notably, among the cells treated with pcDNA6-Fortilin-HA-FuGene6 complex, the MCL1 localization was identical both in cells that took up the plasmid and overexpressed Fortilin-HA and in the cell that did not take up the plasmid. Taken together, it is likely that Fortilin will not affect the intracellular localization of MCL1. It may be safe to say, therefore, that Fortilin does not exert its anti-apoptotic effect through its modification of the intracellular localization of an anti-apoptotic protein MCL1.

Example 20

Fortilin Interacts with MCL1 Through its N-Terminus Region

Figure 14:
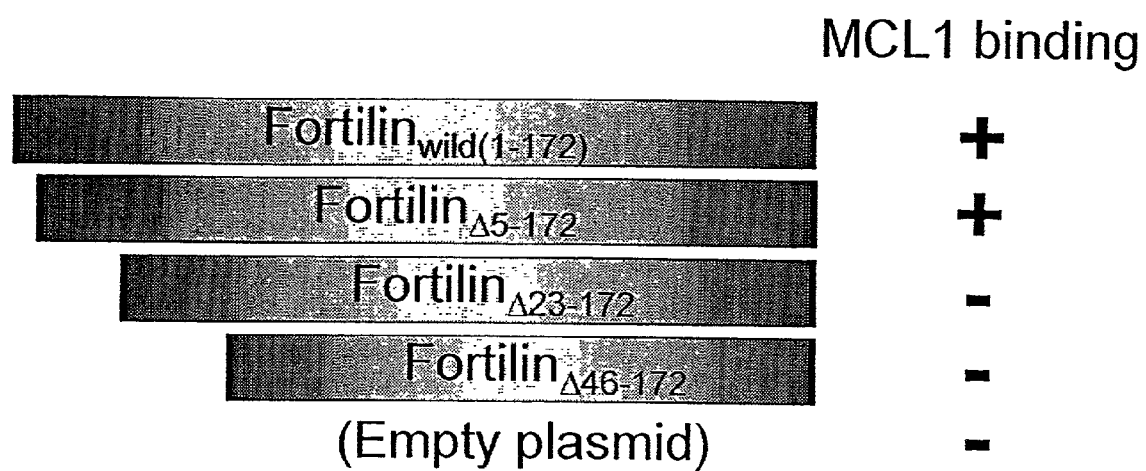
FIG. 14. The binding to MCL1 of various fortilin mutants: The summary of the interaction between MCL1 and fortilin or its mutants is shown. (+): the presence of specific interaction between MCL1 and fortilin/fortilin mutants. (−): the absence of specific interaction between MCL1 and fortilin/fortilin mutants.

To determine which part of Fortilin was critical for binding with MCL1, various Fortilin deletion mutants were constructed and tested for their ability to interact with MCL1 in vitro. MCL1 interacted with full-length Fortilin (amino acids 1-172) and Fortilin$_{\Delta 5-172}$, but not with Fortilin$_{\Delta 23-172}$ or Fortilin$_{\Delta 46-172}$. The data suggested that the N-terminus amino acids 5-22 of Fortilin (RDLISHDEMFSDIYKIRE) (SEQ ID NO:12) was necessary for binding with MCL1 (FIG. 14).

Example 21

Generation and Characterization of Stable Fortilin Mutant Transfectants

In order to elucidate the functional significance of MCL1-Fortilin interaction, stable U2OS transfectants that express various Fortilin deletion mutants were generated. U2OS cells were chosen because they express much less Fortilin than other cell types do. The same plasmids used to evaluate the in vitro interaction with MCL1 (FIG. 14), were transfected into U2OS cells. These mutants were then characterized by immunocytochemistry, Western blot analysis and immunoprecipitation assay.

To assess the intracellular localization of various Fortilin deletion mutants, U2OS cells stably transfected with plasmids encoding HA-tagged wild-type Fortilin, Fortilin$_{\Delta 5-172}$, Fortilin$_{\Delta 23-172}$, or Fortilin$_{\Delta 46-172}$ were probed with mouse anti-HA antibody and goat anti-mouse IgG conjugated to rhodamine Red X. Their nuclei were counterstained with DAPI (4,6-diamidino-2-phenlindole; Sigma). Parents U2OS cells stably transfected with empty vectors served as a negative control. Stained cell were examined under a Zeiss fluorescent microscope. The Fortilin mutants, regardless of their ability to interact with MCL1, localized in the nucleus. This result is important because it assures, to a reasonable extent, that the folding of these mutants was sufficiently similar to that of the wild type and that they were transported to the proper intracellular location.

Figure 15:
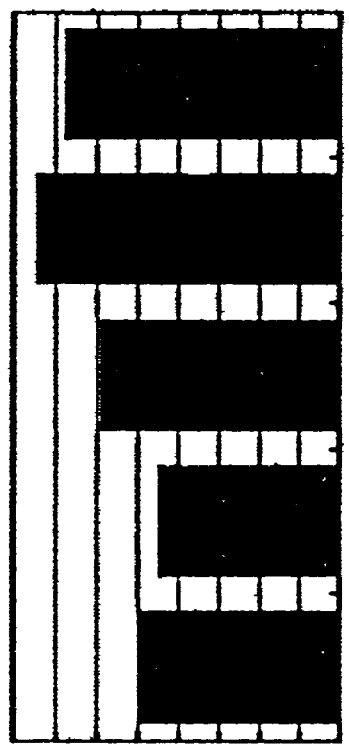
FIG. 15. Generation and characterization of fortilin stable transfectants expressing fortilin deletion mutants. To characterize the fortilin mutants, lysates from U2OS cells stably transfected with plasmids encoding HA-tagged wild-type fortilin, fortilin$_{\Delta 5-172}$, fortilin$_{\Delta 23-172}$, or fortilin$_{\Delta 46-172}$ were subjected to Western blot analysis using anti-actin, anti-MCL1 and anti-HA antibodies. The sizes of fortilin mutants expressed by stable transfectants were all appropriate. Regardless the kind of fortilins expressed, the expression of MCL1 was very similar as indicated by the comparable MCL1 expression indices among lysates.

The expression of mutant protein expression was further confirmed by Western-blot analysis. Lysates from $5\times10^4$ wild type Fortilin and mutant Fortilin transfectants were subjected to SDS-PAGE and Western-blot analysis. Approximately equal amount of proteins were loaded as evidenced by comparable actin signals. Sizes of wild type Fortilin (Fortilin$_{wild(1-172)}$) and Fortilin mutants (Fortilin$_{\Delta 5-172}$, Fortilin$_{\Delta 5-172}$, Fortilin$_{\Delta 5-172}$) were appropriate. Consistent with the result from the experiment presented in FIG. 13, the expression levels of MCL1 were similar between stable transfectants expressing wild type Fortilin and control stable transfectants that possess the empty plasmid (FIG. 15 "MCL1 Expression Index"). Furthermore, the expression levels of MCL1 were similar between stable transfectants expressing wild type Fortilin and those expressing mutant Fortilins (FIG. 15, "MCL1 Expression Index"). Therefore, the functional difference among these mutants could not have been caused by the difference in intracellular MCL1 concentrations of these mutants.

Finally, in order to determine whether the interaction pattern observed in vitro between MCL1 and various Fortilin mutants could also be observed in vivo in stable transfectants, immunoprecipitation assay using anti-HA antibody was performed. The presence of co-immunoprecipitated MCL1 was evaluated by anti-MCL1 antibody. There were an adequate amount of MCL1 in all of the cell lysates and an adequate amount of Fortilin in cell lysates from wild-type Fortilin and mutant Fortilin transfectants. All Fortilins were successfully immunoprecipitated by the same anti-HA antibody used to assess in vitro interaction. Consistent with in vitro data presented above (FIG. 14), wild type Fortilin and Fortilin$_{\Delta 5-172}$, but not Fortilin$\Delta$23-172 or Fortilin$\Delta$46-172, co-immunoprecipitated MCL1. These stable transfectant cells were used for the experiments described in FIG. 16.

Example 22

Fortilin is an Antianoptotic Protein whose Antiapoptotic Activity is at Least Partially Dependent on its Binding to MCL1

Figure 16:
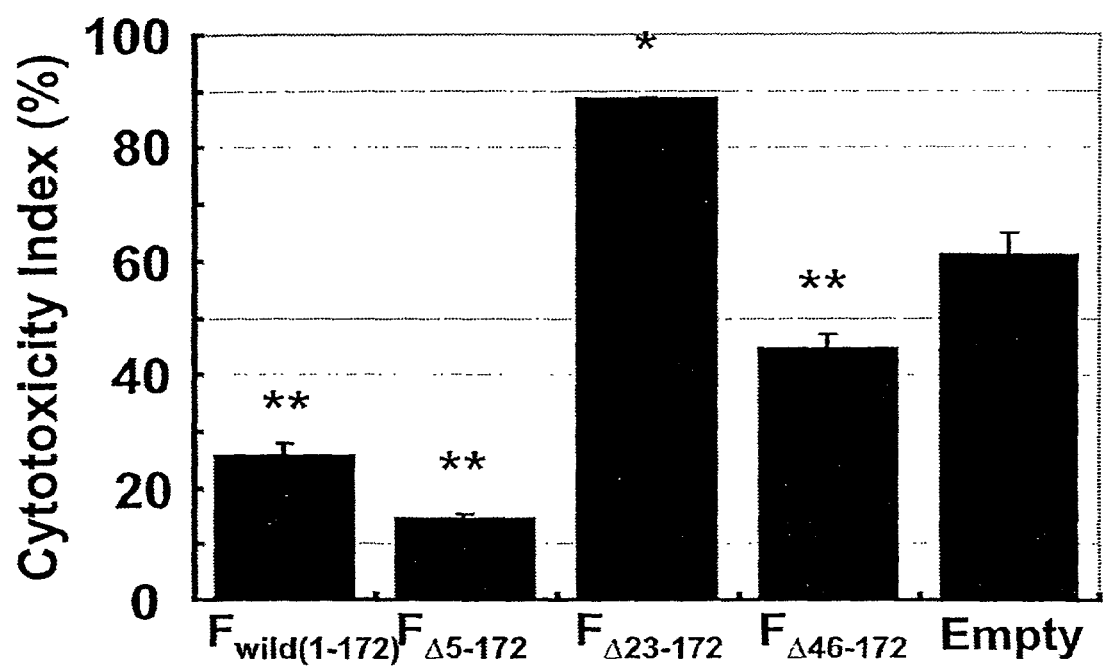
FIG. 16. The role of fortilin binding to MCL1 in etoposide-induced cytotoxicity in U2OS cells: Fortilin blocks etoposide-induced apoptosis in U2OS cells in a MCL1 dependent fashion. U2OS cells were stably transfected with pcDNA6-fortilin-HA, pcDNA6-fortilin$_{\Delta 5-172}$-HA, pcDNA6-fortilin$_{\Delta 23-172}$-HA, or pcDNA6-fortilin$_{\Delta 46-172}$-HA. The expression of HA-tagged fortilin and fortilin mutants had been confirmed by immunostaining and Western blot analysis. U2OS transfectants stably expressing wild-type fortilin ($F_{wild(1-172)}$) or its deletion mutants fortilin$_{\Delta 5-172}$ ($F_{\Delta 5-172}$), fortilin$_{\Delta 23-172}$ ($F_{\Delta 23-172}$), fortilin$_{\Delta 46-172}$ ($FA_{\Delta 46-172}$), as well as control U2OS cells were seeded in triplicate in 96-well plates. All cells were challenged with 5 µg/mL of etoposide for 48 hours. Cell media were then retrieved and assayed for lactose dehydrogenase (LDH) activities, which correlated with the number of cells that were damaged by etoposide and released the cytosolic enzyme LDH into the media. Cytotoxicity indices were calculated (see Experimental Procedures). The cytotoxicity indices of cells stably expressing wild-type fortilin, fortilin$_{\Delta 5-172}$ and fortilin$_{\Delta 46-172}$ were significantly lower than the cytotoxicity index of control cells. The cytotoxicity index of cells stably expressing fortilin$_{\Delta 23-172}$ was significantly higher than that of control cells. Asterisks (*, **) denote the statistically significant P values of 0.01 and 0.005, respectively, in comparison with control cells.

U2OS cells stably expressing either Fortilin or its mutants as described above (FIG. 15), were further utilized to assess how the binding of Fortilin to MCL1 would affect the ability of cells to survive in the presence of noxious stimuli. The mutant transfectant cells were challenged with the chemotherapeutic agent etoposide for 48 hours, and assessed for the resulting degree of cytotoxicity (i.e., the cytotoxicity index). Strikingly, cytotoxicity indices were significantly lower in cells stably expressing wild type Fortilin or Fortilin$_{\Delta 5-172}$ (both of which are capable of interacting with MCL1) than in control transfectants (FIG. 16), suggesting that Fortilin functioned as a potent anti-apoptotic molecule when it was capable of interacting with MCL1. Surprisingly, Fortilin$_{\Delta 23-172}$, which is not capable of interacting with MCL1 (FIGS. 14 and 15), could not prevent cells from undergoing etoposide-induced cell death and instead sensitized the cells to etoposide-induced cell death (FIG. 16). Intriguingly, Fortilin$_{\Delta 45-172}$, another Fortilin mutant that failed to interact with MCL1 (FIGS. 14 and 15), was still capable of protecting cells, albeit modestly, from etoposide-induced cell death (FIG. 16). These results were significant for three reasons: First, they suggested that Fortilin$_{\Delta 23-172}$ might be a dominant negative mutant of Fortilin that nullified the antiapoptotic effect of native Fortilin thereby sensitizing cells to etoposide-induced cell death. Second, the fact that the death protection afforded by Fortilin$_{\Delta 45-172}$ was significantly greater than that seen in controls (FIG. 16, "Fortilin$_{\Delta 46-172}$" vs. "Empty"), indicated that the anti-apoptotic activity of Fortilin was not entirely dependent on Fortilin's interaction with MCL1 and that Fortilin could function as an antiapoptotic molecule without interacting with MCL1. Although Fortilin$\Delta$46-172 lacks 26% of wild type Fortilin, the fact that intracellular localization of Fortilin$_{\Delta 46-172}$ was identical to that of wild type Fortilin support that the folding of this mutant had not been significantly altered by the deletion.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EPA No. 320 308
EPA No. 329 822
GB Application No. 2,202,328
GB Application No. 2193095
PCT/US85/01161
PCT/US87/00880
PCT/US89/01025
PCT/US89/05040
U.S. Pat. No. 3,817,837
U.S. Pat. No. 3,850,752
U.S. Pat. No. 3,939,350
U.S. Pat. No. 3,996,345
U.S. Pat. No. 4,162,282
U.S. Pat. No. 4,196,265
U.S. Pat. No. 4,275,149
U.S. Pat. No. 4,277,437
U.S. Pat. No. 4,310,505
U.S. Pat. No. 4,366,241
U.S. Pat. No. 4,533,254
U.S. Pat. No. 4,554,101
U.S. Pat. No. 4,683,195
U.S. Pat. No. 4,683,202
U.S. Pat. No. 4,684,611
U.S. Pat. No. 4,728,575

U.S. Pat. No. 4,728,578
U.S. Pat. No. 4,737,323
U.S. Pat. No. 4,800,159
U.S. Pat. No. 4,873,191
U.S. Pat. No. 4,879,236
U.S. Pat. No. 4,883,750
U.S. Pat. No. 4,921,706
U.S. Pat. No. 4,946,773
U.S. Pat. No. 4,952,500
U.S. Pat. No. 5,054,297
U.S. Pat. No. 5,175,384
U.S. Pat. No. 5,175,385
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,399,363
U.S. Pat. No. 5,464,765
U.S. Pat. No. 5,466,468
U.S. Pat. No. 5,530,179
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,565,186
U.S. Pat. No. 5,580,859
U.S. Pat. No. 5,589,466
U.S. Pat. No. 5,591,616
U.S. Pat. No. 5,609,870
U.S. Pat. No. 5,610,042
U.S. Pat. No. 5,612,486
U.S. Pat. No. 5,616,491
U.S. Pat. No. 5,625,125
U.S. Pat. No. 5,639,457
U.S. Pat. No. 5,641,515
U.S. Pat. No. 5,656,610
U.S. Pat. No. 5,693,762
U.S. Pat. No. 5,702,932
U.S. Pat. No. 5,736,524
U.S. Pat. No. 5,739,169
U.S. Pat. No. 5,780,448
U.S. Pat. No. 5,785,970
U.S. Pat. No. 5,789,215
U.S. Pat. No. 5,801,005
U.S. Pat. No. 5,824,311
U.S. Pat. No. 5,830,880
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,225
U.S. Pat. No. 5,846,233
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,155
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,871,986
U.S. Pat. No. 5,879,703
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,980,912
U.S. Pat. No. 5,981,274
U.S. Pat. No. 5,994,624
U.S. Pat. No. 6,020,192
U.S. Pat. No. 6,027,727
U.S. Pat. No. 6,054,297
WO 84/03564
WO 88/10315
WO 89/06700
WO 90/07641
WO 94/09699
WO 95/06128
WO 99/18933

Abbondanzo et al., *Breast Cancer Res. Treat.*, 16:182(#151), 1990.
Adams & Cory, *Science.* 281:1322-6, 1998.
Allred et al., *Breast Cancer Res. Treat.*, 16:182(#149), 1990.
Almendro et al., *J Immunol.*, 157:5411-5421, 1996.
Ambrosini et al., *Nat Med.*, 3:917-21, 1997.
Angel et al., *Cell*, 49:729, 1987b.

Angel et al., *Mol. Cell. Biol.*, 7:2256, 1987a.
Arap et al., *Cancer Res.*, 55:1351-1354, 1995.
Atchison and Perry, *Cell*, 46:253, 1986.
Atchison and Perry, *Cell*, 48:121, 1987.
Austin-Ward, Villaseca, *Rev. Med. Chil.*, 126(7):838-45, 1998.
Ausubel et al., *Current Protocols in Molecular Biology*, (John Wiley & Sons, Inc., New York, N.Y., 1998.
Ausubel, ed., Current protocols in molecular biology, New York, John Wiley & Sons, 1996.
Baichwal and Sugden, In: *Gene Transfer*, Kucherlapati R, ed., New York, Plenum Press, pp. 117-148, 1986.
Bajorin et al., *Proc. Annu. Meet. Am. Soc. Clin. Oncol.*, 7:A967, 1988.
Bakhshi et al., *Cell*, 41(3):899-906, 1985.
Banerji et al., *Cell*, 27:299, 1981.
Banerji et al., *Cell*, 35:729, 1983.
Bangham, et al., *J. Mol. Biol.*, 13:238-252, 1965.
Bellus, *J. Macromol. Sci. Pure Appl. Chem*, A31(1): 1355-1376, 1994.
Benjamini, "Immunology: A Short Course," Wiley-Liss, New York (3rd ed., 1991).
Berkhout et al., *Cell*, 59:273, 1989.
Berzal-Herranz, A. et al., *Genes and Devel.*, 6:129-134, 1992.
Blanar et al., *EMBO J.*, 8:1139, 1989.
Bodine and Ley, *EMBO J.*, 6:2997, 1987.
Bonavida et al., *Int J Oncol*, 15:793-802, 1999.
Bonavida et al., *Proc Nat'l Acad Sci USA*. 97:1754-9, 2000.
Boshart et al., *Cell*, 41:521, 1985.
Bosze et al., *EMBO J.*, 5:1615, 1986.
Braddock et al., *Cell*, 58:269, 1989.
Brinster et al., *Proc. Nat'l Acad. Sci. USA*, 82:4438-4442, 1985.
Brown et al. *Breast Cancer Res. Treat.*, 16:192(#191), 1990.
Brutlag et al., *CABIOS*, 6:237-245, 1990.
Bukowski et al., *Clin. Cancer Res.*, 4(10):2337-47, 1998.
Bulla and Siddiqui, *J. Virol.*, 62:1437, 1986.
Caldas et al., *Nat. Genet.*, 8:27-32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Canfield et al., *Methods in Enzymology*, 189, 418-422, 1990.
Capaldi et al., *Biochem. Biophys. Res. Comm.*, 76:425, 1977.
Carbonelli et al. *FEMS Microbiol Lett.* 177(1):75-82, 1999.
Cech et al., *Cell*, 27:487-496, 1981.
Celander and Haseltine, *J. Virology*, 61:269, 1987.
Celander et al., *J. Virology*, 62:1314, 1988.
Chandler et al., *Cell*, 33:489, 1983.
Chandler et al., *Proc Natl Acad Sci USA*. 94(8):3596-3601, 1997.
Chatterjee et al., *Proc. Nat'l Acad. Sci. USA.*, 86:9114, 1989.
Chen and Okayama, *Mol. Cell Biol.*, 7:2745-2752, 1987.
Cheng et al., *Cancer Res.*, 54:5547-5551, 1994.
Cheng, et al., *Investigative Radiology*, vol. 22, pp. 47-55 (1987).
Chitpatima et al., *Nucleic Acids Res.*, 16:2350, 1988.
Chou and Fasman, "Conformational Parameters for Amino Acids in Helical, β-Sheet, and Random Coil Regions Calculated from Proteins," *Biochemistry*, 13(2):211-222, 1974b.
Chou and Fasman, *Adv. Enzymol. Relat. Areas Mol. Biol.*, 47:45-148, 1978a.
Chou and Fasman, *Ann. Rev. Biochem.*, 47:251-276, 1978b.
Chou and Fasman, *Biochemistry*, 13(2):222-245, 1974a.
Chou and Fasman, *Biophys. J.*, 26:367-384, 1979.
Chowrira, B. H. et al., *Biochemistry*, 32:1088-1095, 1993.
Chowrira, B. H. et al., *J. Biol. Chem.*, 269:25856-25864, 1994.
Christodoulides et al., *Microbiology*, 144(Pt 11):3027-37, 1998.
Chung et al., *Cancer Lett.*, 156:185-90, 2000.
Cleary and Sklar, *Proc. Nat'l Acad. Sci. USA*, 82(21):7439-43, 1985.
Cleary et al., *J. Exp. Med.*, 164(1):315-20, 1986.
ClonTech. Yeast Protocols Handbook 1997.
Cocea, *Biotechniques*. 23(5):814-816, 1997.
Cohen et al., *J. Cell. Physiol.*, 5:75, 1987.
Costa et al., *Mol. Cell. Biol.*, 8:81, 1988.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Culver et al., *Science*, 256:1550-1552, 1992.
Daidone et al., *Endocr Relat Cancer*, 6;61-8, 1999.
Dandolo et al., *J. Virology*, 47:55, 1983.
Davidson et al., *J. Immunother.*, 21(5):389-98, 1998.
De Villiers et al., *Nature*, 312:242, 1984.
Deamer and P. Uster, Liposomes (M. Ostro, ed.), Marcel Dekker, Inc., New York, pp. 27-52, 1983.
Dejager et al., *J. Clin. Invest.*, 92:894-902, 1993.
Deschamps et al., *Science*, 230:1174, 1985.
Deveraux et al., *Nature* 388:300-4, 1997.
Dillman *Cancer Biother. Radiopharm.*, 14:5-10, 1999.
Doolittle et al., *Methods Mol. Biol.*, 109:215-37, 1999.
Duckett et al., *Embo J.*, 15:2685-94, 1996.
Edbrooke et al., *Mol. Cell. Biol.*, 9:1908, 1989.
Edlund et al., *Science*, 230:912, 1985.
Eichinger et al., *J Biol Chem* 273(21), 12952-9, 1998.
El-Gorab et al., *Biochem. Biophys. Acta*, 1973, 306, 58-66, 1973.
Engelman et al., *Annu Rev Biophys Biophys Chem.*, 15:321-53, 1986.
Fechheimer et al., *Proc. Nat'l Acad. Sci. USA*, 84:8463-8467, 1987.
Fendler et al., Catalysis in Micellar and Macromolecular Systems, Academic Press, New York, 1975.
Feng and Holland, *Nature*, 334:6178, 1988.
Fetrow and Bryant, *Biotech.*, 11:479-483, 1993.
Firak and Subramanian, *Mol. Cell. Biol.*, 6:3667, 1986.
Fodor et al., *Science*, 251-:767-773, 1991.
Foecking and Hofstetter, *Gene*, 45(1):101-5, 1986.
Folkman and Shing, *J Biol Chem* 267(16), 10931-10934, 1987.
Folkman and Klagsbrun, *Science*, 235: 442-447, 1987.
Forster and Symons, *Cell*, 49:211-220, 1987.
Fraley et al., *Proc. Nat'l Acad. Sci. USA*, 76:3348-3352, 1979.
Friedmann, *Science*, 244:1275-1281, 1989.
Frohman, In: *PCR Protocols: A Guide To Methods And Applications*, Academic Press, N.Y., 1990.
Fujise et al., *J Biol Chem* 275, 39458-39465, 2000.
Fujita et al., *Cell*, 49:357, 1987.
Fung-Leung et al., *Cell*, 65:443-449, 1991a.
Fung-Leung et al., *J. Exp. Med.*, 174:1425-1429, 1991b.
Gabizon et al., *Cancer Res.*, 50(19):6371-8, 1990.
Gerlach et al., *Nature (London)*, 328:802-805, 1987.
Ghose and Blair, *Crit. Rev. Ther. Drug Carrier Syst.*, 3(4): 263-359, 1987.
Ghosh and Bachhawat, *In: Liver diseases, targeted diagnosis and therapy using specific receptors and ligands*, (Wu G, Wu C ed.), New York: Marcel Dekker, pp. 87-104, 1991.
Gilles et al., *Cell*, 33:717, 1983.
Gliniak et al., *Cancer Res.* 59:6153-8, 1999.
Gloss et al., *EMBO J.*, 6:3735, 1987.
Godbout et al., *Mol. Cell. Biol.*, 8:1169, 1988.

Gong et al., *J Biol Chem.*, 272:28198-201, 1997.
Goodbourn and Maniatis, *Proc. Nat'l Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989.
Gregoriadis, ed., Drug Carriers In Biology And Medicine, pp. 287-341, 1979.
Gregoriadis, G., ed., Liposome Technology, vol. I, pp. 30-35, 51-65 and 79-107 (CRC Press Inc., Boca Raton, Fla., 1984.
Gross et al., *Nucleic Acids Res.*, 17:8367, 1989.
Grosschedl and Baltimore, *Cell*, 41:885, 1985.
Guidozzi, et al., *Gynecol Oncol.*, 61:204-9, 1996.
Gulbis et al., *Hum. Pathol.*, 24:1271-85, 1993.
Hacia et al., *Nature Genetics*, 14:441-447, 1996.
Hande et al., *Eur J Cancer,* 34:1514-21, 1998.
Hanibuchi et al., *Int. J. Cancer,* 78(4):480-5, 1998.
Harland and Weintraub, *J. Cell Biol.*, 101:1094-1099, 1985.
Harlow and Lane, "Antibodies: A Laboratory Manual," Cold Spring Harbor Laboratory, 1988.
Haseloff and Gerlach, *Nature*, 334:585-591, 1988.
Haslinger and Karin, Proc. Nat'l Acad. Sci. USA., 82:8572, 1985.
Hauber and Cullen, *J. Virology*, 62:673, 1988.
Hellstrand et al., *Acta. Oncol.*, 37(4):347-53, 1998.
Hen et al., *Nature*, 321:249, 1986.
Hensel et al., *Lymphokine Res.*, 8:347, 1989.
Hermonat and Muzyczka, *Proc. Nat'l. Acad. Sci. USA*, 81:6466-6470, 1984.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Hogan et al., *Manipulating the Mouse Embryo*, Cold Spring Harbor Laboratory, Cold Spring Harbor, N.Y., 1986.
Holbrook et al., *Virology*, 157:211, 1987.
Hollstein et al., *Science* 253:49-53, 1991.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol Cell Biol.*, 8:3065, 1988.
Hui and Hashimoto, *Infect. Immun.*, 66(11):5329-36, 1998.
Hussussian et al., *Nature Genetics*, 15-21, 1994.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., "DNA sequencing with Thermus aquaticus DNA polymerase and direct sequencing of polymerase chain reaction-amplified DNA," *Proc Natl Acad Sci USA.* 85(24):9436-9440, 1988.
Inouye et al., *Nucleic Acids Res.*, 13:3101-3109, 1985.
Irie & Morton, *Proc. Nat'l Acad. Sci. USA* 83:8694-8698, 1986
Irie et al., "Melanoma gangliosides and human monoclonal antibody," In: *Human Tumor Antigens and Specific Tumor Therapy*, Metzgar & Mitchell (eds.), Alan R. Liss, Inc., New York, pp. 115-126, 1989.
Jakobovits et al., *Mol. Cell. Biol.*, 8:2555, 1988.
Jameel and Siddiqui, *Mol. Cell. Biol.*, 6:710, 1986.
Jameson and Wolf, *Comput. Appl. Biosci.*, 4(1):181-186, 1988.
Jaynes et al., *Mol. Cell. Biol.*, 8:62, 1988.
Johnson et al., *J. Virol.*, 67:438-445,1993.
Johnson et al., *Mol. Cell. Biol.*, 9:3393, 1989.
Joyce, *Nature*, 338:217-244, 1989.

Ju et al., *Gene Ther.*, 7(4):329-38, 2000.
Kadesch and Berg, *Mol. Cell. Biol.*, 6:2593, 1986.
Kaeppler et al., *Plant Cell Reports* 9: 415-418, 1990.
Kamb et al., *Nature Genetics*, 8:22-26, 1994.
Kamb et al., *Science*, 2674:436-440, 1994.
Kamitani et al., *J Biol Chem.*, 272:28557-62, 1997.
Kaneda et al., *Science*, 243:375-378, 1989.
Karin et al., *Mol. Cell. Biol.*, 7:606, 1987.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Keane et al., *Cancer Res.* 59:734-41, 1999.
Kerr et al., *Br. J. Cancer,* 26(4):239-57, 1972.
Kiledjian et al., *Mol. Cell. Biol.*, 8:145, 1988.
Kim and Cech, *Proc. Nat'l Acad. Sci. USA,* 84:8788-8792, 1987.
Klamut et al., *Mol. Cell. Biol.*, 10:193, 1990.
Koch et al., *Mol. Cell. Biol.*, 9:303, 1989.
Kraus et al. *FEBS Lett.*, 428(3):165-170, 1998.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., *In: Cancer Cells 2/Oncogenes and Viral Genes*, Van de Woude et al. eds, Cold Spring Harbor, Cold Spring Harbor Laboratory, 1984b.
Kriegler et al., *In: Gene Expression*, D. Hamer and M. Rosenberg, eds., New York: Alan R. Liss, 1983.
Kuhl et al., *Cell*, 50:1057, 1987.
Kunz et al., *Nucl. Acids Res.*, 17:1121, 1989.
Kwoh et al., *Proc. Nat. Acad. Sci. USA*, 86: 1173, 1989.
Kyte and Doolittle, *J. Mol. Biol.*, 157(1):105-132, 1982.
Landis et al., *CA Cancer J. Clin.*, 48:6, 1998.
Lareyre et al., *J Biol Chem.*, 274(12):8282-8290, 1999.
Larsen et al., *Proc. Nat'l Acad. Sci. USA.*, 83:8283, 1986.
Laspia et al., *Cell*, 59:283, 1989.
Latimer et al., *Mol. Cell. Biol.*, 10:760, 1990.
Lee et al., *J Auton Nerv Syst.* 74(2-3):86-90, 1997.
Lee et al., *Nature*, 294:228, 1981.
Lee et al., *Nucleic Acids Res.*, 12:4191-206, 1984.
Levenson et al., *Hum Gene Ther.* 20;9(8):1233-1236, 1998.
Levinson et al., *Nature*, 295:79, 1982.
Lieber and Strauss, *Mol. Cell. Biol.*, 15: 540-551, 1995.
Lin et al., *Mol. Cell. Biol.*, 10:850, 1990.
Luria et al., *EMBO J.*, 6:3307, 1987.
Lusky and Botchan, *Proc. Nat'l Acad. Sci. USA.*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Nat'l Acad. Sci. USA.*, 80:5866, 1983.
Mannick et al., *Science* 284(5414), 651-4, 1999.
Marsters et al., *Recent Prog Horm Res* 54:225-34, 1999.
Martin et al., *Nature*, 345(6277):739-743, 1990.
Mayer et al., *Biochimica et Biophysica Acta*, vol. 858, pp. 161-168, 1986.
Mayhew et al., *Biochimica et Biophysica Acta*, vol. 775, pp. 169-174, 1984.
Mayhew et al., *Methods in Enzymology*, vol. 149, pp. 64-77, 1987.
McNeall et al., *Gene*, 76:81, 1989.
Michel and Westhof, *J. Mol. Biol.*, 216:585-610, 1990.
Miksicek et al., *Cell*, 46:203, 1986.
Mitchell et al., *Ann. N.Y. Acad. Sci.*, 690:153-166, 1993.

Mitchell et al., *J. Clin. Oncol,.* 8(5):856-859, 1990.
Monzo et al., *J Clin Oncol.,* 17:2100-4, 1999.
Mordacq and Linzer, *Genes and Dev.,* 3:760, 1989.
Moreau et al., *Nucl. Acids Res.,* 9:6047, 1981.
Mori et al., *Cancer Res.,* 54:3396-3397, 1994.
Morton and Ravindranath, M. H. Current concepts concerning melanoma vaccines. In *Tumor Immunology,* Dalgleish A G (ed.), London: Cambridge University Press, 1-55, 1996.
Morton et al., *Ann. Surg.* 216: 463-482, 1992.
Moulding et al., *Blood* 92(7), 2495-502, 1998.
Muesing et al., *Cell,* 48:691, 1987.
Nakamura et al., *In: Enzyme Immunoassays: Heterogeneous and Homogeneous Systems,* Chapter 27, 1987.
Ng et al., *Nuc. Acids Res.,* 17:601, 1989.
Nicolas and Rubenstein, *In: Vectors: A survey of molecular cloning vectors and their uses,* Rodriguez and Denhardt (eds.), Stoneham: Butterworth, pp. 493-513, 1988.
Nicolau and Sene, *Biochim. Biophys. Acta,* 721:185-190, 1982.
Nicolau et al., *Methods Enzymol.,* 149:157-176, 1987.
Nigg, *Nature,* 386:779-87, 1997.
Nobri et al., *Nature,* 368:753-756, 1995.
Nomoto et al., *Gene,* 236(2):259-271, 1999.
Ohara et al., *Proc. Nat'l Acad. Sci. USA,* 86: 5673-5677, 1989.
Okamoto et al., *Proc. Nat'l Acad. Sci. USA,* 91:11045-11049, 1994.
Omirulleh et al., *Plant Mol. Biol.,* 21:415-28, 1993.
Ondek et al., *EMBO J.,* 6:1017, 1987.
Orlow et al., *Cancer Res.,* 54:2848-2851, 1994.
Ornitz et al., *Mol. Cell. Biol.,* 7:3466, 1987.
Palmiter et al., *Nature,* 300:611, 1982
Palukaitis et al., *Virology,* 99:145-151, 1979.
Pease et al., *Proc. Natl. Acad. Sci. USA,* 91:5022-5026, 1994.
Pech et al., *Mol. Cell. Biol.,* 9:396, 1989.
Pelletier and Sonenberg, *Nature,* 334:320-325, 1988.
Perez-Stable and Constantini, *Mol. Cell. Biol.,* 10:1116, 1990.
Perriman. et al., *Gene,* 113:157-163, 1992.
Perrotta and Been, *Biochemistry* 31:16, 1992.
Pfeffer et al., *Cell,* 73:457-467, 1993.
Picard and Schaffner, *Nature,* 307:83, 1984.
Pietras et al., *Oncogene,* 17(17):2235-49, 1998.
Pinkert et al., *Genes and Dev.,* 1:268, 1987.
Ponta et al., *Proc. Nat'l Acad. Sci. USA.,* 82:1020, 1985.
Porton et al., *Mol. Cell. Biol.,* 10:1076, 1990.
Potrykus et al., *Mol. Gen. Genet.,* 199:183-188, 1985.
Prody, G. A. et al., *Science,* 231, 1577-1580, 1986.
Qin et al., *Proc. Nat'l Acad. Sci. USA,* 95(24):1411-6, 1998.
Queen and Baltimore, *Cell,* 35:741, 1983.
Quinn et al., *Mol. Cell. Biol.,* 9:4713, 1989.
Ravindranath and Morton, *Intern. Rev. Immunol.* 7: 303-329, 1991.
Redondo et al., *Science,* 247:1225, 1990.
Reinhold-Hurek and Shub, *Nature,* 357:173-176, 1992.
Reisman and Rotter, *Mol. Cell. Biol.,* 9:3571, 1989.
Remington's Pharmaceutical Sciences, 15$^{th}$ ed., pages 1035-1038 and 1570-1580, Mack Publishing Company, Easton, Pa., 1980.
Resendez Jr. et al., *Mol. Cell. Biol.,* 8:4579, 1988.
Ridgeway, *In: Vectors: A survey of molecular cloning vectors and their uses,* Rodriguez R L, Denhardt D T, ed., Stoneham:Butterworth, pp. 467-492, 1988.
Ripe et al., *Mol. Cell. Biol.,* 9:2224, 1989.
Rippe et al., *Mol. Cell Biol.,* 10:689-695, 1990.
Rittling et al., *Nucl. Acids Res.,* 17:1619, 1989.
Rosen et al., *Cell,* 41:813, 1988.
Rosenberg et al., *Ann. Surg.,* 210:474, 1989.
Rosenberg et al., *N. Engl. J. Med.,* 319:1676, 1988.
Sakai et al., *Genes and Dev.,* 2:1144, 1988.
Sambrook et al., *In: Molecular Cloning: A Laboratory Manual,* 2nd Ed., Cold Spring Harbor Press, Cold Spring Harbor, N.Y., 1989.
Sanford et al., *Journal of National Cancer Institute,* 9:229-246, 1948.
Sarver, et al, *Science,* 247:1222-1225, 1990.
Satake et al., *J. Virology,* 62:970, 1988.
Sato & Yamashina, *Biochim Biophys Acta,* 397:179-87, 1975.
Scanlon et al., *Proc. Nat'l Acad. Sci. USA,* 88:10591-10595, 1991.
Schaffner et al., *J. Mol. Biol.,* 201:81, 1988.
Schmitt et al., *Exp Cell Res.,* 240:107-21, 1998.
Searle et al., *Mol. Cell. Biol.,* 5:1480, 1985.
Serrano et al., *Nature,* 366:704-707, 1993.
Serrano et al., *Science,* 267:249-252, 1995.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Shinoda, K. et al., Colloidal Surfactant, Academic Press, especially "The Formation of Micelles", Ch. 1, 1-96, 1963.
Shoemaker et al., *Nature Genetics,* 14:450-456, 1996.
Sioud et al., *J. Mol. Biol.,* 223:831-835, 1992.
Sleigh and Lockett, *J. EMBO,* 4:3831, 1985.
Spalholz et al., *Cell,* 42:183, 1985.
Spandau and Lee, *J. Virology,* 62:427, 1988.
Spandidos and Wilkie, *EMBO J.,* 2:1193, 1983.
Stephens and Hentschel, *Biochem. J.,* 248:1, 1987.
Stuart et al., *Nature,* 317:828, 1985.
Sullivan and Peterlin, *Mol. Cell. Biol.,* 7:3315, 1987.
Swartzendruber and Lehman, *J. Cell. Physiology,* 85:179, 1975.
Symons, *Ann. Rev. Biochem.,* 61:641-671, 1992.
Symons, *Nucl. Acids Res.,* 9:6527-6537, 1981.
Szoka et al., *Proc. Natl. Acad. Sci.,* 1978, 75:4194-4198.
Takebe et al., *Mol. Cell. Biol.,* 8:466, 1988.
Taules et al., *J. Biol Chem.,* 274:24445-8, 1999.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Temin, *In: Gene Transfer,* Kucherlapati (ed.), New York: Plenum Press, pp. 149-188, 1986.
Templeton et al., *Nat. Biotechnol.,* 15(7):647-52, 1997.
Thiele et al., *Eur. J. Biochem.,* 267:5473-81, 2000.
Thiesen et al., *J. Virology,* 62:614, 1988.
Thompson et al. *Nature Medicine,* 1:277-278, 1995.
Tronche et al., *Mol. Biol. Med.,* 7:173, 1990.
Tronche et al., *Mol. Cell. Biol.,* 9:4759, 1989.
Trudel and Constantini, *Genes and Dev.,* 6:954, 1987.
Tsujimoto and Croce, *Proc. Natl. Acad. Sci. USA,* 83(14): 5214-8, 1986.
Tsujimoto et al., *Science,* 228(4706):1440-3, 1985.
Tsumaki et al., *J Biol Chem.* 273(36):22861-22864, 1998.
Tyndall et al., *Nuc. Acids. Res.,* 9:6231, 1981.
Vannice and Levinson, *J. Virology,* 62:1305, 1988.
Vasseur et al., *Proc. Nat'l Acad. Sci. USA.,* 77:1068, 1980.
von Heijne, *Eur J Biochem* 116:419-22, 1981.
Wada et al., *Nucleic Acids Res.,* 18:2367-2411, 1990.
Walker et al., *Proc. Nat'l Acad. Sci. USA,* 89:392-396 1992.
Wang and Calame, *Cell,* 47:241, 1986.
Wawrzynczak & Thorpe, *Cancer Treat. Res.,* 37:239-51, 1988.
Weber et al., *Cell,* 36:983, 1984.
Weinberger et al. *Mol. Cell. Biol.,* 8:988, 1984.

Weinberger et al., *Science,* 228:740-742, 1985.
Winoto and Baltimore, *Cell,* 59:649, 1989.
Wolf et al., *Comput. Appl. Biosci.,* 4(1):187-191, 1988.
Wong et al., *Gene,* 10:87-94, 1980.
Wu et al., *Biochem. Biophys. Res. Commun.,* 233(1):221-6, 1997.
Yuan and Altman, *Science,* 263:1269-1273, 1994.
Yuan et al., *Proc. Nat'l Acad. Sci. USA,* 89:8006-8010, 1992.
Yutzey et al. *Mol. Cell. Biol.,* 9:1397, 1989.
Zhao-Emonet et al., *Biochem. Biophys. Acta.,* 1442(2-3):109-19, 1998.
Zoldhelyi, *Circulation* 93, 10-17, 1996.
Zoldhelyi et al., *Circulation* 101(3), 289-95, 2000.
Zhou et al., *Blood,* 89:630-43, 1997.

---

What is claimed is:

1. A method of identifying a modulator of a Fortilin polypeptide comprising:
   (a) contacting an isolated Fortilin polypeptide comprising the amino acid sequence of SEQ ID NO:2 with a candidate substance; and
   (b) assaying whether the candidate substance disrupts p53-Fortilin or MCL1-Fortlin binding, wherein a candidate substance that disrupts p53-Fortilin or MCL1-Fortilin binding is a modulator of the Fortilin polypeptide.

2. A method of identifying a modulator of a Fortilin polypeptide comprising:
   (a) contacting a candidate modulator with isolated, recombinant cells expressing a Fortilin polypeptide comprising the amino acid sequence of SEQ ID NO:2;
   (b) measuring the level of Fortilin activity of the cell; and,
   (c) comparing the level of Fortilin activity of the cells to the level of Fortilin activity of cells not expressing a Fortilin polypeptide comprising the amino acid sequence of SEQ ID NO:2, wherein Fortilin activity is inhibition of apoptosis,
   wherein a difference between the level of Fortilin activity indicates that the candidate modulator is a modulator of a Fortilin polypeptide.

3. The method of claim 2, wherein the candidate substance is a polypeptide.

4. The method of claim 3, wherein the polypeptide is an antibody.

5. The method of claim 2, wherein the candidate substance is a nucleic acid.

6. The method of claim 5, wherein the nucleic acid comprises at least 20 contiguous nucleotides identical or complementary to SEQ ID NO:1.

7. The method of claim 2, wherein the candidate substance is a small molecule.

8. The method of claim 2, wherein the candidate modulator acts directly on a Fortilin gene or Fortilin RNA.

* * * * *

SEQUENCE LISTING

```
<160> NUMBER OF SEQ ID NOS: 12

<210> SEQ ID NO 1
<211> LENGTH: 830
<212> TYPE: DNA
<213> ORGANISM: Homo sapiens
<220> FEATURE:
<221> NAME/KEY: CDS
<222> LOCATION: (95)..(613)

<400> SEQUENCE: 1
cccccccgag cgccgctccg gctgcaccgc gctcgctccg agtttcaggc tcgtgctaag        60
ctagcgccgt cgtcgtctcc cttcagtcgc catc atg att atc tac cgg gac ctc       115
                                     Met Ile Ile Tyr Arg Asp Leu
                                      1               5 atc agc cac gat gag atg ttc tcc gac atc tac aag atc cgg gag atc         163
Ile Ser His Asp Glu Met Phe Ser Asp Ile Tyr Lys Ile Arg Glu Ile
         10                  15                  20 gcg gac ggg ttg tgc ctg gag gtg gag ggg aag atg gtc agt agg aca         211
Ala Asp Gly Leu Cys Leu Glu Val Glu Gly Lys Met Val Ser Arg Thr
 25                  30                  35 gaa ggt aac att gat gac tcg ctc att ggt gga aat gcc tcc gct gaa         259
Glu Gly Asn Ile Asp Asp Ser Leu Ile Gly Gly Asn Ala Ser Ala Glu
 40                  45                  50                  55 ggc ccc gag ggc gaa ggt acc gaa agc aca gta atc act ggt gtc gat         307
Gly Pro Glu Gly Glu Gly Thr Glu Ser Thr Val Ile Thr Gly Val Asp
             60                  65                  70 att gtc atg aac cat cac ctg cag gaa aca agt ttc aca aaa gaa gcc         355
Ile Val Met Asn His His Leu Gln Glu Thr Ser Phe Thr Lys Glu Ala
         75                  80                  85 tac aag aag tac atc aaa gat tac atg aaa tca atc aaa ggg aaa ctt         403
Tyr Lys Lys Tyr Ile Lys Asp Tyr Met Lys Ser Ile Lys Gly Lys Leu
     90                  95                 100 gaa gaa cag aga cca gaa aga gta aaa cct ttt atg aca ggg gct gca         451
Glu Glu Gln Arg Pro Glu Arg Val Lys Pro Phe Met Thr Gly Ala Ala
105                 110                 115 gaa caa atc aag cac atc ctt gct aat ttc aaa aac tac cag ttc ttt         499
Glu Gln Ile Lys His Ile Leu Ala Asn Phe Lys Asn Tyr Gln Phe Phe
120                 125                 130                 135 att ggt gaa aac atg aat cca gat ggc atg gtt gct cta ttg gac tac         547
Ile Gly Glu Asn Met Asn Pro Asp Gly Met Val Ala Leu Leu Asp Tyr
             140                 145                 150 cgt gag gat ggt gtg acc cca tat atg att ttc ttt aag gat ggt tta         595
Arg Glu Asp Gly Val Thr Pro Tyr Met Ile Phe Phe Lys Asp Gly Leu
         155                 160                 165 gaa atg gaa aaa tgt taa caaatgtggc aattattttg gatctatcac                643
Glu Met Glu Lys Cys
         170 ctgtcatcat aactggcttc tgcttgtcat ccacacaaca ccaggactta agacaaatgg       703 gactgatgtc atcttgagct cttcatttat tttgactgtg atttatttgg agtggaggca       763
```

```
ttgtttttaa gaaaaacatg tcatgtaggt tgtctaaaaa taaaatgcat ttaaactcat    823
ttgagag                                                              830
```

<210> SEQ ID NO 2
<211> LENGTH: 172
<212> TYPE: PRT
<213> ORGANISM: Homo sapiens

<400> SEQUENCE: 2

```
Met Ile Ile Tyr Arg Asp Leu Ile Ser His Asp Glu Met Phe Ser Asp
 1               5                  10                  15

Ile Tyr Lys Ile Arg Glu Ile Ala Asp Gly Leu Cys Leu Glu Val Glu
             20                  25                  30

Gly Lys Met Val Ser Arg Thr Glu Gly Asn Ile Asp Asp Ser Leu Ile
         35                  40                  45

Gly Gly Asn Ala Ser Ala Glu Gly Pro Glu Gly Glu Gly Thr Glu Ser
     50                  55                  60

Thr Val Ile Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

<210> SEQ ID NO 3
<211> LENGTH: 172
<212> TYPE: PRT
<213> ORGANISM: Rabbit

<400> SEQUENCE: 3

```
Met Ile Ile Tyr Arg Asp Leu Ile Ser His Asp Glu Met Phe Ser Asp
 1               5                  10                  15

Ile Tyr Lys Ile Arg Glu Ile Ala Gly Gly Leu Cys Leu Glu Val Glu
             20                  25                  30

Gly Lys Met Val Ser Arg Thr Glu Gly Asn Ile Asp Asp Ser Leu Ile
         35                  40                  45

Gly Gly Asn Ala Ser Ala Glu Gly Pro Glu Gly Glu Gly Thr Glu Ser
     50                  55                  60

Thr Val Ile Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Tyr Ile Gly Glu Asn Met Asn Pro Asp Gly
    130                 135                 140
```

```
Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170

<210> SEQ ID NO 4
<211> LENGTH: 172
<212> TYPE: PRT
<213> ORGANISM: Mus musculus

<400> SEQUENCE: 4

Met Ile Ile Tyr Arg Asp Leu Ile Ser His Asp Glu Leu Phe Ser Asp
  1               5                  10                  15

Ile Tyr Lys Ile Arg Glu Ile Ala Asp Gly Leu Cys Leu Glu Val Glu
                 20                  25                  30

Gly Lys Met Val Ser Arg Thr Glu Gly Ala Ile Asp Asp Ser Leu Ile
             35                  40                  45

Gly Gly Asn Ala Ser Ala Glu Gly Pro Glu Gly Gly Thr Glu Ser
         50                  55                  60

Thr Val Val Thr Gly Val Asp Ile Val Met Asn His His Leu Gln Glu
 65                  70                  75                  80

Thr Ser Phe Thr Lys Glu Ala Tyr Lys Lys Tyr Ile Lys Asp Tyr Met
                 85                  90                  95

Lys Ser Leu Lys Gly Lys Leu Glu Glu Gln Lys Pro Glu Arg Val Lys
                100                 105                 110

Pro Phe Met Thr Gly Ala Ala Glu Gln Ile Lys His Ile Leu Ala Asn
                115                 120                 125

Phe Asn Asn Tyr Gln Phe Phe Ile Gly Glu Asn Met Asn Pro Asp Gly
            130                 135                 140

Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170

<210> SEQ ID NO 5
<211> LENGTH: 172
<212> TYPE: PRT
<213> ORGANISM: Chicken

<400> SEQUENCE: 5

Met Ile Ile Tyr Arg Asp Cys Ile Ser Gln Asp Glu Met Phe Ser Asp
  1               5                  10                  15

Ile Tyr Lys Ile Arg Glu Val Ala Asn Gly Leu Cys Leu Glu Val Glu
                 20                  25                  30

Gly Lys Met Val Thr Arg Thr Glu Gly Gln Ile Asp Asp Ser Leu Ile
             35                  40                  45

Gly Gly Asn Ala Ser Ala Glu Gly Pro Glu Gly Gly Thr Glu Ala
         50                  55                  60

Thr Val Ile Thr Gly Val Asp Ile Val Ile Asn His His Leu Gln Glu
 65                  70                  75                  80

Thr Ser Phe Thr Lys Glu Ser Tyr Lys Lys Tyr Ile Lys Asp Tyr Met
                 85                  90                  95

Lys Ala Ile Lys Ala Arg Leu Glu Glu His Lys Pro Glu Arg Val Lys
                100                 105                 110

Pro Phe Met Thr Gly Ala Ala Glu Gln Ile Lys His Ile Leu Ala Asn
                115                 120                 125
```

```
Phe Lys Asn Tyr Gln Phe Phe Ile Gly Glu Asn Met Asn Pro Asp Gly
    130                 135                 140

Met Val Ala Leu Leu Asp Phe Arg Glu Asp Gly Val Thr Pro Tyr Met
145                 150                 155                 160

Ile Phe Phe Lys Asp Gly Leu Glu Ile Glu Lys Cys
                165                 170

<210> SEQ ID NO 6
<211> LENGTH: 172
<212> TYPE: PRT
<213> ORGANISM: D. Melanogaster

<400> SEQUENCE: 6

Met Lys Ile Tyr Lys Asp Ile Ile Thr Gly Asp Glu Met Phe Ala Asp
  1               5                  10                  15

Thr Tyr Lys Met Lys Leu Val Asp Asp Val Ile Tyr Glu Val Tyr Gly
                 20                  25                  30

Lys Leu Ile Thr Arg Gln Gly Asp Asp Ile Lys Leu Glu Gly Ala Asn
             35                  40                  45

Ala Ser Ala Glu Glu Ala Asp Glu Gly Thr Asp Ile Thr Ser Glu Ser
         50                  55                  60

Gly Val Asp Val Val Leu Asn His Arg Leu Thr Glu Cys Phe Ala Phe
 65                  70                  75                  80

Gly Asp Lys Lys Ser Tyr Thr Leu Tyr Leu Lys Asp Tyr Met Lys Lys
                 85                  90                  95

Val Leu Ala Lys Leu Glu Glu Lys Ser Pro Asp Gln Val Asp Ile Phe
                100                 105                 110

Lys Thr Asn Met Asn Lys Ala Met Lys Asp Ile Leu Gly Arg Phe Lys
            115                 120                 125

Glu Leu Gln Phe Phe Thr Gly Glu Ser Met Asp Cys Asp Gly Met Val
        130                 135                 140

Ala Leu Val Glu Tyr Arg Glu Ile Asn Gly Asp Ser Val Pro Val Leu
145                 150                 155                 160

Met Phe Phe Lys His Gly Leu Glu Glu Glu Lys Cys
                165                 170

<210> SEQ ID NO 7
<211> LENGTH: 181
<212> TYPE: PRT
<213> ORGANISM: C. ELEGANS

<400> SEQUENCE: 7

Met Leu Ile Tyr Lys Asp Ile Ile Ser Asp Glu Leu Ser Ser Asp
  1               5                  10                  15

Ser Phe Pro Met Lys Leu Val Asp Asp Leu Val Tyr Glu Phe Lys Gly
                 20                  25                  30

Lys His Val Arg Lys Glu Gly Glu Ile Val Leu Ala Gly Ser Asn
             35                  40                  45

Pro Ser Ala Glu Glu Gly Ala Glu Asp Gly Ser Asp Glu His Val
         50                  55                  60

Glu Arg Gly Ile Asp Ile Val Leu Asn His Lys Leu Val Glu Met Asn
 65                  70                  75                  80

Cys Tyr Glu Asp Ala Ser Met Phe Lys Ala Tyr Ile Lys Lys Phe Met
                 85                  90                  95

Lys Asn Val Ile Asp His Met Glu Lys Asn Asn Arg Asp Lys Ala Asp
                100                 105                 110
```

```
Val Asp Ala Phe Lys Lys Ile Gln Gly Trp Val Val Ser Leu Leu
        115                 120                 125

Ala Lys Asp Arg Phe Lys Asn Leu Ala Phe Phe Ile Gly Glu Arg Ala
        130                 135                 140

Ala Glu Gly Ala Glu Asn Gly Gln Val Ala Ile Ile Glu Tyr Arg Asp
145                 150                 155                 160

Val Asp Gly Thr Glu Val Pro Thr Leu Met Leu Val Lys Glu Ala Ile
                165                 170                 175

Ile Glu Glu Lys Cys
            180

<210> SEQ ID NO 8
<211> LENGTH: 166
<212> TYPE: PRT
<213> ORGANISM: S. Cerevisiae

<400> SEQUENCE: 8

Met Ile Ile Tyr Lys Asp Ile Phe Ser Asn Asp Glu Leu Leu Ser Asp
  1               5                  10                  15

Ala Tyr Asp Ala Lys Leu Val Asp Val Ile Tyr Glu Ala Asp Cys
             20                  25                  30

Ala Met Val Asn Val Gly Gly Asp Asn Ile Asp Ile Gly Ala Asn Pro
             35                  40                  45

Ser Ala Glu Gly Gly Asp Asp Val Glu Glu Gly Ala Glu Met Val
         50                  55                  60

Asn Asn Val Val His Ser Phe Arg Leu Gln Gln Thr Ala Phe Asp Lys
 65                  70                  75                  80

Lys Ser Phe Leu Thr Tyr Ile Lys Gly Tyr Met Lys Ala Val Lys Ala
                 85                  90                  95

Lys Leu Gln Glu Thr Asn Pro Glu Gly Val Pro Lys Phe Glu Lys Gly
            100                 105                 110

Ala Gln Thr Tyr Val Lys Lys Val Ile Gly Ser Phe Lys Asp Trp Glu
        115                 120                 125

Phe Phe Thr Gly Glu Ser Met Asp Pro Asp Ala Met Val Val Met Leu
    130                 135                 140

Asn Tyr Arg Glu Asp Gly Thr Thr Pro Phe Val Ala Ile Trp Lys His
145                 150                 155                 160

Gly Ile Val Glu Glu Lys
                165

<210> SEQ ID NO 9
<211> LENGTH: 168
<212> TYPE: PRT
<213> ORGANISM: RICE

<400> SEQUENCE: 9

Met Leu Val Tyr Gln Asp Leu Leu Tyr Gly Asp Glu Leu Leu Ser Asp
  1               5                  10                  15

Ser Phe Pro Tyr Arg Glu Ile Glu Asn Gly Ile Leu Trp Glu Val Asp
             20                  25                  30

Gly Lys Trp Val Val Gln Gly Ala Ile Asp Val Asp Ile Gly Ala Asn
             35                  40                  45

Pro Ser Ala Glu Gly Gly Gly Asp Glu Gly Val Asp Asp Gln Ala
         50                  55                  60

Val Lys Val Val Asp Ile Val Asp Thr Phe Arg Leu Gln Glu Gln Pro
 65                  70                  75                  80
```

```
Pro Phe Asp Lys Lys Gln Phe Val Thr Phe Met Lys Arg Tyr Ile Lys
                85                  90                  95

Asn Leu Ser Ala Lys Leu Asp Ala Glu Lys Gln Glu Glu Phe Lys Phe
            100                 105                 110

Asn Ile Glu Gly Ala Thr Lys Tyr Leu Leu Gly Lys Leu Lys Asp Leu
        115                 120                 125

Gln Phe Phe Val Gly Glu Ser Met His Asp Asp Gly Gly Leu Val Phe
    130                 135                 140

Ala Tyr Tyr Lys Asp Gly Ala Thr Asp Pro Thr Phe Leu Tyr Phe Ser
145                 150                 155                 160

His Gly Leu Lys Glu Val Lys Cys
                165

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10

Cys Lys Tyr Ile Lys Asp Tyr Met Lys Ser Ile Lys Gly Lys Leu Glu
1               5                   10                  15

Glu Gln Arg Pro Glu Arg
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Leu Glu Thr Leu Arg Arg Val Gly Asp Gly Val Gln Arg Asn His Glu
1               5                   10                  15

Thr Val Phe Gln Gly
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Arg Asp Leu Ile Ser His Asp Glu Met Phe Ser Asp Ile Tyr Lys Ile
1               5                   10                  15

Arg Glu
```